(12) United States Patent
Hill et al.

(10) Patent No.: US 10,793,616 B2
(45) Date of Patent: Oct. 6, 2020

(54) SINGLE-CHAIN CD40-RECEPTOR AGONIST PROTEINS

(71) Applicant: Apogenix AG, Heidelberg (DE)

(72) Inventors: Oliver Hill, Neckarsteinach (DE);
Christian Gieffers, Dossenheim (DE);
Meinolf Thiemann, Schriesheim (DE);
Tim Schnyder, Igersheim (DE)

(73) Assignee: Apogenix AG, Heidelberg (DE)

( * ) Notice: Subject to any disclaimer, the term of this patent is extended or adjusted under 35 U.S.C. 154(b) by 152 days.

(21) Appl. No.: 15/795,020

(22) Filed: Oct. 26, 2017

(65) Prior Publication Data

US 2018/0066036 A1    Mar. 8, 2018

Related U.S. Application Data

(63) Continuation of application No. PCT/EP2016/059983, filed on May 4, 2016.

(60) Provisional application No. 62/156,813, filed on May 4, 2015.

(51) Int. Cl.
*C07K 14/705* (2006.01)
*A61K 38/00* (2006.01)

(52) U.S. Cl.
CPC ........ *C07K 14/70575* (2013.01); *A61K 38/00* (2013.01); *C07K 2319/02* (2013.01); *C07K 2319/22* (2013.01); *C07K 2319/30* (2013.01); *C07K 2319/32* (2013.01); *C07K 2319/35* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 9,908,927 B2 | 3/2018 | Hill et al. | |
| 2010/0303811 A1 | 12/2010 | Ochi et al. | |
| 2011/0162095 A1* | 6/2011 | Hill | C07K 14/525 800/13 |
| 2015/0337027 A1* | 11/2015 | Hill | C07K 14/70575 424/134.1 |

FOREIGN PATENT DOCUMENTS

| | | |
|---|---|---|
| WO | 01/25277 A1 | 4/2001 |
| WO | 01/49866 A1 | 7/2001 |
| WO | 02/09055 A1 | 1/2002 |
| WO | 2004085478 A2 | 10/2004 |
| WO | 2005103077 A1 | 11/2005 |
| WO | 2006105338 A2 | 10/2006 |
| WO | 2009060159 A1 | 5/2009 |
| WO | 2010/010051 A1 | 1/2010 |
| WO | 2013136193 A2 | 9/2013 |
| WO | 2014/121099 A1 | 8/2014 |
| WO | 2014202773 A1 | 12/2014 |
| WO | 2015164588 A1 | 10/2015 |

OTHER PUBLICATIONS

Richards et al., Concepts for agonistic targeting of CD40 in immune-oncology, Human Vaccines & Immunotherapeutics, doi.org/10.1080/21645515.2019.16537, pp. 1-11, 2019. (Year: 2019).*
Attwood, Science 290:471-473, 2000. (Year: 2000).*
Skolnick et al., Trends in Biotech. 18: 34-39, 2000. (Year: 2000).*
Tetsuya Shiraishi, et al., "Increased cytotoxicity of soluble Fas ligand by fusing isoleucine zipper motif", Biochemical and Biophysical Research Communications 322 (2004) 197-202.
Li-Zhen He, et al., "Agonist Anti-Human CD27 Monoclonal Antibody Induces T Cell Activation and Tumor Immunity in Human CD27-Transgenic Mice", The Journal of Immunology, Sep. 11, 2013, 191: 4174-4183.
Pascal Schneider, et al., "Conversion of Membrane-bound Fas(CD95) Ligand to Its Soluble Form is Associated with Downregulation of Its Proapoptotic Activity and Loss of Liver Toxicity", J. Exp. Med., vol. 187, No. 8, Apr. 20, 1998, pp. 1205-1213.
International Search Report dated Jul. 6, 2016 in International Application No. PCT/EP2016/059983.
An et al., "Crystallographic and Mutational Analysis of the CD40-CD154 Complex and Its Implications for Receptor Activation", The Journal of Biological Chemistry, vol. 286, No. 13, Apr. 1, 2011, pp. 11226-11235.
Vonderheide et al., "Agonistic CD40 Antibodies and Cancer Therapy", Clinical Cancer Research, vol. 19, No. 5, Mar. 1, 2013, pp. 1035-1043.
R. Cutler Allen, et al., "CD40 Ligand Gene Defects Responsible for X-Linked Hyper-IgM Syndrome", Science, vol. 259, Feb. 12, 1993.
Xiaoying Chen, et al., "Fusion protein linkers: Property, design and functionality", Advanced Drug Delivery Reviews 65 (2013) 1357-1369.
Brigitte Gasser, et al., "Antibody production with yeasts and filamentous fungi: on the road to large scale?", Biotechnol Lett (2007) 29:201-212.
Paolo Macchi, et al., "Characterization of Nine Novel Mutations in the CD40 Ligand Gene in Patients with X-Linked Hyper IgM Syndrome of Various Ancestry", Am. J. Hum. Genet. 56:898-906, 1995.

(Continued)

*Primary Examiner* — Phillip Gambel
(74) *Attorney, Agent, or Firm* — Perkins Coie LLP; Viola Kung

(57) ABSTRACT

Provided herein are specific CD40 receptor agonist proteins, nucleic acids encoding the same, and methods of treating a subject having a CD40L-associated disease or disorder. The CD40 receptor agonist proteins provided herein comprise three soluble CD40L domains and an Fc fragment. The CD40 receptor agonist proteins are substantially non-aggregating and suitable for therapeutic, diagnostic and/or research applications.

24 Claims, 10 Drawing Sheets

Specification includes a Sequence Listing.

(56) References Cited

OTHER PUBLICATIONS

Yumi Maeda, et al., "Engineering of Functional Chimeric Protein G-Vargula Luciferase", Analytical Biochemistry 249, 147-152 (1997).
Kuniaki Seyama, et al., "Mutations of the CD40 Ligand Gene and Its Effect on CD40 Ligand Expression in Patients With X-Linked Hyper IgM Syndrome", Blood, vol. 92, No. 7, Oct. 1, 1998, pp. 2421-2434.

* cited by examiner

SINGLE-CHAIN CD40-RECEPTOR AGONIST PROTEINS

This application is a continuation of PCT/EP2016/059983, filed May 4, 2016, published Nov. 10, 2016, under PCT Article 21(2) in English; which claims the priority of U.S. Provisional Application No. 62/156,813, filed May 4, 2015. The contents of the above applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence_Listing.txt with a creation date of Oct. 25, 2017, and a size of 90.3 kilobytes. The Sequence Listing filed via EFS-Web is part of the specification and is hereby incorporated in its entirety by reference herein.

FIELD OF THE INVENTION

The present invention provides specific CD40 receptor agonist proteins comprising three soluble CD40L domains and an Fc fragment, nucleic acid molecules encoding the CD40 receptor agonist proteins, and uses thereof. The CD40 receptor agonist proteins are substantially non-aggregating and suitable for therapeutic, diagnostic and/or research applications.

BACKGROUND OF THE INVENTION

It is known that trimerization of TNF superfamily (TNFSF) cytokines is required for efficient receptor binding and activation. Trimeric complexes of TNF superfamily cytokines, however, are difficult to prepare from recombinant monomeric units.

WO 01/49866 and WO 02/09055 disclose recombinant fusion proteins comprising a TNF cytokine and a multimerization component, particularly a protein from the C1q protein family or a collectin. A disadvantage of these fusion proteins is, however, that the trimerization domain usually has a large molecular weight and/or that the trimerization is rather inefficient.

Schneider et al. (J Exp Med 187 (1988), 1205-1213) describe that trimers of TNF cytokines are stabilized by N-terminally positioned stabilization motifs. In CD95L, the stabilization of the receptor binding domain trimer is presumably caused by N-terminal amino acid domains which are located near the cytoplasmic membrane.

Shiraishi et al. (Biochem Biophys Res Commun 322 (2004), 197-202) describe that the receptor binding domain of CD95L may be stabilized by N-terminally positioned artificial α-helical coiled-coil (leucine zipper) motifs. It was found, however, that the orientation of the polypeptide chains to each other, e.g. parallel or antiparallel orientation, can hardly be predicted. Further, the optimal number of heptad-repeats in the coiled-coil zipper motif are difficult to determine. In addition, coiled-coil structures have the tendency to form macromolecular aggregates after alteration of pH and/or ionic strength.

WO 01/25277 relates to single-chain oligomeric polypeptides which bind to an extracellular ligand binding domain of a cellular receptor, wherein the polypeptide comprises at least three receptor binding sites of which at least one is capable of binding to a ligand binding domain of the cellular receptor and at least one is incapable of effectively binding to a ligand binding domain of the cellular receptor, whereby the single-chain oligomeric polypeptides are capable of binding to the receptor, but incapable of activating the receptor. For example, the monomers are derived from cytokine ligands of the TNF family, particularly from TNF-α.

WO 2005/103077 discloses single-chain fusion polypeptides comprising at least three monomers of a TNF family ligand member and at least two peptide linkers that link the monomers of the TNF ligand family members to one another. Recent experiments, however, have shown that these single-chain fusion polypeptides show undesired aggregation.

WO 2010/010051 discloses single-chain fusion polypeptides comprising three soluble TNF family cytokine domains and at least two peptide linkers. The described fusion polypeptides are substantially non-aggregating.

Recent studies have shown that the F(ab')$_2$-Fragments of the anti-CD40-mAb currently explored in the clinic, are not agonistic without further crosslinking. (see Vonderheide, R. H. and M. J. Glennie (2013). "Agonistic CD40 antibodies and cancer therapy." *Clin Cancer Res* 19(5): 1035-1043.

There is a need in the art for novel CD40 receptor agonists that exhibit high biological activity independent of Fc-gamma-R based crosslinking in vivo, high stability, and allow for efficient recombinant manufacturing.

SUMMARY OF THE INVENTION

The present invention provides specific CD40 receptor agonist proteins that mimic the CD40:CD40L interaction in vivo, exhibit low proteolytic degradation and prolong in vivo half-life.

The CD40 receptor agonist proteins of the instant invention generally comprise: (i) a first soluble CD40L cytokine domain; (ii) a first peptide linker; (iii) a second soluble CD40L domain; (iv) a second peptide linker; (v) a third soluble CD40L domain; (vi) a third peptide linker (e.g., a hinge-linker) and (vii) an antibody Fc fragment.

In one embodiment, the antibody Fc fragment (vi) is located N terminal to the first CD40L domain (i) and/or C-terminal to the third CD40L domain (v). In another embodiment the antibody Fc fragment is located C-terminally to the third CD40L domain (v). In one embodiment, the polypeptide is substantially non aggregating. In another embodiment, the second and/or third soluble CD40L domain is an N-terminally shortened domain which optionally comprises amino acid sequence mutations.

In one embodiment, at least one of the soluble CD40L domains, particularly at least one of the soluble CD40L domains (iii) and (v), is a soluble CD40L domain with an N-terminal sequence which starts at amino acid Gln121 or Ile122 of human CD40L and wherein Gln121 may be replaced by a neutral amino acid, e.g., Ser or Gly. In another embodiment, at least one of the soluble CD40L domains, particularly at least one of the soluble CD40L domains (iii) and (v), is a soluble CD40L domain with an N-terminal sequences selected from (a) Gln121-Ile122 and (b) (Gly/Ser)121-Ile122. In one embodiment, the soluble CD40L domain ends with amino acid Leu261 of human CD40L and/or optionally comprises one or more mutation at positions E129, A130, S132, K133, T134, E142, Y145, Y146, C178, C194, R200, F201, C218, Q220, N240. In one embodiment, the soluble CD40L domains (i), (iii) and (v) comprise amino acids Gln121-Leu261 of human CD40L according to SEQ ID NO: 1.

In one embodiment, the first and second peptide linkers (ii) and (iv) independently have a length of 3-8 amino acids, particularly a length of 3, 4, 5, 6, 7, or 8 amino acids, and preferably are glycine/serine linkers, optionally comprising an asparagine residue which may be glycosylated. In one embodiment, the first and the second peptide linkers (ii) and (iv) consist of the amino acid sequence according to SEQ ID NO: 2. In another embodiment, the polypeptide additionally comprises an N-terminal signal peptide domain, e.g., of SEQ ID NO: 17, which may comprise a protease cleavage site, and/or which additionally comprises a C-terminal element which may comprise and/or connect to a recognition/purification domain, e.g., a Strep-tag attached to a serine linker according to SEQ ID NO: 18.

In one embodiment, the antibody Fc fragment (vii) is fused to the soluble CD40L domain (i) and/or (v) via a hinge-linker, preferably of SEQ ID NO: 16. In another embodiment, the antibody Fc fragment (vii) consists of the amino acid sequence as shown in SEQ ID NO: 13 or 14.

In one embodiment, the single-chain fusion polypeptide of the present invention comprises the amino acid sequence selected from the group consisting of SEQ ID NO: 15, and 25-35.

In one embodiment, the present invention provides a CD40 receptor agonist protein comprising two single-chain fusion polypeptides each having the amino acid sequence set forth in SEQ ID NO: 27. In one embodiment, the two polypeptides are covalently linked through three interchain disulfide bonds formed between cysteine residues 453, 459, and 462 of each polypeptide.

In one embodiment, one or more of the asparagine residues at positions 147 and 296 of the mature polypeptide(s) SEQ ID NO: 27, 28, 29, 30, 32, or 34 are N-glycosylated. In another embodiment, the asparagine residues at positions 147 and 296 of the polypeptide(s) are both N-glycosylated.

In another embodiment, the polypeptide(s) are further post-translationally modified. In another embodiment, the post-translational modification comprises the N-terminal glutamine modified to pyroglutamate.

In another aspect, the present invention provides a pharmaceutical composition comprising a CD40 receptor agonist protein disclosed herein and one or more pharmaceutically acceptable carriers, diluents, excipients, and/or adjuvants.

In another aspect, the present invention provides a nucleic acid molecule encoding the CD40 receptor agonist protein. In another embodiment, the present invention provides an expression vector comprising the nucleic acid molecule. In another embodiment, the present invention provides a cell comprising the nucleic acid molecule. In a further embodiment, the cell is a eukaryotic cell. In another embodiment, the cell is a mammalian cell. In another embodiment, the cell is a Chinese Hamster Ovary (CHO) cell. In other embodiments, the cell is selected from the group consisting of CHO-DBX11, CHO-DG44, CHO-S, and CHO-K1 cells. In other embodiments, the cell is selected from the group consisting of Vero, BHK, HeLa, COS, MDCK, HEK-293, NIH-3T3, W138, BT483, Hs578T, HTB2, BT20, T47D, NSO, CRL7030, HsS78Bst, PER.C6, SP2/0-Agl4, and hybridoma cells.

In another aspect, the present invention provides a method of treating a subject having a CD40L-associated disease or disorder, the method comprising administering to the subject an effective amount of the CD40 receptor agonist protein. In one embodiment, the CD40 receptor agonist protein is administered alone. In another embodiment, the CD40 receptor agonist protein is administered before, concurrently, or after the administration of a second agent. In another embodiment, the disease or disorder is selected from the group consisting of: tumors, infectious diseases, inflammatory diseases, metabolic diseases, autoimmune disorders, degenerative diseases, apoptosis-associated diseases, and transplant rejections. In one embodiment, the tumors are solid tumors. In one embodiment, the tumors arise from the group of cancers consisting of sarcoma, esophageal cancer, and gastric cancer. In another embodiment, the tumors arise from Ewing's sarcoma or fibrosarcoma. In another embodiment, the tumors arise from the group of cancers consisting of Non-Small Cell Lung Carcinoma (NSCLC), pancreatic cancer, colorectal cancer, breast cancer, ovarian cancer, head and neck cancers, and Small Cell Lung Cancer (SCLC). In another embodiment, the tumors are lymphatic tumors. In one embodiment, the tumors are hematologic tumors. In another embodiment, the tumors arise from non-Hodgkin's lymphoma, leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), or hairy cell leukemia. In another embodiment, the autoimmune disorders are rheumatoid diseases, arthritic diseases, or rheumatoid and arthritic diseases. In a further embodiment, the disease or disorder is rheumatoid arthritis. In another embodiment, the degenerative disease is a neurodegenerative disease. In a further embodiment, the neurodegenerative disease is multiple sclerosis.

In one embodiment, the second agent is a chemotherapeutic, radiotherapeutic, or biological agent. In one embodiment, the second agent is selected from the group consisting of Duvelisib, Ibrutinib, Navitoclax, and Venetoclax. In another embodiment, the second agent is an apoptotic agent. In one embodiment, the apoptotic second agent is selected from the group consisting of Bortezomib, Azacitidine, Dasatinib, and Gefitinib. In a particular embodiment, the pharmaceutical compositions disclosed herein are administered to a patient by intravenous or subcutaneous administration. In other embodiments, the disclosed pharmaceutical compositions are administered to a patient byoral, parenteral, intramuscular, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal administration.

In one embodiment, the CD40 receptor agonist protein is administered as a single bolus. In another embodiment, CD40 receptor agonist protein may be administered over several divided doses. The CD40 receptor agonist protein can be administered at about 0.1-100 mg/kg. In one embodiment, the CD40 receptor agonist protein can be administered at a dosage selected from the group consisting of: about 0.1-0.5, 0.1-1, 0.1-10, 0.1-20, 0.1-50, 0.1-75, 1-10, 1-15, 1-7.5, 1.25-15, 1.25-7.5, 2.5-7.5, 2.5-15, 5-15, 5-7.5, 1-20, 1-50, 7-75, 1-100, 5-10, 5-15, 5-20, 5-25, 5-50, 5-75, 10-20, 10-50, 10-75, and 10-100 mg/kg. In other embodiments, the CD40 receptor agonist protein is present in pharmaceutical compositions at about 0.1-100 mg/ml. In one embodiment, the CD40 receptor agonist protein is present in pharmaceutical compositions at an amount selected from the group consisting of: about 0.1-0.5, 0.1-1, 0.1-10, 0.1-20, 0.1-50, 0.1-75, 1-10, 1-20, 1-50, 1-75, 1-100, 5-10, 5-15, 5-20, 5-25, 5-50, 5-75, 10-20, 10-50, 10-75, or 10-100 mg/ml. In other embodiments, a therapeutically effective amount of CD40 receptor agonist protein is administered to a subject. In another embodiment, a prophylactically effective amount of CD40 receptor agonist protein is administered to a subject.

DESCRIPTION OF THE FIGURES

FIG. 9 2 ml of blood were incubated with 1 µg/ml PROTEIN X (b), 50 µg/ml PROTEIN X (c), 1 µg/ml PROTEIN A (d), or 50 µg/ml PROTEIN A (e). The percentage of CD83-positive cells was determined and normalized to the control sample (a), which was not incubated with a CD40 receptor agonist.

DETAILED DESCRIPTION OF THE INVENTION

The inventors have discovered that fusing a single-chain CD40L receptor-binding domain to an antibody derived dimerization domain results in a hexavalent CD40 receptor agonist providing high biological activity combined with good stability. Accordingly, a single-chain fusion polypeptide comprising at least three soluble CD40L domains connected by two peptide linkers and N-terminally and/or C-terminally an antibody-derived dimerization domain, is provided.

Preferably, the single-chain fusion polypeptide is non-aggregating. The term "non-aggregating" refers to a monomer content of the preparation of 50%, preferably 70% and more preferably 90%. The ratio of monomer content to aggregate content may be determined by examining the amount of aggregate formation using size-exclusion chromatography (SEC). The stability concerning aggregation may be determined by SEC after defined time periods, e.g. from a few to several days, to weeks and months under different storage conditions, e.g. at 4° C. or 25° C. For the fusion protein, in order to be classified as substantially non-aggregating, it is preferred that the "monomer" content is as defined above after a time period of several days, e.g. 10 days, more preferably after several weeks, e.g. 2, 3 or 4 weeks, and most preferably after several months, e.g. 2 or 3 months of storage at 4° C., or 25° C. With regard to the definition of "monomer" in the case of FC-fusion proteins, the assembly of two polypeptide chains is driven by the FC-part and the functional unit of the resulting assembled protein consists of two chains. This unit is defined as "monomer" in the case of Fc-fusion proteins regardless of being a dimerized single-chain fusion polypeptide.

The single-chain fusion polypeptide may comprise additional domains which may be located at the N- and/or C-termini thereof. Examples for additional fusion domains are e.g. an N-terminal signal peptide domain which may comprise a protease cleave site or a C-terminal element which may comprise and/or connect to a recognition/purification domain. According to a preferred embodiment, the fusion polypeptide comprises a Strep-tag at its C-terminus that is fused via a linker. An exemplary Strep-tag including a short serine linker is shown in SEQ ID NO: 18.

The CD40 receptor agonist protein of the present invention comprises three soluble domains derived from CD40L. Preferably, those soluble domains are derived from a mammalian, particularly human CD40L including allelic variants and/or derivatives thereof. The soluble domains comprise the extracellular portion of CD40L including the receptor binding domain without membrane located domains. Like other proteins of the TNF superfamily, CD40L is anchored to the membrane via an N-terminal portion of 15-30 amino acids, the so-called stalk-region. The stalk region contributes to trimerization and provides a certain distance to the cell membrane. However, the stalk region is not part of the receptor binding domain (RBD).

Figure 1:
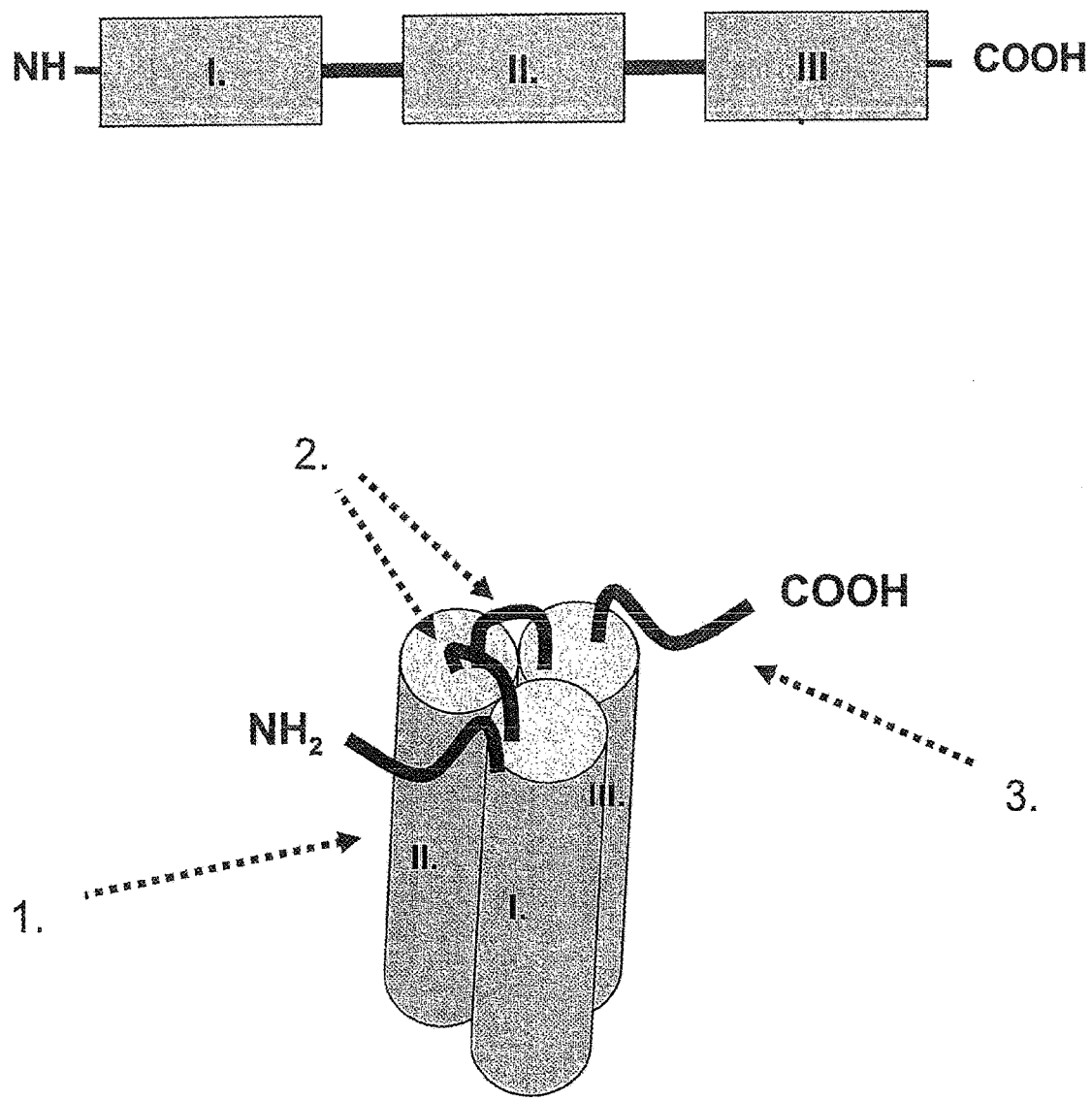
FIG. 1 Domain structure of a single-chain fusion polypeptide comprising three CD40L domains. I., II., III. Soluble CD40L domains.
Figure 2:
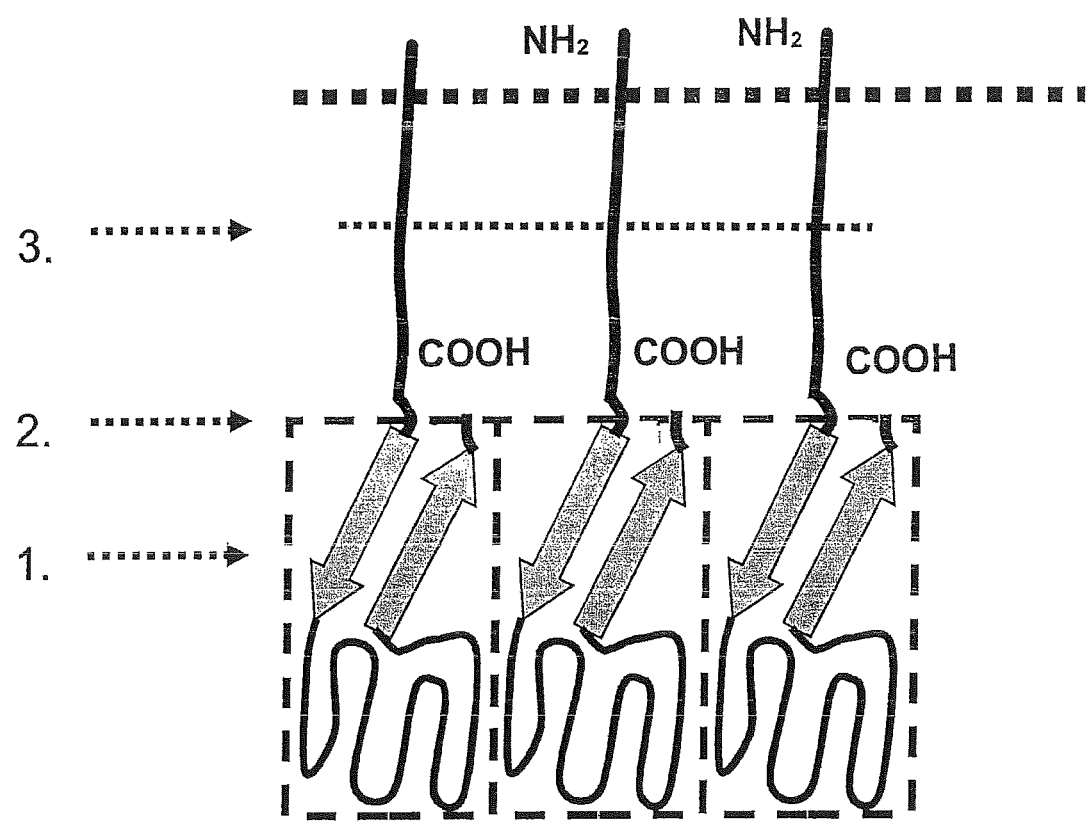
FIG. 2 Schematic picture representing the general structure of CD40L.
■ ■ ■ Cell membrane, N-terminus located within the cell,
1. anti-parallel β-fold of receptor-binding domain (RBD),
2. interface of RBD and cell membrane,
3. protease cleavage site.
Figure 3:
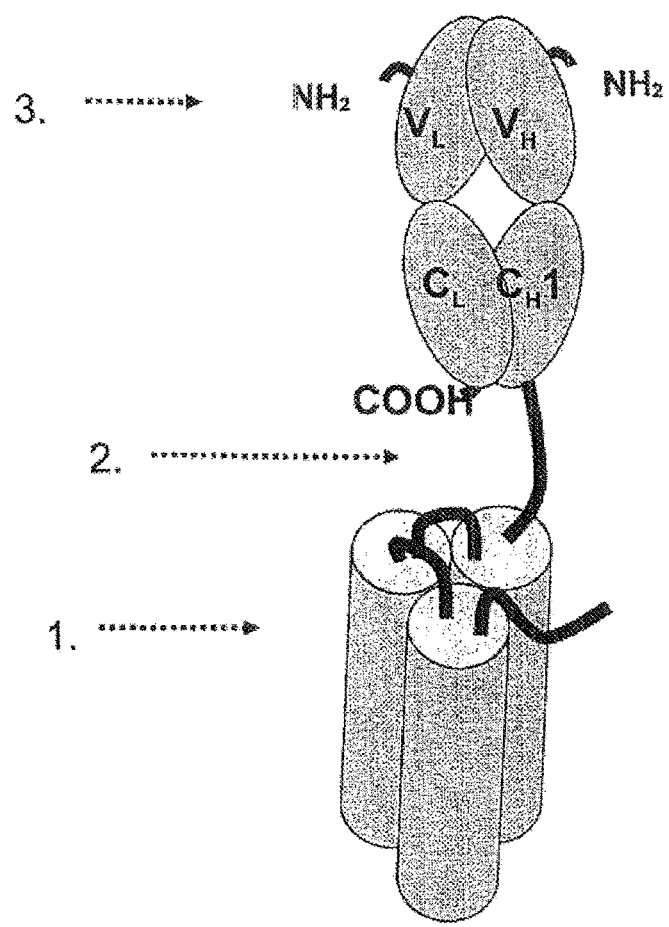
FIG. 3 Single-chain fusion polypeptide comprising an additional Fab antibody fragment.
Figure 4:
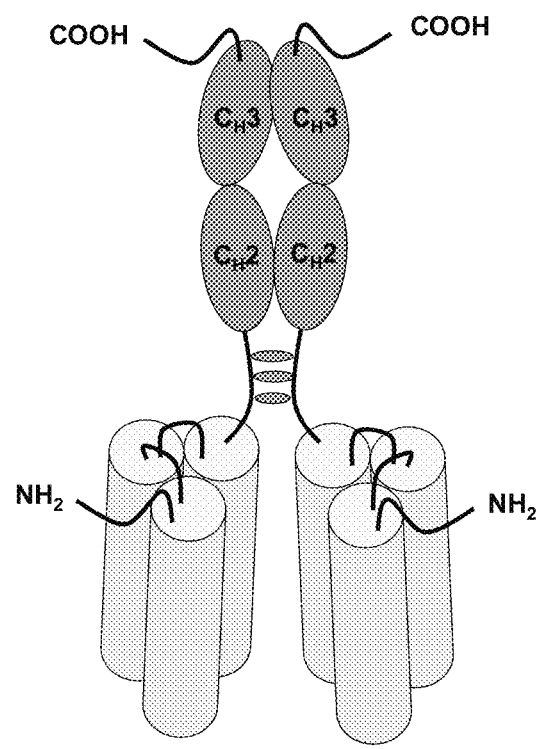
FIG. 4 Dimerization of two C-terminally fused scFc fusion polypeptides via three disulfide bridges.

Importantly, the RBD is characterized by a particular localization of its N- and C-terminal amino acids. Said amino acids are immediately adjacent and are located centrally to the axis of the trimer. The first N-terminal amino acids of the RBD form an anti-parallel beta-strand with the C-terminal amino acids of the RBD (FIG. 2).

Thus, the anti-parallel beta-strand of the RBD forms an interface with the cell membrane, which is connected to and anchored within the cell membrane via the amino acids of the stalk region. It is highly preferred that the soluble CD40L domains of the CD40 receptor agonist protein comprise a receptor binding domain of the CD40L lacking any amino acids from the stalk region. Otherwise, a long linker connecting the C-terminus of one of the soluble domains with the N-terminus of the next soluble domain would be required to compensate for the N-terminal stalk-region of the next soluble domain, which might result in instability and/or formation of aggregates.

A further advantage of such soluble domains is that the N- and C-terminal amino acids of the RBD are not accessible for any anti-drug antibodies. Preferably, the single-chain fusion polypeptide is capable of forming an ordered trimeric structure comprising at least one functional binding site for the respective CD40L receptor.

The CD40 receptor agonist protein comprises three functional CD40 receptor binding sites, i.e. amino acid sequences capable of forming a complex with a CD40 receptor. Thus, the soluble domains are capable of binding to the corresponding CD40 receptor. In one embodiment, at least one of the soluble domains is capable of receptor activation, whereby apoptotic and/or proliferative activity may be affected. In a further embodiment, one or more of the soluble domains are selected as not being capable of receptor activation.

The soluble CD40L domain may be derived from human CD40L as shown in SEQ ID NO: 1. Preferably, the soluble CD40L domains are derived from human CD40L, particularly starting from amino acids 121 or 122 and comprise particularly amino acids 121-261 or 122-261 of SEQ ID NO: 1. Optionally, amino acid Gln121 of SEQ ID NO: 1 may be replaced by a non-charged amino acid, e.g. Ser or Gly.

TABLE 1

Sequence of Wild-Type Human CD40L Protein

| SEQ ID NO | Sequence |
|---|---|
| 1 | MIETYNQTSPRSAATGLPISMKIFMYLLTVFLITQMIG SALFAVYLHRRLDKIEDERNLHEDFVFMKTIQRCNTGE RSLSLLNCEEIKSQFEGFVKDIMLNKEETKKENSFEMQ KGDQNPQIAAHVISEASSKTTSVLQWAEKGYYTMSNNL VTLENGKQLTVKRQGLYYIYAQVTFCSNREASSQAPFI ASLCLKSPGRFERILLRAANTHSSAKPCGQQSIHLGGV FELQPGASVFVNVTDPSQVSHGTGFTSFGLLKL |

As indicated above, the soluble CD40L domains may comprise the wild-type sequences as indicated in SEQ ID NO: 1. It should be noted, however, that it is possible to introduce mutations in one or more of these soluble domains, e.g. mutations which alter (e.g. increase or decrease) the binding properties of the soluble domains. In one embodiment, soluble domains that cannot bind to the corresponding cytokine receptor can be selected.

In a further embodiment of the invention, the soluble CD40L domain (i) comprises a mutant of CD40L or a receptor binding domain thereof resulting in reduced affinity and/or reduced activation of CD40 receptor.

The binding and/or activity of the mutant may be determined, e.g., by the assays as described in An et al. (2011, J Biol Chem 286(13): 11226-11235); Singh et al. (1998, Protein Sci 7(5): 1124-1135); Kim et al, J Biol Chem 286(13): 11226-11235; or Singh et al (1998). Protein Sci 7(5): 1124-1135.

The mutant may be generated by any technique and is known by the skilled person. The substitution may affect at least one amino acid of CD40L, e.g., human CD40L (e.g., SEQ ID NO: 1) or a receptor binding domain thereof as described herein. Preferred substitutions in this regard affect at least one of the following amino acids of human CD40L of SEQ ID NO: 1: E129, S132, T134, E142, Y145, Y146, R200, F201, Q220, such as E129G, S132E, S132N, T134E, T134N, E142G, E142S, Y145S, Y146S, R200S, Q220E, and Q220S; in particularly E129G and E142G.

The amino acid substitution(s) may affect the binding and/or activity of CD40L, e.g., human CD40L, to or on either the CD40 binding or the CD40 induced signaling. The binding and/or activity of the CD40 may be affected positively, i.e., stronger, more selective or more specific binding and/or more activation of the receptor. Alternatively, the binding and/or activity of the CD40 may be affected negatively, i.e., weaker, less selective or less specific binding and/or less or no activation of the receptor.

Examples of mutants of CD40L with amino acid substitution(s) of the invention that affect binding and/or activation of CD40 may be found, e.g., in FIG. 1 of An et al. (cf. above).

Thus one embodiment is a CD40 receptor agonist protein as described herein wherein at least one of the soluble domains comprises a mutant of CD40L or a receptor binding domain thereof which binds and/or activates CD40 to a lesser extent than the wildtype-CD40L.

Further examples of mutants of CD40L, which show reduced CD40L induced receptor aggregation/and or reduced signaling are S132E, and T134E.

One embodiment is a CD40 receptor agonist protein as described herein, wherein at least one artificial N-glycosylation consensus site is introduced into the sequence area defined by E129-5136 resulting in reduced receptor aggregation/and or reduced signaling. Examples of mutants of CD40L resulting in an artificial N-glycosylation consensus site in this region are E129N, A130N, S132N, K133N and T134N.

In a further embodiment of the invention, one or more of the soluble CD40L domains (i), (iii), and (v) may comprise a mutant of CD40L or a receptor binding domain thereof resulting in reduced self-aggregation and/or prolonged in vivo stability. Preferred substitutions in this regard affect at least one of the following amino acids of human CD40L of SEQ ID NO: 1: C178, C194, C218, N240; such as C178 (A,S,G); C194(A,S,G), F201 (G,S,T, D), C218(A,S,G) and N240(E,S,D,T). The mutation(s) of each CD40L domain may be the same or different.

The single-chain fusion molecule of the present invention comprises three soluble CD40L domains, namely components (i), (iii) and (v). The stability of a single-chain CD40L fusion polypeptide against aggregation is enhanced, if the second and/or third soluble CD40L domain is an N-terminally shortened domain which optionally comprises amino acid sequence mutations. Thus, preferably, both the second and the third soluble CD40L domain are N-terminally shortened domains which optionally comprise amino acid sequence mutations in the N-terminal regions, preferably within the first five amino acids of the N-terminus of the soluble CD40L domain. These mutations may comprise replacement of basic amino acids, by neutral amino acids, particularly serine or glycine. In contrast thereto, the selection of the first soluble CD40L domain is not as critical. Here, a soluble domain having a full-length N-terminal sequence may be used. It should be noted, however, that also the first soluble CD40L domain may have an N-terminally shortened and optionally mutated sequence.

In a further preferred embodiment of the present invention, the soluble CD40L domains (i), (iii) and (v) are soluble human CD40L domains. The first soluble CD40L domain (i) may be selected from native, shortened and/or mutated sequences. Thus, the first soluble CD40L domain (i) has an N-terminal sequence which may start at amino acid Gln121 or Ile122 of human CD40L, and wherein Gln121 may be replaced by a neutral amino acid, e.g. by Ser or Gly. The second and third soluble CD40L domains (iii) and (v) have a shortened N-terminal sequence which preferably starts with amino acid Gln120 or Ile122 of human CD40L and wherein Gln121 may be replaced by another amino acid, e.g. Ser or Gly.

Preferably, the N-terminal sequence of the soluble CD40L domains (iii) and (v) is selected from:
(a) Gln121 or Ile122
(b) (Gly/Ser) 121.

The soluble CD40L domain preferably ends with amino acid Leu261 of human CD40L. In certain embodiments, the CD40L domain may comprise internal mutations as described above.

Components (ii) and (iv) of the CD40 receptor agonist protein are peptide linker elements located between components (i) and (iii) or (iii) and (v), respectively. The flexible linker elements have a length of 3-8 amino acids, particularly a length of 3, 4, 5, 6, 7, or 8 amino acids. The linker elements are preferably glycine/serine linkers, i.e. peptide linkers substantially consisting of the amino acids glycine and serine. In cases in which the soluble cytokine domain starts with S or G (N-terminus), the linker ends before this S or G.

It should be noted that linker (ii) and linker (iv) do not need to be of the same length. In order to decrease potential immunogenicity, it may be preferred to use shorter linkers. In addition it turned out that shorter linkers lead to single chain molecules with reduced tendency to form aggregates. Whereas linkers that are substantially longer than the ones disclosed here may exhibit unfavorable aggregations properties.

If desired, the linker may comprise an asparagine residue which may form a glycosylate site Asn-Xaa-Ser. In certain embodiments, one of the linkers, e.g. linker (ii) or linker (iv) comprises a glycosylation site. In other embodiments, both linkers (iv) comprise glycosylation sites. In order to increase the solubility of the CD40L agonist proteins and/or in order to reduce the potential immunogenicity, it may be preferred that linker (ii) or linker (iv) or both comprise a glycosylation site.

Preferred linker sequences are shown in Table 2. A preferred linker is GSGSGNGS (SEQ ID NO: 2).

TABLE 2

Example Linker Sequences

| SEQ ID NO | Sequence |
|---|---|
| 2 | GSGSGNGS |
| 3 | GSGSGSGS |
| 4 | GGSGSGSG |
| 5 | GGSGSG |
| 6 | GGSG |
| 7 | GGSGNGSG |
| 8 | GGNGSGSG |
| 9 | GGNGSG |
| 10 | GSGSGS |
| 11 | GSGS |
| 12 | GSG |

The CD40 receptor agonist protein additionally comprises an antibody Fc fragment domain which may be located N-terminal to the first CD40L domain (i) and/or C-terminal to the third CD40L domain (v). Preferably, the antibody Fc fragment domain comprises a reduced capability to interact with Fc-gamma-R receptors in vivo. Preferably, the antibody Fc fragment domain comprises or consists of an amino acid sequence as shown in SEQ ID NO: 13 or 14. Example Fc fragment domains are shown in Table 3.

TABLE 3

Examples of Fc Fragment Domains

| SEQ ID NO | Sequence |
|---|---|
| 13 | PAPELLGGPSVFLFPPKPKDTLMISRTPEVTCVVVDV SHEDPEVKFNWYVDGVEVHNAKTKPREEQYSSTYRVV SVLTVLHQDWLNGKEYKCKVSNKALPAPIEKTISKAK GQPREPQVYTLPPSREEMTKNQVSLTCLVKGFYPSDI AVEWESNGQPENNYKTTPPVLDSDGSFFLYSKLTVDK SRWQQGNVFSCSVMHEALHNHYTQKSLSLSPGK |
| 14 | PAPPVAGPSVFLFPPKPKDTLMISRTPEVTCVVVDVS HEDPEVKFNWYVDGVEVHNAKTKPREEQYNSTYRVVS VLTVLHQDWLNGKEYKCKVSNKGLPSSIEKTISKAKG QPREPQVYTLPPSREEMTKNQVSLTCLVKGFYPSDIA VEWESNGQPENNYKTTPPVLDSDGSFFLYSKLTVDKS RWQQGNVFSCSVMHEALHNHYTQKSLSLSPGK |

The total number of glycosites and the individual position of the carbohydrates in three dimensions impacts the in-vivo stability of CD40 receptor agonist proteins. Further, carbohydrate recognition depends on local density of the terminal saccharides, the branching of the carbohydrate tree and the relative position of the carbohydrates matter.

Depletion of CH2-domain carbohydrates is necessary in order to avoid Fc-receptor based crosslinking in vivo and potential CD40L-receptor superclustering-based toxicity. Further, partially degraded carbohydrates reduce the in vivo half-life of CD40 receptor agonist proteins through lectin-driven mechanisms. By reducing the total number of glycosylation sites on the molecule, the resulting compound is less accessible to these mechanisms, increasing half-life. Accordingly, in one embodiment, the overall number of glycosites on the CD40 receptor agonist proteins of the instant invention was reduced through the depletion of CH2 glycosites, resulting in CD40 receptor agonist proteins comprising N297S equivalent mutations of SEQ ID NO: 15 (PROTEIN A) (according to the EU numbering system) creating aglycosl-CH2 domains.

Figure 10:
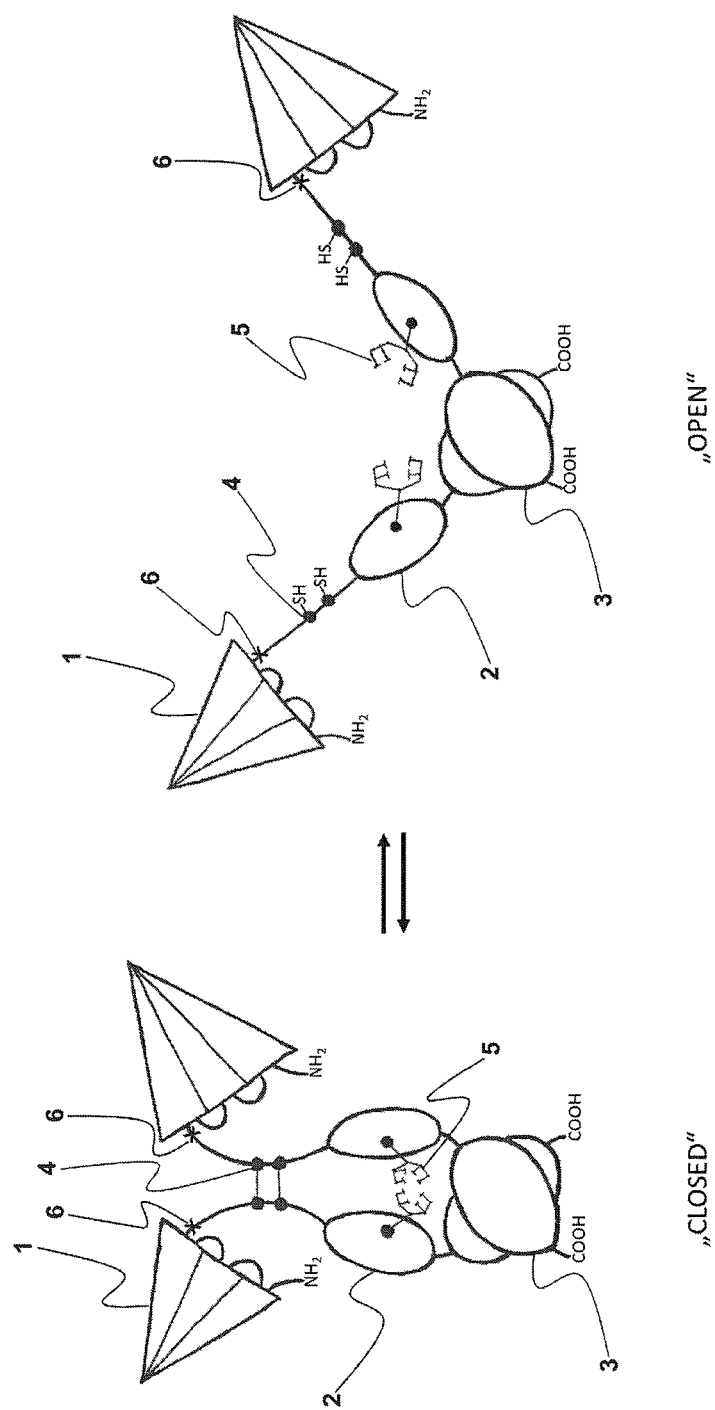
FIG. 10 Schematic representation of the hexavalent single chain CD40 receptor agonist fusion protein of the invention. CH2-Carbohydrates (5) present on the inner surface areas normally shield the CH2-subdomain sterically (2) from proteases during "open Fc-conformation transits" wherein hinge-interchain disulfide bonds (4) are reduced and the covalent interchain linkage is disrupted. This enables CH2-dissociation and exposure of the inner surface areas and the upper hinge lysine K223 (6) towards proteases. Dimer association in the "open stage" remains intact due to the high affinity of the CH3 domains (3) to each other. (1) scCD40L-RBD; (2) CH2 domain; (3) CH3 domain; (4) Hinge-Cysteines (left side: oxidized to disulfide bridges; right side reduced stage with free thiols); (5) CH2-Carbohydrates attached to N297 position (EU-numbering); (6) Upper Hinge Lysine (K223)

CH2-glycosites present on the inner surface areas normally shield the subdomain from proteases during "open Fc-conformation transits" wherein hinge-interchain disulfide bonds are reduced and the covalent interchain linkage is disrupted (FIG. 10). This enables CH2-dissociation and exposure of the inner surface area towards proteases.

CD40 receptor agonist proteins comprising an N297S equivalent mutation of SEQ ID NO: 15 (PROTEIN A) (according to the EU numbering system) creating an aglycosl-CH2 are therefore likely to be less proteolytically stable that equivalent structures with wild-type CH2 glycosylation. This would impact the compound's stability during USP/DSP/storage, where host cell proteases are present and have long-term access to the structure. Accordingly, in certain embodiments, the CD40 receptor agonist lacks CH2 glycosites, but comprises glycosites in the linker sequences of each polypeptide chain (e.g., GSGSGNGS, SEQ ID NO: 2). In certain exemplary embodiments, the CD40 receptor agonist comprises five glycosites per polypeptide chain, for a total of ten glycosites in a dimer.

According to a preferred embodiment of the invention, the antibody Fc fragment domain is fused via a hinge-linker element. The hinge-linker element has a length of 10-30 amino acids, particularly a length of 15-25 amino acids, e.g. 22 amino acids. The hinge-linker element preferably comprises the hinge-region sequence of an immunoglobulin, herein referred to as "Ig hinge-region". The term "Ig hinge-region" means any polypeptide comprising an amino acid sequence that shares sequence identity or similarity with a portion of a naturally occurring Ig hinge-region sequence which includes the cysteine residues at which the disulfide bonds link the two heavy chains of the immunoglobulin.

Derivatives and analogues of the hinge-region can be obtained by mutations. A derivative or analogue as referred to herein is a polypeptide comprising an amino acid sequence that shares sequence identity or similarity with the full length sequence of the wild type (or naturally occurring protein) except that it has one or more amino acid sequence differences attributable to a deletion, insertion and/or substitution. According to the present invention, however, the term "hinge-linker" is not limited to those linkers comprising an Ig hinge-region or a derivative thereof, but any linkers long enough to allow the domains attached by the hinge-linker element to attain a biologically active confirmation.

The number of molecules with open Fc-conformation in an individual CD40 receptor agonist protein depends on the number of interchain-disulfide bonds present in the hinge region. Accordingly, in one embodiment a third cysteine was introduced into the hinge region of the CD40 receptor agonist proteins of the instant invention in order to ameliorate the effect of depleting the CH2-glycosites.

The interchain-disulfide connectivity of the hinge region stabilizing the homodimer of the hexavalent CD40 receptor agonist protein will be also affected by the free thiol groups of the CD40L subsequences (six in total per dimer). This also leads to the aforementioned open FC-conformation due to self-reduction of the hinge disulfide-bridges of the structure by the endogenous free thiols of the preparation. In consequence, single-chain CD40L-FC fusion proteins comprising six free thiols are expected to be less stable during manufacture and storage, when longtime exposure to oxygen and proteases occurs.

Therefore, to enable manufacture of a hexavalent CD40 receptor agonist, the C194 residue is preferably mutated to a different amino-acid without affecting receptor binding.

Further, the CD40 receptor agonist proteins of the invention additionally comprise mutation of the upper-hinge lysine to a glycine to reduce proteolytic processing at this site. Accordingly, in one embodiment, the CD40 receptor agonist proteins of the invention additionally comprise a mutation of the upper-hinge lysine (K223, according to the EU numbering system) to a glycine to reduce proteolytic processing at this site, thereby enhancing the overall stability of the fusion protein. Combining aforementioned introduction of a third cysteine (C225, according to the EU numbering system) with the aforementioned lysine to glycine mutation (K223G, according to the EU numbering system) within the hinge region results in an overall stabilized CD40 receptor agonist protein of the instant invention.

A particularly preferred hinge-linker element comprises or consists of the amino acid sequence as shown in SEQ ID NO: 16 (Table 4), which includes aforementioned cysteine C225 and the lysine to glycine mutation K223G.

The CD40 receptor agonist protein may additionally comprise an N-terminal signal peptide domain, which allows processing, e.g. extracellular secretion, in a suitable host cell. Preferably, the N-terminal signal peptide domain comprises a protease cleavage site, e.g. a signal peptidase cleavage site and thus may be removed after or during expression to obtain the mature protein. A particularly preferred N-terminal signal peptide domain comprises the amino acid sequence as shown in SEQ ID NO: 17 (Table 4).

Further, the CD40 receptor agonist protein may additionally comprise a C-terminal element, having a length of e.g. 1-50, preferably 10-30 amino acids which may include or connect to a recognition/purification domain, e.g. a FLAG domain, a Strep-tag or Strep-tag II domain and/or a poly-His domain. According to a particularly preferred embodiment, the fusion polypeptide comprises a Strep-tag fused to the C-terminus via a short serine linker as shown in SEQ ID NO: 18 (Table 4).

An exemplary hinge-linker element (SEQ ID NO: 16, 19-24), N-terminal signal peptide domain (SEQ ID NO: 17) and serine linker-strep tag (SEQ ID NO: 18) are shown in Table 4.

TABLE 4

Exemplary domains and linkers

| SEQ ID NO | Sequence |
| --- | --- |
| 16 | GSGSSSSSSSSGSCDKTHTCPPC |
| 17 | METDTLLVFVLLVWVPAGNG |
| 18 | SSSSSSAWSHPQFEK |
| 19 | GSGSSSSSSGSCDKTHTCPPC |
| 20 | GSGSSSSSSSGSCDKTHTCPPC |
| 21 | GSGSSSSGSCDKTHTCPPC |
| 22 | GSGSSSGSCDKTHTCPPC |
| 23 | GSGSSSGSCDKTHTCPPCGS |
| 24 | GSGSSSGSCDKTHTCPPCGSGS |

In one embodiment of the invention, the fusion polypeptide comprises three soluble CD40L domains fused by peptide linker elements of SEQ ID NO: 2. The first soluble CD40L domain (i) consists of amino acids 121-261 of human CD40L according to SEQ ID NO: 1 and the soluble CD40L domains (iii) and (v) consist of amino acids 121-261 of human CD40L according to SEQ ID NO: 1.

Additionally, the fusion polypeptide comprises an antibody Fc fragment domain according to SEQ ID NO: 13 that is fused C-terminally to the soluble CD40L domain (v) via a hinge-linker according to SEQ ID NO: 16. The inventors surprisingly found that this particular fusion polypeptide provides improved biological activity and is particularly stable. The amino acid sequence of an exemplary embodiment of a CD40 receptor agonist protein of the invention is set forth in SEQ ID NO: 27.

Further, the fusion polypeptide may comprise an N-terminal signal peptide domain e.g. according to SEQ ID NO: 17. A specific example of a CD40 receptor agonist protein of the invention is shown in SEQ ID NO: 25.

According to another preferred embodiment, the fusion polypeptide may additionally comprise a C-terminal Strep-tag that is fused to the polypeptide of the invention via a short serine linker as shown in SEQ ID NO: 18. According to this aspect of the invention, the Fc fragment preferably consists of the amino acid sequence as shown in SEQ ID NO: 13 or 14. Further, the Fc fragment may consist of a shorter Fc fragment, for example including amino acids 1-217 of SEQ ID NO: 13. Particularly preferred examples of fusion polypeptides comprising a C-terminal Strep-tag are shown in SEQ ID NO: 15 (PROTEIN A).

The exemplary CD40 receptor agonist proteins as shown in SEQ ID NOs: 15, 25, and 26, each comprises an N-terminal signal peptide domain. The signal peptide domain includes amino acids 1-20. In each case, the mature protein starts with amino acid 21. Mature exemplary CD40 receptor agonist proteins (without a signal peptide) of the instant invention are set forth in SEQ ID NO: 27-30, 32, and 34. Exemplary CD40 receptor agonist proteins described above are shown in Table 5.

According to one embodiment of the invention, the single-chain CD40L fusion polypeptide domain comprises three soluble CD40L domains fused by peptide linker elements of SEQ ID NO: 2. The soluble CD40L domains (i), (iii) and (v) each consists of amino acids 121-261 of human CD40L according to SEQ ID NO: 1 with C194S mutation This single-chain-CD40L polypeptide comprising aforementioned CD40L 121-261 C194S muteins is shown in SEQ ID: 36, which is well suited to generate fusion proteins at either N- or C-terminal end with enhanced stability compared to wild type. In a preferred embodiment, an antibody Fc fragment domain according to SEQ ID NO: 13 is fused C-terminally to the soluble CD40L domain (v) of SEQ ID: 36 via a hinge linker according to SEQ ID NO: 16.

The CD40 receptor agonist as set forth in SEQ ID NO: 27 has a reduced total number of glycosylation sites (the N297S mutation in the CH2 region providing an aglycosylated CH2 domain), an increased number of inter-chain disulfide bonds in the hinge region, and the mutation of an upper-hinge lysine to a glycine. These alterations provide a decrease in potential degradation and CD40L receptor superclustering (along with concomitant toxicity). In some embodiments, the N-terminal glutamine is modified to pyroglutamate (Liu et al. 2011, J. Biol. Chem. 286:11211-11217).

TABLE 5

Exemplary CD40 receptor agonist Proteins

| SEQ ID NO | Sequence |
| --- | --- |
| 25 PROTEIN A without StrepTag | METDTLLVFVLLVWVPAGNGQIAAHVISEASSKTT SVLQWAEKGYYTMSNNLVTLENGKQLTVKRQGLYY IYAQVTFCSNREASSQAPFIASLCLKSPGRFERIL LRAANTHSSAKPCGQQSIHLGGVFELQPGASVFVN VTDPSQVSHGTGFTSFGLLKLGSGSGNGSQIAAHV ISEASSKTTSVLQWAEKGYYTMSNNLVTLENGKQL TVKRQGLYYIYAQVTFCSNREASSQAPFIASLCLK SPGRFERILLRAANTHSSAKPCGQQSIHLGGVFEL QPGASVFVNVTDPSQVSHGTGFTSFGLLKLGSGSG NGSQIAAHVISEASSKTTSVLQWAEKGYYTMSNNL VTLENGKQLTVKRQGLYYIYAQVTFCSNREASSQA PFIASLCLKSPGRFERILLRAANTHSSAKPCGQQS IHLGGVFELQPGASVFVNVTDPSQVSHGTGFTSFG LLKLGSGSSSSSSSSGSCDKTHTCPPCPAPELLGG PSVFLFPPKPKDTLMISRTPEVTCVVVDVSHEDPE VKFNWYVDGVEVHNAKTKPREEQYSSTYRVVSVLT VLHQDWLNGKEYKCKVSNKALPAPIEKTISKAKGQ PREPQVYTLPPSREEMTKNQVSLTCLVKGFYPSDI AVEWESNGQPENNYKTTPPVLDSDGSFFLYSKLTV DKSRWQQGNVFSCSVMHEALHNHYTQKSLSLSPGK |
| 15 PROTEIN A | METDTLLVFVLLVWVPAGNGQIAAHVISEASSKTT SVLQWAEKGYYTMSNNLVTLENGKQLTVKRQGLYY IYAQVTFCSNREASSQAPFIASLCLKSPGRFERIL LRAANTHSSAKPCGQQSIHLGGVFELQPGASVFVN VTDPSQVSHGTGFTSFGLLKLGSGSGNGSQIAAHV ISEASSKTTSVLQWAEKGYYTMSNNLVTLENGKQL |

TABLE 5-continued

Exemplary CD40 receptor agonist Proteins

| SEQ ID NO | Sequence |
| --- | --- |
| | TVKRQGLYYIYAQVTFCSNREASSQAPFIASLCLK SPGRFERILLRAANTHSSAKPCGQQSIHLGGVFEL QPGASVFVNVTDPSQVSHGTGFTSFGLLKLGSGSG NGSQIAAHVISEASSKTTSVLQWAEKGYYTMSNNL VTLENGKQLTVKRQGLYYIYAQVTFCSNREASSQA PFIASLCLKSPGRFERILLRAANTHSSAKPCGQQS IHLGGVFELQPGASVFVNVTDPSQVSHGTGFTSFG LLKLGSGSSSSSSSSGSCDKTHTCPPCPAPELLGG PSVFLFPPKPKDTLMISRTPEVTCVVVDVSHEDPE VKFNWYVDGVEVHNAKTKPREEQYSSTYRVVSVLT VLHQDWLNGKEYKCKVSNKALPAPIEKTISKAKGQ PREPQVYTLPPSREEMTKNQVSLTCLVKGFYPSDI AVEWESNGQPENNYKTTPPVLDSDGSFFLYSKLTV DKSRWQQGNVFSCSVMHEALHNHYTQKSLSLSPGS SSSSSAWSHPQFEK |
| 26 CD40L-wt + SEQ14 (FC) | METDTLLVFVLLVWVPAGNGQIAAHVISEASSKTT SVLQWAEKGYYTMSNNLVTLENGKQLTVKRQGLYY IYAQVTFCSNREASSQAPFIASLCLKSPGRFERIL LRAANTHSSAKPCGQQSIHLGGVFELQPGASVFVN VTDPSQVSHGTGFTSFGLLKLGSGSGNGSQIAAHV ISEASSKTTSVLQWAEKGYYTMSNNLVTLENGKQL TVKRQGLYYIYAQVTFCSNREASSQAPFIASLCLK SPGRFERILLRAANTHSSAKPCGQQSIHLGGVFEL QPGASVFVNVTDPSQVSHGTGFTSFGLLKLGSGSG NGSQIAAHVISEASSKTTSVLQWAEKGYYTMSNNL VTLENGKQLTVKRQGLYYIYAQVTFCSNREASSQA PFIASLCLKSPGRFERILLRAANTHSSAKPCGQQS IHLGGVFELQPGASVFVNVTDPSQVSHGTGFTSFG LLKLGSGSSSSSSSSGSCDKTHTCPPCPAPPVAGP SVFLFPPKPKDTLMISRTPEVTCVVVDVSHEDPEV KFNWYVDGVEVHNAKTKPREEQYNSTYRVVSVLTV LHQDWLNGKEYKCKVSNKGLPSSIEKTISKAKGQP REPQVYTLPPSREEMTKNQVSLTCLVKGFYPSDIA VEWESNGQPENNYKTTPPVLDSDGSFFLYSKLTVD KSRWQQGNVFSCSVMHEALHNHYTQKSLSLSPGK |
| 27 CD40L-wt + SEQ13 (FC) without SP without StrepTag | QIAAHVISEASSKTTSVLQWAEKGYYTMSNNLVTL ENGKQLTVKRQGLYYIYAQVTFCSNREASSQAPFI ASLCLKSPGRFERILLRAANTHSSAKPCGQQSIHL GGVFELQPGASVFVNVTDPSQVSHGTGFTSFGLLK LGSGSGNGSQIAAHVISEASSKTTSVLQWAEKGYY TMSNNLVTLENGKQLTVKRQGLYYIYAQVTFCSNR EASSQAPFIASLCLKSPGRFERILLRAANTHSSAK PCGQQSIHLGGVFELQPGASVFVNVTDPSQVSHGT GFTSFGLLKLGSGSGNGSQIAAHVISEASSKTTSV LQWAEKGYYTMSNNLVTLENGKQLTVKRQGLYYIY AQVTFCSNREASSQAPFIASLCLKSPGRFERILLR AANTHSSAKPCGQQSIHLGGVFELQPGASVFVNVT DPSQVSHGTGFTSFGLLKLGSGSSSSSSSSGSCDK THTCPPCPAPELLGGPSVFLFPPKPKDTLMISRTP EVTCVVVDVSHEDPEVKFNWYVDGVEVHNAKTKPR EEQYSSTYRVVSVLTVLHQDWLNGKEYKCKVSNKA LPAPIEKTISKAKGQPREPQVYTLPPSREEMTKNQ VSLTCLVKGFYPSDIAVEWESNGQPENNYKTTPPV LDSDGSFFLYSKLTVDKSRWQQGNVFSCSVMHEAL HNHYTQKSLSLSPGK |
| 28 | QIAAHVISEASSKTTSVLQWAEKGYYTMSNNLVTL ENGKQLTVKRQGLYYIYAQVTFCSNREASSQAPFI ASLCLKSPGRFERILLRAANTHSSAKPCGQQSIHL GGVFELQPGASVFVNVTDPSQVSHGTGFTSFGLLK LGSGSGNGSQIAAHVISEASSKTTSVLQWAEKGYY TMSNNLVTLENGKQLTVKRQGLYYIYAQVTFCSNR EASSQAPFIASLCLKSPGRFERILLRAANTHSSAK PCGQQSIHLGGVFELQPGASVFVNVTDPSQVSHGT GFTSFGLLKLGSGSGNGSQIAAHVISEASSKTTSV LQWAEKGYYTMSNNLVTLENGKQLTVKRQGLYYIY AQVTFCSNREASSQAPFIASLCLKSPGRFERILLR AANTHSSAKPCGQQSIHLGGVFELQPGASVFVNVT DPSQVSHGTGFTSFGLLKLGSGSSSSSSSSGSCDK THTCPPCPAPELLGGPSVFLFPPKPKDTLMISRTP EVTCVVVDVSHEDPEVKFNWYVDGVEVHNAKTKPR EEQYSSTYRVVSVLTVLHQDWLNGKEYKCKVSNKA LPAPIEKTISKAKGQPREPQVYTLPPSREEMTKNQ VSLTCLVKGFYPSDIAVEWESNGQPENNYKTTPPV |

TABLE 5-continued

Exemplary CD40 receptor agonist Proteins

| SEQ ID NO | Sequence |
|---|---|
| | LDSDGSFFLYSKLTVDKSRWQQGNVFSCSVMHEAL HNHYTQKSLSLSPGSSSSSSAWSHPQFEK |
| 29 | QIAAHVISEASSKTTSVLQWAEKGYYTMSNNLVTL ENGKQLTVKRQGLYYIYAQVTFCSNREASSQAPFI ASLCLKSPGRFERILLRAANTHSSAKPCGQQSIHL GGVFELQPGASVFVNVTDPSQVSHGTGFTSFGLLK LGSGSGNGSQIAAHVISEASSKTTSVLQWAEKGYY TMSNNLVTLENGKQLTVKRQGLYYIYAQVTFCSNR EASSQAPFIASLCLKSPGRFERILLRAANTHSSAK PCGQQSIHLGGVFELQPGASVFVNVTDPSQVSHGT GFTSFGLLKLGSGSGNGSQIAAHVISEASSKTTSV LQWAEKGYYTMSNNLVTLENGKQLTVKRQGLYYIY AQVTFCSNREASSQAPFIASLCLKSPGRFERILLR AANTHSSAKPCGQQSIHLGGVFELQPGASVFVNVT DPSQVSHGTGFTSFGLLKLGSGSSSSSSSGSCDK THTCPPCPAPPVAGPSVFLFPPKPKDTLMISRTPE VTCVVVDVSHEDPEVKFNWYVDGVEVHNAKTKPRE EQYNSTYRVVSVLTVLHQDWLNGKEYKCKVSNKGL PSSIEKTISKAKGQPREPQVYTLPPSREEMTKNQV SLTCLVKGFYPSDIAVEWESNGQPENNYKTTPPVL DSDGSFFLYSKLTVDKSRWQQGNVFSCSVMHEALH NHYTQKSLSLSPGK |
| 30 | QIAAHVISEASSKTTSVLQWAEKGYYTMSNNLVTL ENGKQLTVKRQGLYYIYAQVTFCSNREASSQAPFI ASLCLKSPGRFERILLRAANTHSSAKPCGQQSIHL GGVFELQPGASVFVNVTDPSQVSHGTGFTSFGLLK LGSGSGNGSQIAAHVISEASSKTTSVLQWAEKGYY TMSNNLVTLENGKQLTVKRQGLYYIYAQVTFCSNR EASSQAPFIASLCLKSPGRFERILLRAANTHSSAK PCGQQSIHLGGVFELQPGASVFVNVTDPSQVSHGT GFTSFGLLKLGSGSGNGSQIAAHVISEASSKTTSV LQWAEKGYYTMSNNLVTLENGKQLTVKRQGLYYIY AQVTFCSNREASSQAPFIASLCLKSPGRFERILLR AANTHSSAKPCGQQSIHLGGVFELQPGASVFVNVT DPSQVSHGTGFTSFGLLKLGSGSSSSSSSGSCDK THTCPPCPAPPVAGPSVFLFPPKPKDTLMISRTPE VTCVVVDVSHEDPEVKFNWYVDGVEVHNAKTKPRE EQYNSTYRVVSVLTVLHQDWLNGKEYKCKVSNKGL PSSIEKTISKAKGQPREPQVYTLPPSREEMTKNQV SLTCLVKGFYPSDIAVEWESNGQPENNYKTTPPVL DSDGSFFLYSKLTVDKSRWQQGNVFSCSVMHEALH NHYTQKSLSLSPGSSSSSSAWSHPQFEK |
| 31 PROTEIN B | METDTLLVFVLLVWVPAGNGQIAAHVISEASSKTT SVLQWAEKGYYTMSNNLVTLENGKQLTVKRQGLYY IYAQVTFCSNREASSQAPFIASLSLKSPGRFERIL LRAANTHSSAKPCGQQSIHLGGVFELQPGASVFVN VTDPSQVSHGTGFTSFGLLKLGSGSGNGSQIAAHV ISEASSKTTSVLQWAEKGYYTMSNNLVTLENGKQL TVKRQGLYYIYAQVTFCSNREASSQAPFIASLSLK SPGRFERILLRAANTHSSAKPCGQQSIHLGGVFEL QPGASVFVNVTDPSQVSHGTGFTSFGLLKLGSGSG NGSQIAAHVISEASSKTTSVLQWAEKGYYTMSNNL VTLENGKQLTVKRQGLYYIYAQVTFCSNREASSQA PFIASLSLKSPGRFERILLRAANTHSSAKPCGQQS IHLGGVFELQPGASVFVNVTDPSQVSHGTGFTSFG LLKLGSGSSSSSSSGSCDKTHTCPPCPAPELLGG PSVFLFPPKPKDTLMISRTPEVTCVVVDVSHEDPE VKFNWYVDGVEVHNAKTKPREEQYSSTYRVVSVLT VLHQDWLNGKEYKCKVSNKALPAPIEKTISKAKGQ PREPQVYTLPPSREEMTKNQVSLTCLVKGFYPSDI AVEWESNGQPENNYKTTPPVLDSDGSFFLYSKLTV DKSRWQQGNVFSCSVMHEALHNHYTQKSLSLSPGS SSSSSAWSHPQFEK |
| 32 PROTEIN B without SP | QIAAHVISEASSKTTSVLQWAEKGYYTMSNNLVTL ENGKQLTVKRQGLYYIYAQVTFCSNREASSQAPFI ASLSLKSPGRFERILLRAANTHSSAKPCGQQSIHL GGVFELQPGASVFVNVTDPSQVSHGTGFTSFGLLK LGSGSGNGSQIAAHVISEASSKTTSVLQWAEKGYY TMSNNLVTLENGKQLTVKRQGLYYIYAQVTFCSNR EASSQAPFIASLSLKSPGRFERILLRAANTHSSAK PCGQQSIHLGGVFELQPGASVFVNVTDPSQVSHGT GFTSFGLLKLGSGSGNGSQIAAHVISEASSKTTSV LQWAEKGYYTMSNNLVTLENGKQLTVKRQGLYYIY AQVTFCSNREASSQAPFIASLSLKSPGRFERILLR AANTHSSAKPCGQQSIHLGGVFELQPGASVFVNVT DPSQVSHGTGFTSFGLLKLGSGSSSSSSSGSCDK THTCPPCPAPELLGGPSVFLFPPKPKDTLMISRTP EVTCVVVDVSHEDPEVKFNWYVDGVEVHNAKTKPR EEQYSSTYRVVSVLTVLHQDWLNGKEYKCKVSNKA LPAPIEKTISKAKGQPREPQVYTLPPSREEMTKNQ VSLTCLVKGFYPSDIAVEWESNGQPENNYKTTPPV LDSDGSFFLYSKLTVDKSRWQQGNVFSCSVMHEAL HNHYTQKSLSLSPGSSSSSSAWSHPQFEK |
| 33 PROTEIN B without StrepTag | METDTLLVFVLLVWVPAGNGQIAAHVISEASSKTT SVLQWAEKGYYTMSNNLVTLENGKQLTVKRQGLYY IYAQVTFCSNREASSQAPFIASLSLKSPGRFERIL LRAANTHSSAKPCGQQSIHLGGVFELQPGASVFVN VTDPSQVSHGTGFTSFGLLKLGSGSGNGSQIAAHV ISEASSKTTSVLQWAEKGYYTMSNNLVTLENGKQL TVKRQGLYYIYAQVTFCSNREASSQAPFIASLSLK SPGRFERILLRAANTHSSAKPCGQQSIHLGGVFEL QPGASVFVNVTDPSQVSHGTGFTSFGLLKLGSGSG NGSQIAAHVISEASSKTTSVLQWAEKGYYTMSNNL VTLENGKQLTVKRQGLYYIYAQVTFCSNREASSQA PFIASLSLKSPGRFERILLRAANTHSSAKPCGQQS IHLGGVFELQPGASVFVNVTDPSQVSHGTGFTSFG LLKLGSGSSSSSSSGSCDKTHTCPPCPAPELLGG PSVFLFPPKPKDTLMISRTPEVTCVVVDVSHEDPE VKFNWYVDGVEVHNAKTKPREEQYSSTYRVVSVLT VLHQDWLNGKEYKCKVSNKALPAPIEKTISKAKGQ PREPQVYTLPPSREEMTKNQVSLTCLVKGFYPSDI AVEWESNGQPENNYKTTPPVLDSDGSFFLYSKLTV DKSRWQQGNVFSCSVMHEALHNHYTQKSLSLSPGK |
| 34 PROTEIN B without SP without StrepTag | QIAAHVISEASSKTTSVLQWAEKGYYTMSNNLVTL ENGKQLTVKRQGLYYIYAQVTFCSNREASSQAPFI ASLSLKSPGRFERILLRAANTHSSAKPCGQQSIHL GGVFELQPGASVFVNVTDPSQVSHGTGFTSFGLLK LGSGSGNGSQIAAHVISEASSKTTSVLQWAEKGYY TMSNNLVTLENGKQLTVKRQGLYYIYAQVTFCSNR EASSQAPFIASLSLKSPGRFERILLRAANTHSSAK PCGQQSIHLGGVFELQPGASVFVNVTDPSQVSHGT GFTSFGLLKLGSGSGNGSQIAAHVISEASSKTTSV LQWAEKGYYTMSNNLVTLENGKQLTVKRQGLYYIY AQVTFCSNREASSQAPFIASLSLKSPGRFERILLR AANTHSSAKPCGQQSIHLGGVFELQPGASVFVNVT DPSQVSHGTGFTSFGLLKLGSGSSSSSSSGSCDK THTCPPCPAPELLGGPSVFLFPPKPKDTLMISRTP EVTCVVVDVSHEDPEVKFNWYVDGVEVHNAKTKPR EEQYSSTYRVVSVLTVLHQDWLNGKEYKCKVSNKA LPAPIEKTISKAKGQPREPQVYTLPPSREEMTKNQ VSLTCLVKGFYPSDIAVEWESNGQPENNYKTTPPV LDSDGSFFLYSKLTVDKSRWQQGNVFSCSVMHEAL HNHYTQKSLSLSPGK |
| 35 PROTEIN C | METDTLLVFVLLVWVPAGNGQIAAHVISEASSKTT SVLQWAEKGYYTMSNNLVTLENGKQLTVKRQGLYY IYAQVTFCSNREASSQAPFIASLALKSPGRFERIL LRAANTHSSAKPCGQQSIHLGGVFELQPGASVFVN VTDPSQVSHGTGFTSFGLLKLGSGSGNGSQIAAHV ISEASSKTTSVLQWAEKGYYTMSNNLVTLENGKQL TVKRQGLYYIYAQVTFCSNREASSQAPFIASLALK SPGRFERILLRAANTHSSAKPCGQQSIHLGGVFEL QPGASVFVNVTDPSQVSHGTGFTSFGLLKLGSGSG NGSQIAAHVISEASSKTTSVLQWAEKGYYTMSNNL VTLENGKQLTVKRQGLYYIYAQVTFCSNREASSQA PFIASLALKSPGRFERILLRAANTHSSAKPCGQQS IHLGGVFELQPGASVFVNVTDPSQVSHGTGFTSFG LLKLGSGSSSSSSSGSCDKTHTCPPCPAPELLGG PSVFLFPPKPKDTLMISRTPEVTCVVVDVSHEDPE VKFNWYVDGVEVHNAKTKPREEQYSSTYRVVSVLT VLHQDWLNGKEYKCKVSNKALPAPIEKTISKAKGQ PREPQVYTLPPSREEMTKNQVSLTCLVKGFYPSDI AVEWESNGQPENNYKTTPPVLDSDGSFFLYSKLTV DKSRWQQGNVFSCSVMHEALHNHYTQKSLSLSPGS SSSSSAWSHPQFEK |

TABLE 5-continued

Exemplary CD40 receptor agonist Proteins

| SEQ ID NO | Sequence |
|---|---|
| 36 | QIAAHVISEASSKTTSVLQWAEKGYYTMSNNLVTL<br>ENGKQLTVKRQGLYYIYAQVTFCSNREASSQAPFI<br>ASLSLKSPGRFERILLRAANTHSSAKPCGQQSIHL<br>GGVFELQPGASVFVNVTDPSQVSHGTGFTSFGLLK<br>LGSGSGNGSQIAAHVISEASSKTTSVLQWAEKGYY<br>TMSNNLVTLENGKQLTVKRQGLYYIYAQVTFCSNR<br>EASSQAPFIASLSLKSPGRFERILLRAANTHSSAK<br>PCGQQSIHLGGVFELQPGASVFVNVTDPSQVSHGT<br>GFTSFGLLKLGSGSGNGSQIAAHVISEASSKTTSV<br>LQWAEKGYYTMSNNLVTLENGKQLTVKRQGLYYIY<br>AQVTFCSNREASSQAPFIASLSLKSPGRFERILLR<br>AANTHSSAKPCGQQSIHLGGVFELQPGASVFVNVT<br>DPSQVSHGTGFTSFGLLKL |

A further aspect of the present invention relates to a nucleic acid molecule encoding a CD40 receptor agonist protein as described herein. The nucleic acid molecule may be a DNA molecule, e.g. a double-stranded or single-stranded DNA molecule, or an RNA molecule. The nucleic acid molecule may encode the CD40 receptor agonist protein or a precursor thereof, e.g. a pro- or pre-proform of the CD40 receptor agonist protein which may comprise a signal sequence or other heterologous amino acid portions for secretion or purification which are preferably located at the N- and/or C-terminus of the CD40 receptor agonist protein. The heterologous amino acid portions may be linked to the first and/or second domain via a protease cleavage site, e.g. a Factor X3, thrombin or IgA protease cleavage site. A specific example of a nucleic acid sequence of the invention is shown in Table 6 as SEQ ID NO: 37. This nucleic acid molecule encodes the fusion polypeptide of SEQ ID NO: 25.

TABLE 6

Nucleic Acid Sequence of
Exemplary CD40 receptor agonist Protein

| SEQ ID NO | Sequence |
|---|---|
| 37 | AAGCTTTAGGGATAACAGGGTAATAGCCGCCACCATGGAGACT<br>GACACCCTGCTGGTGTTCGTGCTGCTGGTCTGGGTGCCTGCAG<br>GAAATGGACAGATCGCAGCTCATGTGATAAGTGAGGCAAGCTC<br>GAAGACGACTAGCGTATTGCAGTGGGCAGAGAAGGGGTACTAC<br>ACCATGTCCAACAACCTCGTCACGCTGGAGAACGGCAAACAGC<br>TCACCGTCAAGCGACAGGGCCTGTACTACATCTACGCACAAGT<br>CACCTTCTGTTCTAACCGAGAGGCTTCCAGTCAAGCACCCTTCA<br>TTGCTTCCCTGTGCCTGAAATCCCCTGGTCGATTCGAGAGGATA<br>CTGCTCAGGGCAGCTAACACTCACTCCAGTGCTAAGCCTTGCG<br>GTCAGCAGAGTATCCACCTCGGCGGCGTATTCGAGCTGCAACC<br>AGGAGCTTCCGTCTTTGTGAACGTGACTGACCCTTCTCAAGTCT<br>CTCACGGAACAGGATTCACCTCTTTCGGGCTCCTAAAGCTGGG<br>TTCCGGAAGCGGTAATGGTAGTCAAATCGCTGCCCATGTAATTT<br>CCGAGGCTTCGTCAAAGACTACGTCTGTTCTACAATGGGCCGA<br>GAAAGGCTACTATACCATGTCAAATAATCTCGTCACTCTTGAGA<br>ACGGGAAGCAGCTTACCGTTAAACGTCAGGGACTTTACTACATT<br>TATGCCCAAGTCACTTTCTGCTCAAATCGAGAGGCAAGCTCCCA<br>AGCACCGTTCATAGCATCACTCTGCCTCAAGTCCCCTGGAAGG<br>TTTGAACGAATACTACTTAGGGCCGCTAATACACATTCGAGTGC<br>AAAGCCTTGCGGACAGCAAAGCATTCATTTAGGTGGAGTCTTCG<br>AGCTTCAACCAGGAGCCTCTGTATTCGTCAACGTAACGGACCC<br>ATCGCAAGTATCCCACGGCACTGGTTTCACCTCATTCGGTTTGC<br>TGAAGTTAGGAAGCGGCAGTGGAAACGGTTCCCAAATAGCTGC<br>CCATGTCATCTCGGAAGCCTCAAGCAAGACGACAAGTGTCTTG<br>CAATGGGCCGAAAAGGGTTATTATACTATGTCTAATAACCTAGT<br>GACCCTAGAGAACGGTAAACAACTTACTGTTAAGCGCCAGGGA<br>CTTTATTATATATATGCTCAGGTAACATTCTGCTCGAATCGGGA<br>AGCATCTTCACAGGCTCCTTTTATCGCTAGTTTATGTCTGAAGA<br>GCCCCGGACGATTTGAGAGGATATTGCTTAGAGCCGCGAATACA<br>CACAGTTCAGCCAAACCTTGTGGACAACAGAGTATTCACTTAGG |

TABLE 6-continued

Nucleic Acid Sequence of
Exemplary CD40 receptor agonist Protein

| SEQ ID NO | Sequence |
|---|---|
| | TGGCGTGTTTGAATTACAACCAGGGGCATCAGTGTTCGTAAACG<br>TAACAGATCCCAGTCAGGTCTCGCACGGGACGGGATTTACTTC<br>CTTTGGTTTGCTGAAATTAGGCTCGGGATCCTCGAGTTCATCGT<br>CCTCATCCGGCTCATGTGATAAGACCCACACCTGCCCTCCCTG<br>TCCTGCCCCTGAGCTGCTGGGCGGACCTTCTGTGTTCCTGTTC<br>CCCCCCAAGCCTAAGGACACCCTGATGATCTCCAGGACCCCTG<br>AGGTGACCTGTGTGGTGGTGGACGTGTCTCACGAAGATCCCGA<br>GGTGAAGTTCAACTGGTACGTGGACGGCGTGGAGGTCCACAAC<br>GCCAAGACCAAGCCTAGGGAGGAGCAGTACAGCTCCACCTACC<br>GGGTGGTGTCTGTGCTGACCGTGCTGCACCAGGATTGGCTGAA<br>CGGAAAGGAGTATAAGTGTAAGGTCTCCAACAAGGCCCTGCCT<br>GCCCCCATCGAGAAAACCATCTCCAAGGCCAAGGGCCAGCCTC<br>GGGAGCCTCAGGTGTACACCCTGCCTCCTAGCAGGGAGGAGA<br>TGACCAAGAACCAGGTGTCCCTGACCTGTCTGGTGAAGGGCTT<br>CTACCCTTCCGATATCGCCGTGGAGTGGGAGTCTAATGGCCAG<br>CCCGAGAACAACTACAAGACCACCCCTCCTGTGCTGGACTCTG<br>ACGGCTCCTTCTTCCTGTACTCCAAGCTGACCGTGGACAAGTC<br>CAGATGGCAGCAGGGCAACGTGTTCTCCTGCTCCGTGATGCAC<br>GAGGCCCTGCACAATCACTACACCCAGAAGTCCCTGTCTCTGA<br>GTCCGGGCAAATAATAGGCGCGCC |

The nucleic acid molecule may be operatively linked to an expression control sequence, e.g. an expression control sequence which allows expression of the nucleic acid molecule in a desired host cell. The nucleic acid molecule may be located on a vector, e.g. a plasmid, a bacteriophage, a viral vector, a chromosomal integration vector, etc. Examples of suitable expression control sequences and vectors are described for example by Sambrook et al. (1989) Molecular Cloning, A Laboratory Manual, Cold Spring Harbor Press, and Ausubel et al. (1989), Current Protocols in Molecular Biology, John Wiley & Sons or more recent editions thereof.

Various expression vector/host cell systems may be used to express the nucleic acid sequences encoding the CD40 receptor agonist proteins of the present invention. Suitable host cells include, but are not limited to, prokaryotic cells such as bacteria, e.g. *E. coli*, eukaryotic host cells such as yeast cells, insect cells, plant cells or animal cells, preferably mammalian cells and, more preferably, human cells. Further, the invention relates to a non-human organism transformed or transfected with a nucleic acid molecule as described above. Such transgenic organisms may be generated by known methods of genetic transfer including homologous recombination.

A further aspect of the present invention relates to a pharmaceutical or diagnostic composition comprising as the active agent at least one CD40 receptor agonist protein, a respective nucleic acid encoding therefore, or a transformed or transfected cell, all as described herein.

The term "CD40L-associated disease or disorder" as used herein is any disease or disorder which may be ameliorated by addition of a CD40 receptor agonist. At least one CD40 receptor agonist protein, respective nucleic acid encoding therefore, or transformed or transfected cell, all as described herein may be used in therapy, e.g., in the prophylaxis and/or treatment of disorders caused by, associated with and/or accompanied by dysfunction of CD40L, particularly proliferative disorders, such as tumors, e.g. solid or lymphatic tumors; infectious diseases; inflammatory diseases; metabolic diseases; autoimmune disorders, e.g. rheumatoid and/ or arthritic diseases; degenerative diseases, e.g. neurodegenerative diseases such as multiple sclerosis; apoptosis-associated diseases or transplant rejections.

The term "dysfunction of CD40L" as used herein is to be understood as any function or expression of CD40L that deviates from the normal function or expression of CD40L, e.g., overexpression of the CD40L gene or protein, reduced or abolished expression of the CD40L gene or protein compared to the normal physiological expression level of CD40L, increased activity of CD40L, reduced or abolished activity of CD40L, increased binding of CD40L to any binding partners, e.g., to a receptor, particularly a CD40L receptor or another cytokine molecule, reduced or abolished binding to any binding partner, e.g. to a receptor, particularly a CD40L receptor or another cytokine molecule, compared to the normal physiological activity or binding of CD40L.

In various embodiments, a method is provided for diagnosing and/or treating a human subject suffering from a disorder which can be diagnosed and/or treated by targeting CD40L receptors comprising administering to the human subject a CD40 receptor agonist protein disclosed herein such that the effect on the activity of the target, or targets, in the human subject is agonistic, one or more symptoms is alleviated, and/or treatment is achieved. The CD40 receptor agonist proteins provided herein can be used to diagnose and/or treat humans suffering from primary and metastatic cancers, including carcinomas of breast, colon, rectum, lung (e.g., small cell lung cancer "SCLC" and non-small cell lung cancer "NSCLC"), oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), tumors arising from hematopoietic malignancies, acute leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), hairy cell leukemia, Hodgkin's and non-Hodgkin's lymphomas, DLBCL, follicular lymphomas, hematopoietic malignancies, Kaposi's sarcoma, malignant lymphoma, malignant histiocytosis, malignant melanoma, multiple myeloma, paraneoplastic syndrome/hypercalcemia of malignancy, or solid tumors.

A pharmaceutical composition comprising a CD40 receptor agonist protein disclosed herein and a pharmaceutically acceptable carrier is provided. In some embodiments, the pharmaceutical composition comprises at least one additional therapeutic agent for treating a disorder. For example, the additional agent may be a therapeutic agent, a chemotherapeutic agent; an imaging agent, a cytotoxic agent, an angiogenesis inhibitor, a kinase inhibitor (including but not limited to a KDR and a TIE-2 inhibitor), a co-stimulation molecule modulator or an immune checkpoint inhibitor (including but not limited to anti-B7.1, anti-B7.2, anti-B7.3, anti-B7.4, anti-CD28, anti-B7RP1, CTLA4-Ig, anti-CTLA-4, anti-PD-1, anti-PD-L1, anti-PD-L2, anti-ICOS, anti-LAG-3, anti-Tim3, anti-VISTA, anti-HVEM, anti-BTLA, LIGHT fusion protein, anti-CD137, anti-CD137L, anti-OX40, anti-OX40L, anti-CD70, anti-CD27, anti-GAL9, anti-A2AR, anti-KIR, anti-IDO-1, anti-CD20), a dendritic cell/antigen-presenting cell modulator (including but not limited to anti-CD40 antibody, anti-CD40 L, anti-DC-SIGN, anti-Dectin-1, anti-CD301, anti-CD303, anti-CD123, anti-CD207, anti-DNGR1, anti-CD205, anti-DCIR, anti-CD206, anti-ILT7), a modulator for Toll-like receptors (including but not limited to anti-TLR-1, anti-TLR-2, anti-TLR-3, anti-TLR-4, anti-TLR-4, anti-TLR-5, anti-TLR-6, anti-TLR-7, anti-TLR-8, anti-TLR-9), an adhesion molecule blocker (including but not limited to an anti-LFA-1 antibody, an anti-E/L selectin antibody, a small molecule inhibitor), an anti-cytokine antibody or functional fragment thereof (including but not limited to an anti-IL-18, an anti-TNF, or an anti-IL-6/cytokine receptor antibody), a bispecific redirected T cell or NK cell cytotoxicity (including but not limited to a BiTE®), a chimeric T cell receptor (CAR-T) based therapy, a T cell receptor (TCR)-based therapy, a therapeutic cancer vaccine, methotrexate, cyclosporin, rapamycin, FK506, a detectable label or reporter, a TNF antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

In an embodiment, a method of treating a cancer or in the prevention or inhibition of metastases from the tumors described herein, the CD40 receptor agonist protein(s) can be used alone or in combination with one or more additional agents, e.g., a chemotherapeutic, radiotherapy, or biological agent. In some embodiments, the agent can include the following: 13-cis-Retinoic Acid; 2-CdA; 2-Chlorodeoxy-adenosine; 5-Azacitidine; 5-Fluorouracil; 5-FU; 6-Mercaptopurine; 6-MP; 6-TG; 6-Thioguanine; Abraxane; Accutane®; Actinomycin-D; Adriamycin®; Adrucil®; Afinitor®; Agrylin®; Ala-Cort®; Aldesleukin; Alemtuzumab; ALIMTA; Alitretinoin; Alkaban-AQ®; Alkeran®; All-transretinoic Acid; Alpha Interferon; Altretamine; Amethopterin; Amifostine; Aminoglutethimide; Anagrelide; Anandron®; Anastrozole; Arabinosylcytosine; Ara-C Aranesp®; Aredia®; Arimidex®; Aromasin®; Arranon®; Arsenic Trioxide; Arzerra™; Asparaginase; ATRA; Avastin®; Azacitidine; BCG; BCNU; Bendamustine; Bevacizumab; Bexarotene; BEXXAR®; Bicalutamide; BiCNU; Blenoxane®; Bleomycin; Bortezomib; Busulfan; Busulfex®; C225; Calcium Leucovorin; Campath®; Camptosar®; Camptothecin-11; Capecitabine Carac™; Carboplatin; Carmustine; Carmustine Wafer; Casodex®; CC-5013; CCI-779; CCNU; CDDP; CeeNU; Cerubidine®; Cetuximab; Chlorambucil; Cisplatin; Citrovorum Factor; Cladribine; Cortisone; Cosmegen®; CPT-11; Cyclophosphamide; Cytadren®; Cytarabine; Cytarabine Liposomal; Cytosar-U®; Cytoxan®; Dacarbazine; Dacogen; Dactinomycin; Darbepoetin Alfa; Dasatinib; Daunomycin; Daunorubicin; Daunorubicin Hydrochloride; Daunorubicin Liposomal; DaunoXome®; Decadron; Decitabine; Delta-Cortef®; Deltasone®; Denileukin; Diftitox; DepoCyt™ Dexamethasone; Dexamethasone Acetate; Dexamethasone Sodium Phosphate; Dexasone; Dexrazoxane; DHAD; DIC; Diodex; Docetaxel; Doxil®; Doxorubicin; Doxorubicin Liposomal; Droxia™; DTIC; DTIC-Dome®; Duralone®; Duvelisib; Efudex®; Eligard™; Ellence™; Eloxatin™; Elspar®; Emcyt®; Epirubicin; Epoetin Alfa; Erbitux; Erlotinib; *Erwinia* L-asparaginase; Estramustine; Ethyol Etopophos®; Etoposide;

Etoposide Phosphate; Eulexin®; Everolimus; Evista®; Exemestane; Fareston®; Faslodex®; Femara®; Filgrastim; Floxuridine; Fludara®; Fludarabine; Fluoroplex®; Fluorouracil; Fluorouracil (cream); Fluoxymesterone; Flutamide; Folinic Acid; FUDR®; Fulvestrant; Gefitinib; Gemcitabine; Gemtuzumab ozogamicin; Gemzar; Gleevec™ Gliadel® Wafer; GM-CSF; Goserelin; Granulocyte-Colony Stimulating Factor (G-CSF); Granulocyte Macrophage Colony Stimulating Factor (G-MCSF); Halotestin®; Herceptin®; Hexadrol; Hexalen®; Hexamethylmelamine; HMM; Hycamtin®; Hydrea®; Hydrocort Acetate®; Hydrocortisone; Hydrocortisone Sodium Phosphate; Hydrocortisone Sodium Succinate; Hydrocortone Phosphate; Hydroxyurea; Ibrutinib; Ibritumomab; Ibritumomab Tiuxetan; Idamycin®; Idarubicin Ifex®; Interferon-alpha; Interferon-alpha-2b (PEG Conjugate); Ifosfamide; Interleukin-11 (IL-11); Interleukin-2 (IL-2); Imatinib mesylate; Imidazole Carboxamide; Intron A®; ipilimumab, Iressa®; Irinotecan; Isotretinoin; Ixabepilone; Ixempra™; KADCYCLA®; Kidrolase (t) Lanacort®; Lapatinib; L-asparaginase; LCR; Lenalidomide; Letrozole; Leucovorin; Leukeran; Leukine™; Leuprolide; Leurocristine; Leustatin™ Lirilumab; Liposomal Ara-C; Liquid Pred®; Lomustine; L-PAM; L-Sarcolysin; Lupron®; Lupron Depot®; Matulane®; Maxidex; Mechlorethamine; Mechlorethamine Hydrochloride; Medralone®; Medrol®; Megace®; Megestrol; Megestrol Acetate; MEK inhibitors; Melphalan; Mercaptopurine; Mesna; Mesnex™; Methotrexate; Methotrexate Sodium; Methylprednisolone; Meticorten®; Mitomycin; Mitomycin-C; Mitoxantrone M-Prednisol®; MTC; MTX; Mustargen®; Mustine; Mutamycin®; Myleran®; Mylocel™; Mylotarg®; Navitoclax; Navelbine®; Nelarabine; Neosar®; Neulasta™; Neumega®; Neupogen®; Nexavar®; Nilandron®; Nilotinib; Nilutamide; Nipent®; Nitrogen Mustard Novaldex®; Nivolumab; Novantrone®; Nplate; Octreotide; Octreotide acetate; Ofatumumab; Oncospar®; Oncovin®; Ontak®; Onxal™; Oprelvekin; Orapred®; Orasone®; Oxaliplatin; Paclitaxel; Paclitaxel Protein-bound; Pamidronate; Panitumumab; Panretin®; Paraplatin®; Pazopanib; Pediapred®; PEG Interferon; Pegaspargase; Pegfilgrastim; PEG-INTRON™ PEG-L-asparaginase; PEMETREXED; Pembrolizumab; Pentostatin; Pertuzumab; Phenylalanine Mustard; Pidilizumab; Platinol®; Platinol-AQ®; Prednisolone; Prednisone; Prelone®; Procarbazine; PROCRIT®; Proleukin®; Prolifeprospan 20 with Carmustine Implant; Purinethol®; BRAF inhibitors; Raloxifene; Revlimid®; Rheumatrex®; Rituxan®; Rituximab; Roferon-A®; Romiplostim; Rubex®; Rubidomycin hydrochloride; Sandostatin®; Sandostatin LAR®; Sargramostim; Solu-Cortef®; Solu-Medrol®; Sorafenib; SPRYCEL™; STI-571; STIVAGRA™, Streptozocin; SU11248; Sunitinib; Sutent®; Tamoxifen Tarceva®; Targretin®; Tasigna®; Taxol®; Taxotere®; Temodar®; Temozolomide Temsirolimus; Teniposide; TESPA; Thalidomide; Thalomid®; TheraCys®; Thioguanine; Thioguanine Tabloid®; Thiophosphoamide; Thioplex®; Thiotepa; TICE®; Toposar®; Topotecan; Toremifene; Torisel®; Tositumomab; Trastuzumab; Treanda®; Tremelimumab; Tretinoin; Trexall™; Trisenox®; TSPA; TYKERB®; Urelumab; VCR; Vectibix™; Velban®; Velcade®; Venetoclax; VePesid®; Vesanoid®; Viadur™; Vidaza®; Vinblastine; Vinblastine Sulfate; Vincasar Pfs®; Vincristine; Vinorelbine; Vinorelbine tartrate; VLB; VM-26; Vorinostat; Votrient; VP-16; Vumon®; Xeloda®; Zanosar®; Zevalin™; Zinecard®; Zoladex®; Zoledronic acid; Zolinza; or Zometa®, and/or any other agent not specifically listed here that target similar pathways.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more than one, or all of the substances or principles to be administered, while still achieving the desired therapeutic action. This may, e.g., be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In various embodiments, pharmaceutical compositions comprising one or more CD40 receptor agonist proteins, either alone or in combination with prophylactic agents, therapeutic agents, and/or pharmaceutically acceptable carriers are provided herein. In various embodiments, non-limiting examples of the uses of the pharmaceutical compositions disclosed herein include diagnosing, detecting, and/or monitoring a disorder, preventing, treating, managing, and/or ameliorating a disorder or one or more symptoms thereof, and/or in research. The formulation of pharmaceutical compositions, either alone or in combination with prophylactic agents, therapeutic agents, and/or pharmaceutically acceptable carriers, are known to one skilled in the art (US Patent Publication No. 20090311253 A1).

In various embodiments, a pharmaceutical formulation can comprise one or more amino acid, one or more polysaccharide and/or polysorbate, and a CD40 receptor agonist protein present at a concentration of between about 0.1 and 100 mg/ml, inclusive of endpoints (e.g., 0.1-10, 1-10, 0.01-50, 1-50, 1-100, 10-100, 25-100, 25-50, or 50-100 mg/ml), where the formulation is at a pH between about 5.0 and 7.0, inclusive of endpoints (e.g., a pH of about 5.0-6.0, 5.5-6.0, 5.0-6.5, 5.5-6.5, or 6.0-7.0). In an embodiment, at least one amino acid in the formulation is histidine and is present at a concentration of about 10-20 mM, 10-15 mM, 15-20 mM, or about 15 mM. In an embodiment, at least one polysaccharide in the formulation is sucrose and is present at a concentration of about 0-8.0% weight/volume (w/v). In an embodiment, the polysorbate in the formulation is polysorbate 80 and is at a concentration of about 0-0.06% w/v. In an embodiment, at least one amino acid in the formulation is arginine and is present at a concentration of about 0-1.5% w/v (e.g., 0.5-1.5, 1.0-1.5, or 0.5-1.0 w/v). In an embodiment, the CD40 receptor agonist protein is present in the formulation at a concentration of about 0.1-100 mg/ml, (e.g., about 1-100 mg/ml, or about 1-15 mg/ml, or about 1-7.5 mg/ml, or about 2.5-7.5 mg/ml, or about 5-7.5 mg/ml, or about 25-100 mg/ml, or about 20-60 mg/ml, or about 25-50 mg/ml, or about 25 mg/ml, or about 50 mg/ml, or about 0.1-60 mg/ml, or about 0.1-25 mg/ml, or about 1.0-60 mg/ml, or about 0.5-60 mg/ml, or about 0.1-2.0 mg/ml, or about 0.5-2.0 mg/ml, or about 1-5 mg/ml, or about 1-7.5 mg/ml, or about 1-15 mg/ml, or about 0.5 mg/ml, or about 1.0 mg/m).

As used herein, the phrase "effective amount" means an amount of CD40L agonist protein that results in a detectable improvement (e.g., at least about 5%, 10%, 15%, 20%, 25%, 30%, 35%, 40%, 45%, 50%, 55%, 60%, 65%, 70%, 75%, or more from baseline) in one or more parameters associated with a dysfunction of CD40L or with a CD40L-associated disease or disorder.

In various embodiments, the pharmaceutical formulation is an aqueous formulation, a lyophilized formulation, or a lyophilized and rehydrated formulation. In an embodiment, the hydrating solution is dextrose and/or saline (e.g., dextrose at a concentration of about 5% w/v and/or the saline at a concentration of about 0.9% w/v). In an embodiment, the pharmaceutical formulation comprises about 15 mM histidine, about 0.03% (w/v) polysorbate 80, about 4% (w/v) sucrose, and about 0.1-25 mg/ml of the CD40 receptor agonist protein, or about 1-15 mg/ml of CD40 receptor agonist protein, and is at a pH of about 6. In an embodiment, the formulation further comprises at least one additional agent.

In various embodiments, a formulation is used containing about 25 mg/ml CD40 receptor agonist protein, about 15 mM histidine, 0.03% polysorbate 80 (weight/volume, w/v), 4.0% sucrose (w/v), and a pH of about 6.0. In some embodiments, the formulation does not comprise arginine. In some embodiments, the formulation exhibits unexpectedly improved freeze-thaw stability, liquid formulation stability, and/or lyophilized formulation stability, as compared to other formulations comprising other components or concentrations.

Methods of administering a therapeutic agent provided herein include, but are not limited to, oral administration, parenteral administration (e.g., intradermal, intramuscular, intraperitoneal, intravenous and subcutaneous), epidural administration, intratumoral administration, mucosal administration (e.g., intranasal and oral routes) and pulmonary administration (e.g., aerosolized compounds administered with an inhaler or nebulizer). The formulation of pharmaceutical compositions for specific routes of administration, and the materials and techniques necessary for the various methods of administration are available and known to one skilled in the art (US Patent Publication No. 20090311253 A1).

In various embodiments, dosage regimens may be adjusted to provide for an optimum desired response (e.g., a therapeutic or prophylactic response). For example, a single bolus may be administered, several divided doses may be administered over time or the dose may be proportionally reduced or increased as indicated by the exigencies of the therapeutic situation. In some embodiments, parenteral compositions are formulated in dosage unit form for ease of administration and uniformity of dosage. The term "dosage unit form" refers to physically discrete units suited as unitary dosages for the mammalian subjects to be treated; each unit containing a predetermined quantity of active compound calculated to produce the desired therapeutic effect in association with the required pharmaceutical carrier.

An exemplary, non-limiting range for a therapeutically or prophylactically effective amount of a CD40 receptor agonist protein provided herein is about 0.1-100 mg/kg, (e.g., about 0.1-0.5, 0.1-1, 0.1-10, 0.1-20, 0.1-50, 0.1-75, 1-10, 1-15, 1-7.5, 1.25-15, 1.25-7.5, 2.5-7.5, 2.5-15, 5-15, 5-7.5, 1-20, 1-50, 7-75, 1-100, 5-10, 5-15, 5-20, 5-25, 5-50, 5-75, 10-20, 10-50, 10-75, or 10-100 mg/kg, or any concentration in between). In some embodiments, the CD40 receptor agonist protein is present in a pharmaceutical composition at a therapeutically effective concentration, e.g., a concentration of about 0.1-100 mg/ml (e.g., about 0.1-0.5, 0.1-1, 0.1-10, 0.1-20, 0.1-50, 0.1-75, 1-10, 1-20, 1-50, 1-75, 1-100, 5-10, 5-15, 5-20, 5-25, 5-50, 5-75, 10-20, 10-50, 10-75, or 10-100 mg/ml, or any concentration in between). Note that dosage values may vary with the type and/or severity of the condition to be alleviated. It is to be further understood that for any particular subject, specific dosage regimens may be adjusted over time according to the individual need and/or the professional judgment of the person administering or supervising the administration of the compositions, and that dosage ranges set forth herein are exemplary only and are not intended to limit the scope or practice of the claimed composition.

EXAMPLES

Example 1: Manufacture of a CD40 Receptor Agonist Protein 1.1 Polypeptide Structure
A) Amino acids Met1-Gly20
  Ig-Kappa-signal peptide, assumed signal peptidase cleavage site after amino acid Gly 20.
B) Amino acids Gln21-Leu161
  First soluble cytokine domain of the human CD40L ligand (CD40L, amino acid 121-261 of SEQ ID NO: 1).
C) Amino acids Gly162-Ser 169
  First peptide linker element of SEQ ID NO: 2.
D) Amino acids Gln170-Leu310
  Second soluble cytokine domain of the human CD40L ligand (CD40L, amino acids 121-261 of SEQ ID NO: 1).
E) Amino acids Gly311-Ser318.
  Second peptide linker element of SEQ ID NO: 2.
F) Amino acids Gln319-Leu459
  Third soluble cytokine domain of the human CD40L ligand (CD40L, amino acids 121-261 of SEQ ID NO: 1).
G) Amino acids Gly460-Cys482
  Hinge-linker element of SEQ ID NO: 16.
H) Amino acids Pro483-Lys700
  Antibody Fc fragment domain of SEQ ID NO: 13.
The above CD40 receptor agonist protein is shown in SEQ ID NO: 25.
The indicated linkers may be replaced by other preferred linkers, e.g. as shown in SEQ ID NOs: 3-12.

The indicated Hinge-linker element may be replaced by other preferred Hinge-linkers, e.g. as shown in SEQ ID NOs: 19 and 20.

It should be noted that the first and second peptide linkers do not need to be identical.

The signal peptide sequence (A) may be replaced by any other suitable, e.g. mammalian signal peptide sequence.

1.2 Gene Cassette Encoding the Polypeptide

The synthetic gene may be optimized in view of its codon usage for the expression in suitable host cells, e.g. insect cells or mammalian cells. A preferred nucleic acid sequence is shown in SEQ ID NO: 37.

Example 2: Expression and Purification 2.1 Cloning, Expression and Purification of Fusion Polypeptides The aforementioned fusion proteins were expressed recombinantly in two different eukaryotic host cells:

For initial analysis of aforementioned CD40 receptor agonist fusion proteins, Hek293T cells grown in DMEM+GlutaMAX (GibCo) supplemented with 10% FBS, 100 units/ml Penicillin and 100 [mu]g/ml Streptomycin were transiently transfected with a plasmid containing an expression cassette for a fusion polypeptide and an appropriate selection marker, e.g. a functional expression cassette comprising a blasticidine, puromycin or hygromycin resistence gene. In those cases, where a plurality of polypeptide chains is necessary to achieve the final product, the expression cassettes were either combined on one plasmid or positioned on different plasmids during the transfection. Cell culture supernatant containing recombinant fusion polypeptide was harvested three days post transfection and clarified by centrifugation at 300×g followed by filtration through a 0.22 μm sterile filter.

For larger scale expression of CD40 receptor agonist fusion proteins to be used in vivo, synthetic DNA cassettes encoding the aforementioned proteins were inserted into eukaryotic expression vectors comprising appropriate selection markers (e.g. a functional expression cassette comprising a blasticidin, puromycin or hygromycin resistance gene) and genetic elements suitable to enhance the number of transcriptionally active insertion sites within the host cells genome. The sequence verified expression vectors were introduced by electroporation into suspension adapted Chinese Hamster Ovary cells (CHO-S, Invitrogen). Appropriate selection pressure was applied three days post-transfection to the transfected cells. Surviving cells carrying the vector derived resistance gene(s) were recovered by subsequent cultivation under selection pressure. Upon stable growth of the selected cell pools in chemically defined medium (PowerCHO2-CD, Lonza) at 37° C. and 7% CO2 atmosphere in an orbital shaker incubator (100 rpm, 50 mm shaking throw), the individual supernatants were analyzed by ELISA-assays detecting the aforementioned proteins and the cell pools with the highest specific productivity were expanded in shake flasks prior to protein production (orbital shaker, 100 rpm, shaking throw 50 mm).

For lab-scale protein production, individual cell pools were cultured for 7-12 days in chemically defined medium (PowerCHO2-CD, Lonza) at 37° C. and 7% CO2 atmosphere in a Wave bioreactor 20/50 EHT (GE-Healthcare). The basal medium was PowerCHO2-CD supplemented with 4 mM Glutamax. Wave culture started with a viable cell concentration of 0.3 to 0.4×10e6 cells/ml and the following settings (for a five- or ten liter bag): shaking frequency 18 rpm, shaking ankle 7°, gas current 0.2-0.3 L/min, 7% CO2, 36.5° C. During the Wave run, the cell culture were fed twice with PowerFeed A (Lonza), usually on day 2 (20% feed) and day 5 (30% feed). After the second feed, shaking frequency was increased to 22 rpm, as well as the shaking ankle to 8°.

The bioreactor was usually harvested in between day 7 to day 12 when the cell viability dropped below 80%. First, the culture supernatant was clarified using a manual depth filtration system (Millipore Millistak Pod, MCOHC 0.054 m$^2$). For Strep-tagged proteins, Avidin was added to a final concentration of 0.5 mg/L. Finally, the culture supernatant containing the CD40 receptor agonist fusion protein was sterile filtered using a bottle top filter (0.22 μm, PES, Corning) and stored at 2-8° C. until further processing.

For affinity purification Streptactin Sepharose was packed to a column (gel bed 1 ml), equilibrated with 15 ml buffer W (100 mM Tris-HCl, 150 mM NaCl, pH 8.0) or PBS pH 7.4 and the cell culture supernatant was applied to the column with a flow rate of 4 ml/min. Subsequently, the column was washed with 15 ml buffer W and bound polypeptide was eluted stepwise by addition of 7×1 ml buffer E (100 mM Tris HCl, 150 mM NaCl, 2.5 mM Desthiobiotin, pH 8.0). Alternately, PBS pH 7.4 containing 2.5 mM Desthiobiotin can be used for this step.

Alternately to the Streptactin® (engineered streptavidin) Sepharose® (crosslinked agarose) based method, the affinity purification was performed employing a column with immobilized Protein-A as affinity ligand and an AKTA™ protein purification chromatography system (GE-Healthcare). A solid phase material with high affinity for the FC-domain of the fusion protein was chosen: MabSelect™ SuRe™ (an alkali-tolerant protein A-derived resin, GE Healthcare). Briefly, the clarified cell culture supernatant was loaded on a HiTrap™ (affinity column) MabSelect™ SuRe™ column (CV=5 ml) equilibrated in wash-buffer-1 (20 mM Pi, 95 mM NaCl, pH7.2) not exceeding a load of 10 mg fusion protein per ml column-bed. The column was washed with ten column-volumes (10CV) of aforementioned equilibration buffer followed by four column-volumes (4CV) of wash-buffer-2 (20 mM Pi, 95 mM NaCl, pH 8.0) to deplete host-cell protein and host-cell DNA. The column was then eluted with elution buffer (20 mM Pi, 95 mM NaCl, pH 3.5) and the eluate was collected in up to ten fractions with each fraction having a volume equal to column-bed volume (5 ml). Each fraction was neutralized with an equal volume of aforementioned wash-buffer-2. The linear velocity was set to 150 cm/h and kept constant during the aforementioned affinity chromatography method.

The protein amount of the eluate fractions was quantitated and peak fractions were concentrated by ultrafiltration and further purified by size exclusion chromatography (SEC).

SEC was performed on Superdex® (gel filtration media) 200 10/300 GL or HiLoad 26/60 columns using an AKTA™ chromatography system (GE-Healthcare). The columns were equilibrated with phosphate buffered saline and the concentrated, affinity-purified polypeptide was loaded onto the SEC column with the sample volume not exceeding 2% (v/v) of the column volume. In the case of Superdex® 200 10/300 GL columns (GE Healthcare), a flow rate of 0.5 ml per minute was applied. In the case of HiLoad® (high-resolution preparative gel filtration) 26/60 Superdex® 200 columns, a flow rate of 2.5 ml per minute was applied. The elution profile of the polypeptide was monitored by absorbance at 280 nm.

Figure 5:
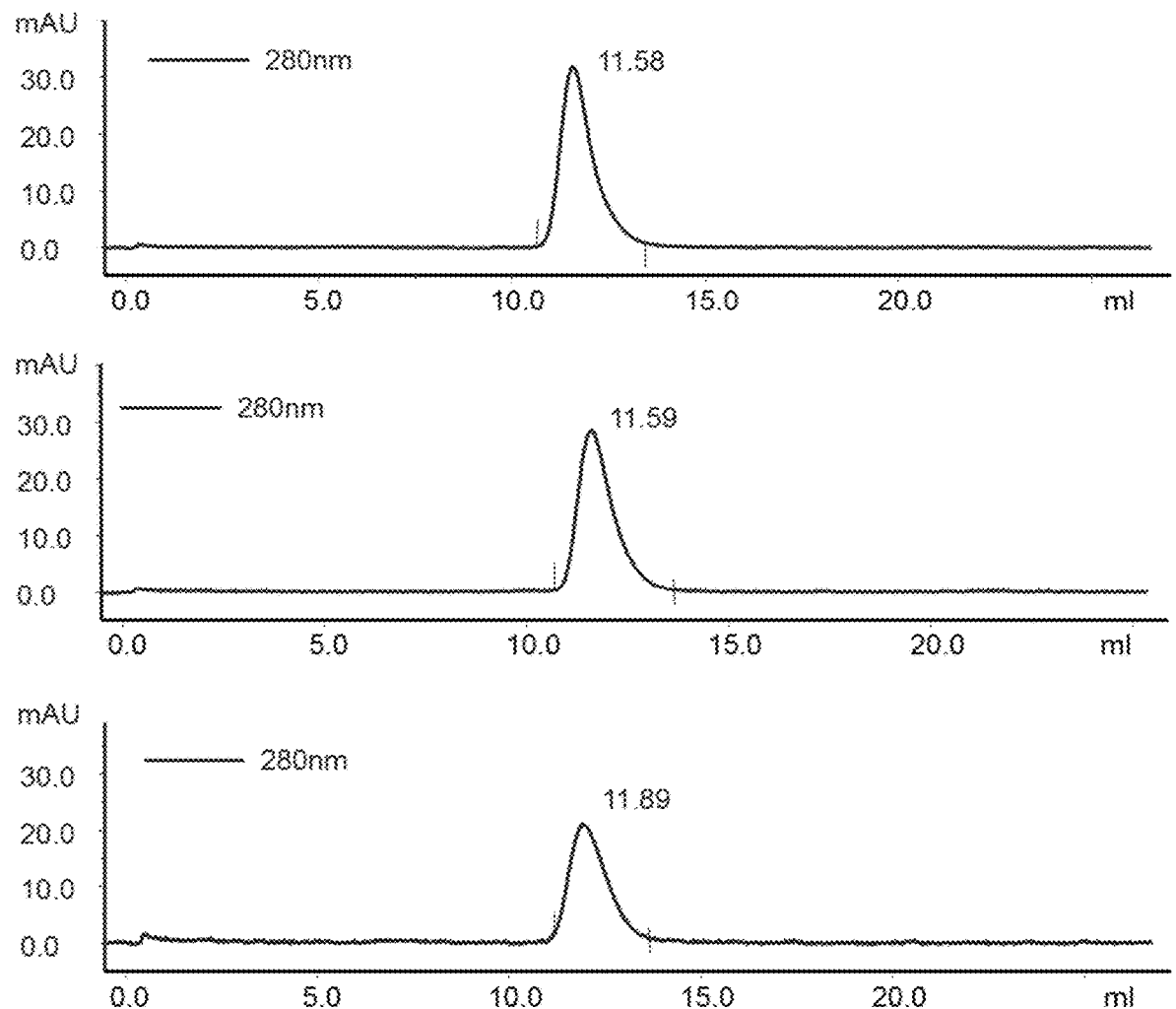
FIG. 5 The chromatograms of analytical SEC of hexavalent scCD 40L-RBD-FC fusion proteins PROTEIN A, PROTEIN B, and PROTEIN C.

The chromatograms of analytical SEC of hexavalent scCD 40L-RBD-FC fusion proteins PROTEIN A, PROTEIN B, and PROTEIN C are shown in FIG. 5.

For determination of the apparent molecular weight of purified fusion polypeptide under native conditions a Superdex® 200 column was loaded with standard proteins of known molecular weight. Based on the elution volume of the standard proteins a calibration curve was plotted and the apparent molecular weight of purified fusion polypeptide was determined. The FC-domain comprising CD40 receptor agonist fusion proteins typically eluted from the Superdex200 columns with an apparent molecular weight of approx. 160-180 kDa confirming the homodimerization of the mature CD40 receptor agonist fusion polypeptide by the Fc domain.

Figure 6:
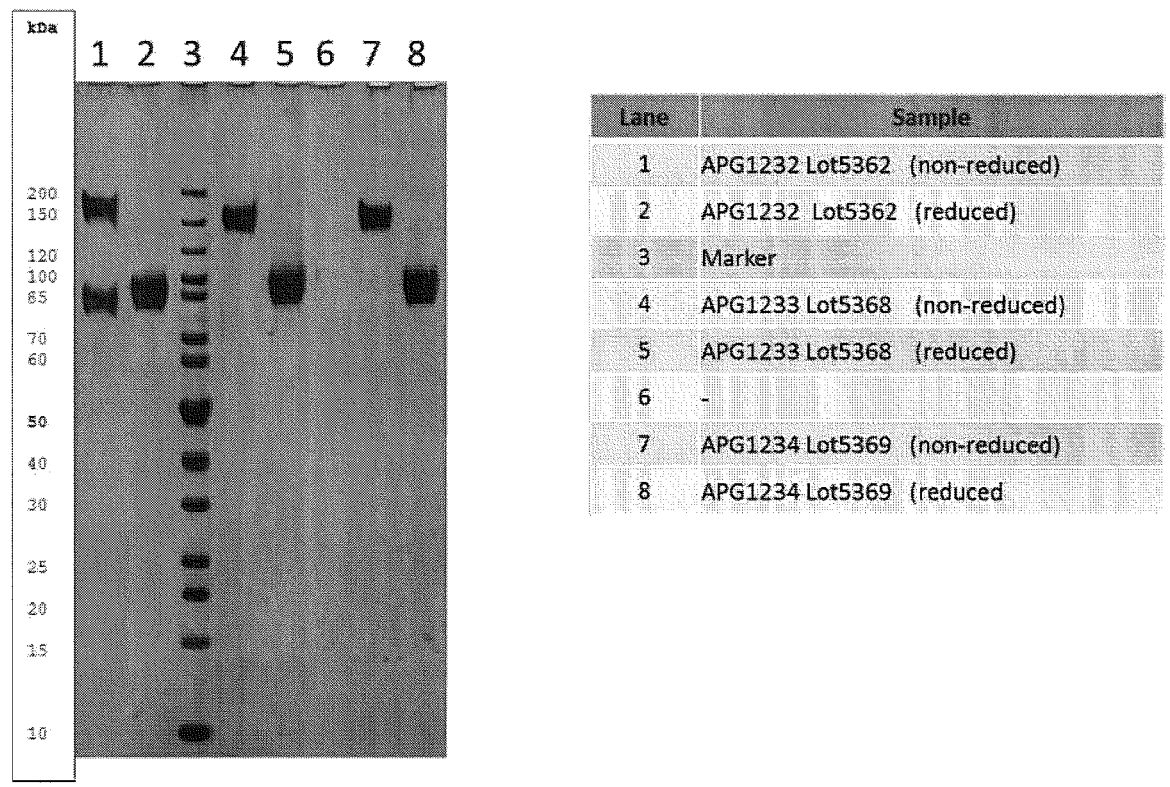
FIG. 6 SDS-Page gel electrophoresis of PROTEIN A, PROTEIN B, and PROTEIN C expressed proteins under non-reduced and reduced conditions Lane 1: PROTEIN A, non-reduced; Lane 2: PROTEIN A, reduced; Lane 3: Molecular weight marker; Lane 4: PROTEIN B, non-reduced; Lane 5: PROTEIN B, reduced; Lane 6: blank, Lane 7, PROTEIN C, non-reduced; Lane 8: PROTEIN C, reduced.

Example 3: SDS-PAGE Results of Dimer Proteins Expressed from Protein A, B, and C Protein A, B, and C were expressed and purified according to Examples 1 and 2. The three purified proteins were either non-reduced (lanes 1, 4, and 7) or reduced by dithiothreitol (Lanes 2, 5, 8), and performed SDS-Page gel electrophoresis in 4-12% bis-tris. The results are shown in FIG. 6. Lane 1 shows that under non-reduced condition, PROTEIN A expressed protein had both monomer (85 kDa) and dimer (170 kDa) bands, indicating self-reduction of the interchain hinge disulfides by endogenous free thiols present in the polypeptide itself. On the contrary, Lanes 4 and 7 show that under non-reduced condition, PROTEIN B and PROTEIN C expressed proteins had only dimer (170 kDa) band, indicating no self-reducing properties of the polypeptides themselves leaving the interchain disulfide-bridges of the hinge region intact.

Example 4: Trivalent Control Protein

To compare the relative binding between hexavalent CD40 receptor agonist fusion proteins and the trivalent CD40 stabilized with bacteriophage RB69-FOLDON, PROTEIN X (SEQ ID NO: 38) was expressed in CHO-S cells and purified as described in the former section. The SEC-purified protein is served as control in the following Examples. The sequence of PROTEIN X (SEQ ID NO: 38) is shown in Table 7. Amino-acids 1-20 of PROTEIN X represent the signal peptide and the mature proteins starts with amino acid Gln21. This protein consists of three identical polypeptides each comprising one soluble CD40L domain (Q121-L261 of SEQ ID NO: 1); this assembly stabilized by the trimerisation domain of bacteriophage RB69 fibritin fused with a flexible linker to the C-terminus of CD40L.

TABLE 7

| | Trivalent control proteins including a signal peptide |
|---|---|
| SEQ ID NO | Sequence |
| 38 (PROTEIN X) | METDTLLVFVLLVWVPAGNGQIAAHVISEASSK TTSVLQWAEKGYYTMSNNLVTLENGKQLTVKRQ GLYYIYAQVTFCSNREASSQAPFIASLCLKSPG RFERILLRAANTHSSAKPCGQQSIHLGGVFELQ PGASVFVNVTDPSQVSHGTGFTSFGLLKLGSGS SGSSGSSGSGYIEDAPSDGKFYVRKDGAWVELP TASGPSSSSSSAWSHPQFEK |

TABLE 7-continued

| | Trivalent control proteins including a signal peptide |
|---|---|
| SEQ ID NO | Sequence |
| 39 (Protein X2) | METDTLLVFVLLVWVPAGNGQIAAHVISEASSK TTSVLQWAEKGYYTMSNNLVTLENGKQLTVKRQ GLYYIYAQVTFCSNREASSQAPFIASLCLKSPG RFERILLRAANTHSSAKPCGQQSIHLGGVFELQ PGASVFVNVTDPSQVSHGTGFTSFGLLKLGSSS SSSAWSHPQFEK |

Example 5: Cellular Assays

5A. Cellular Binding Assay to Demonstrate Binding of CD40 Receptor Agonists to their Native Receptor CD40 on the Surface of Ramos B Cells In order to complement our affinity data for CD40 receptor agonists obtained using the quartz crystal microbalance (QCM), we wanted to investigate, whether our CD40 receptor agonists could bind their native receptor on the surface of cells. As B cells rely on CD40 signalling for full activation we used the human B cell line Ramos for this assay. Ramos cells are known to express CD40 on their surface and after incubation with CD40 receptor agonists one could imagine to be able to detect the C-terminal StrepTag II coupled to our CD40 receptor agonists with an antibody. This antibody could then in turn be detected with a fluorescent antibody and cells could be analysed on a flow cytometer.

Ramos B cells expressing CD40 on their surface were incubated with PROTEIN X (c), PROTEIN A (d), PROTEIN B (e) or PROTEIN C (f) on ice for 30 min to allow receptor-ligand association. Cells were washed with ice-cold wash buffer followed by incubation with a polyclonal rabbit anti-StrepTagII antibody on ice for 30 min to detect CD40 receptor agonists engaged on the cell surface. Fc-Receptors were blocked by addition of 1% human IgG (Gamunex) to staining and wash buffers. Cells were washed again with ice-cold wash buffer followed by incubation with a polyclonal Alexa488-labelled goat anti-rabbit antibody on ice and in the dark for 20 min. Cells were subsequently processed for flow cytometry by washing with ice-cold PBS. Cells were analyzed on a Guava Easycyte flow cytometer and fluorescence in the green channel was acquired. Mean fluorescence units were ultimately obtained from raw flow cytometry data using FlowJo software by gating on live cells and analyzing Alexa488-fluorescence within this gate. Cells only (a) and cells only incubated with the secondary goat anti-rabbit antibody (b) served as controls.

Figure 7:
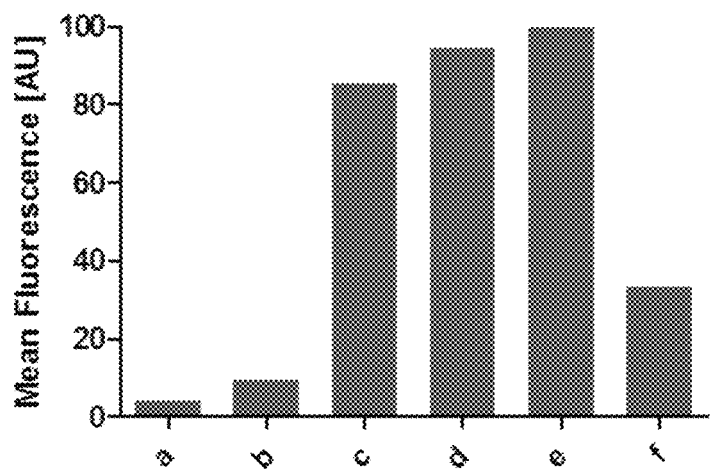
FIG. 7 CD40-expressing Ramos B cells were incubated with PROTEIN X (c), PROTEIN A (d), PROTEIN B (e), or PROTEIN C (f), and the binding activity were shown in fluorescent units. (a) is cells only. (b) is cells only incubated with a fluorescent-labelled antibody.

As can be seen in FIG. 7 all CD40 receptor agonists lead to a significant rise in fluorescence of cells when compared to cells only or to cells incubated with the fluorescent secondary antibody only. In this assay, PROTEIN B produced the highest fluorescence signal (e) indicating that PROTEIN B bound better to Ramos cells. The signal strength of PROTEIN B was followed by PROTEIN A (d) and PROTEIN X (c) with PROTEIN C (f) providing the weakest signal. Taken together one can assume that all CD40 receptor agonists bind their native receptor in a cellular context in vitro with PROTEIN B being the best binder.

5B. CD86 Upregulation on B Cells as a Readout of CD40 Signaling Triggered by CD40 Receptor Agonists CD86 is an activation marker on human B cells and it is the ligand for CD28 and CTLA-4 on T cells. CD86 surface expression is often used as a means to describe the activation state of B cells. As B cells need several signals for full activation including B cell receptor and CD40 ligation, we wondered, whether CD40 receptor agonists could lead to CD86 surface expression upregulation.

For that purpose, Ramos B cells were incubated with 1 µg/ml PROTEIN X (b), 10 µg/ml PROTEIN X (c), 1 µg/ml PROTEIN A (d) or 10 µg/ml PROTEIN A (e) in 24-well plates over night at 37° C. and 5% CO2. Untreated cells served as control (a). On the next day all samples were incubated with a PE-labelled anti-human CD86 antibody for 30 min on ice and in the dark. Fc-Receptors were blocked by addition of 1% human IgG (Gamunex) to staining and wash buffers. Samples were subsequently processed for flow cytometry on a Guava Easycyte flow cytometer. Mean fluorescence units were ultimately obtained from raw flow cytometry data using FlowJo software by gating on live cells and analyzing PE-fluorescence within this gate. Mean fluorescence values were used to express CD86 surface levels and values were normalized to the control sample, which was not incubated with a CD40 receptor agonist (a).

Figure 8:
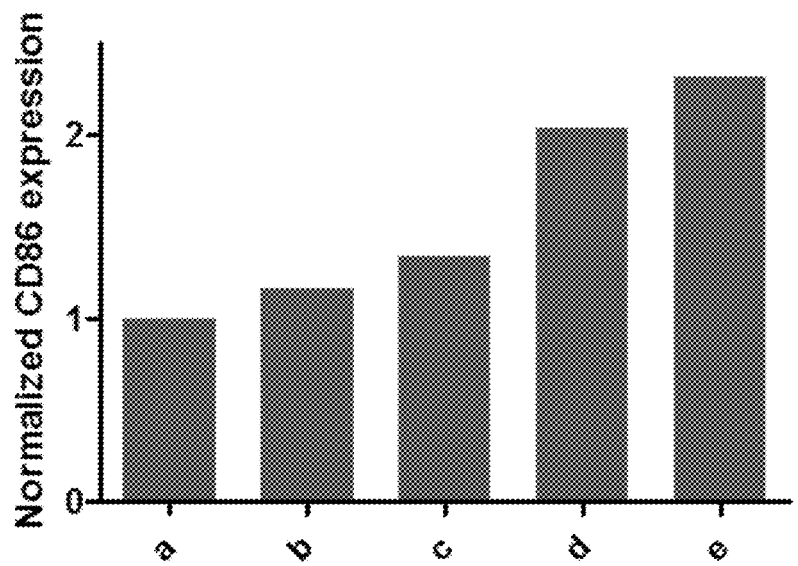
FIG. 8 CD40-expressing Ramos B cells were incubated with 1 µg/ml PROTEIN X (b), 10 µg/ml PROTEIN X (c), 1 µg/ml PROTEIN A (d), or 10 µg/ml PROTEIN A (e) and the binding activity were shown in CD86 expression normalized to (a), which was not incubated with any CD40 receptor agonist.

As can be observed in FIG. 8, all CD40 receptor agonists lead to an increase in CD86 surface expression indicating that all compounds triggered CD40 signaling. Importantly, this increase was dose-dependent when comparing bars b and c or d and e (1 µg/ml versus 10 µg/ml of the same compound, respectively). In addition, CD86 upregulation was stronger for PROTEIN A, which is hexavalent. This implied a clear avidity effect compared to PROTEIN X, which is only trivalent. The results indicate that the CD40 receptor agonists used here have biological activity in a dose-dependent manner.

5C. Whole-Blood Assay to Show Immune Cell Stimulation Concomitant with CD83 Upregulation by CD40 Receptor Agonists CD83 is a surface molecule, which is upregulated during the proliferation and maturation process of human immune cells. CD83 is found primarily on dendritic cells and T cells and it can be used as a marker for immune cell stimulation. As shown by Chowdhury et al. (Cancer Immunology Research, 2013, doi: 10.1158/2326-6066.CIR-13-0070) CD83 upregulation can be used as a means to study immune cell activation after CD40 ligation by antibodies. We thus wondered whether our CD40 receptor agnoists could also lead to CD83 upregulation in an assay employing whole-blood.

For that purpose, whole-blood was collected from healthy donors in EDTA tubes. 2 ml of blood were incubated with 1 µg/ml PROTEIN X (b), 50 µg/ml PROTEIN X (c), 1 µg/ml PROTEIN A (d) or 50 µg/ml PROTEIN A (e) in 24-well plates for 4 hours at 37° C. and 5% CO2. Untreated blood served as control (a). After 4 hours all samples were incubated with a PerCP/Cy5.5-labelled anti-human CD83 antibody for 20 min at room temperature and in the dark. Samples were subsequently processed for flow cytometry by fixation and red blood cell lysis using BD FACS lysing solution according to manufacturer's instructions. Samples were analyzed on a Guava Easycyte flow cytometer and cell populations (granulocytes, lymphocytes and monocytes) were gated based on their scatter profile. Fluorescence in the far-red channel was acquired for each population and analysed using FlowJo software. The percentage of CD83-positive cells was determined and normalized to the control sample, which was not incubated with a CD40 receptor agonist.

Figure 9:
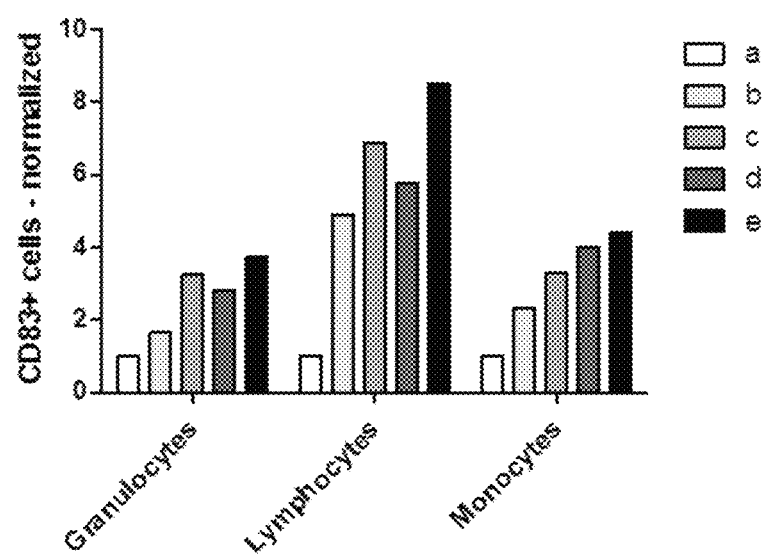

As can be observed in FIG. 9, both PROTEIN X and PROTEIN A lead to the generation of a new, CD83-positive population when compared to untreated blood cells (a). This new CD83-positive population appeared for all cell populations analyzed (lymphocytes, monocytes and granulocytes) and was most prominent in the case of lymphocytes. Importantly, the percentile share of CD83-positive cells was dose-dependent when comparing bars b and c or d and e (1 µg/ml versus 50 µg/ml of the same compound, respectively). In addition, the size of the CD83-positive population was stronger for the hexavalent PROTEIN A when comparing the same doses to PROTEIN X. The results show a clear avidity effect of hexavalent PROTEIN A compared to trivalent PROTEIN X. The results also show that the CD40 receptor agonists used here had a biological activity in a dose-dependent manner using fresh, human blood.

Example 6: In Vitro Binding Assay to Immobilized CD40-Receptor

The equilibrium binding constants ($K_D$) of trivalent constructs of CD40L (e.g.: PROTEIN X) and hexavalent constructs of CD40L (e.g. PROTEIN A, PROTEIN B, and PROTEIN C) to CD40 was calculated based on kinetic binding data ($k_{on}$ and $k_{off}$) determined with an automated biosensor system (Attana A100). The A100 allows to investigate molecular interactions in real-time based on the Quartz Crystal Microbalance (QCM) technique.

For this purpose human CD40-Fc, purchased from Enzo (catalogue number: ALX-522-016-C050), was immobilized on the surface of a carboxyl-activated QCM-chip. Trimeric and hexameric CD40L-constructs were used as soluble analyte at concentrations of 1, 5, and 10 µg/ml. Binding ($k_{on}$) and dissociation ($k_{off}$) was analyzed. Real time measurements and calculated $K_D$ thereof. revealed comparable binding activity among all hexavalent of proteins A, B and C, but superior binding of hexavalent proteins over trivalent Protein X.

TABLE 8

| | Binding strength of | | |
| --- | --- | --- | --- |
| Compound | $K_{on}$ | $K_{off}$ | $K_D$ [mol] |
| Protein X | $9.87e^4$ | $8.93e^{-4}$ | $9.05e^{-9}$ |
| Protein A | $1.75e^6$ | $2.92e^{-4}$ | $1.67e^{-10}$ |
| Protein B | $1.91e^6$ | $2.90e^{-4}$ | $1.52e^{-10}$ |
| Protein C | $1.82e^6$ | $3.21e^{-4}$ | $1.76e^{-10}$ |

Example 7: Half-Life Determination

Molecules PROTEIN A/PROTEIN B/PROTEIN C are each made up of two polypeptides covalently linked by three interchain disulfide bonds and all comprise the N297S mutation at position 297 of the Fc region (according to the EU index), resulting in aglycosylation of the CH2 domain. The outer surface cysteines of the soluble CD40L domains were mutated to serine (C194 equivalent positions of CD40L as shown in SEQ ID NO:1), resulting in SEQ ID NO: 31 (PROTEIN B) with C94S, C243S, C392S, as compared to SEQ ID NO:15 (PROTEIN A). Alternatively, the outer surface cysteines of the soluble CD40L domains were mutated to alanine (C194 equivalent positions of CD40L as shown in SEQ ID NO:1), resulting in SEQ ID NO: 35 (PROTEIN C) with C94A, C243A, C392A, as compared to SEQ ID NO:15 (PROTEIN A). Half-life of resulting FC-fusion proteins was assessed for an effect introduced by these alterations.

Female NMRI mice were treated with 1.0 mg/kg of each compound (PROTEIN N PROTEIN B/PROTEIN C) as a single intravenous bolus injection. Whole blood was collected before application (pre-dose), and up to 312 hours after test item administration. Serum was prepared and samples were stored at −80° C. until determination of serum concentrations.

Quantitation of the PROTEIN A/PROTEIN B/PROTEIN C concentrations in mouse serum was performed with an ELISA-assay detecting the individual CD40 agonists shown in Table 7. Plates were coated with CD40-Fc. CD40-Ligand constructs specifically binding to its receptor CD40 were then detected via their Strep-Tag employing StrepTactin® (engineered streptavidin)-HRP. ELISA assays were carried out using PROTEIN A or PROTEIN B or PROTEIN C as calibration and control samples. The measured data of the standard concentrations were used to create calibration curves using a 5-parameter fit. This enabled the determination of the unknown PROTEIN A or PROTEIN B or PROTEIN C concentrations in the respective mouse serum samples.

Pharmacokinetic parameters were calculated using the mean serum concentrations and the pharmacokinetic evaluation program PK Solutions Version 2.0 for non-compartmental pharmacokinetic data analysis (Summit Research Services, Montrose, Colo.). PK Solutions is an automated, Excel-based application, which computes pharmacokinetic parameters from concentration-time data obtained from analysis of e.g. biological samples following intravenous or extra-vascular routes of administration. PK Solutions calculates results without presuming any specific compartmental model.

The results from the pharmacokinetics evaluation are summarized in Table 9.

TABLE 9

Results of the exploratory PK study in NMRI-mice: single intravenous dose of 1 mg/kg of PROTEIN A/PROTEIN B/PROTEIN C.

|  | PROTEIN A | PROTEIN B | PROTEIN C |
|---|---|---|---|
| $t_{max}$ (h) | 0.083 | 0.083 | 0.083 |
| $C_{max}$ (µg/ml) | 8.22 | 10.23 | 9.74 |
| $t_{last}$ (h) | 192 | 312 | 144 |
| $C_{last}$ (µg/ml) | 0.286 | 0.122 | 0.242 |
| $t_{1/2}$ E (h) | 70.85 | 79.25 | 60.46 |
| $t_{1/2}$ E (d) | 2.95 | 3.30 | 2.52 |
| $AUC_{0-t}$ (µg*h/ml) | 178 | 273 | 134 |
| $AUC_{0-inf}$ (µg*h/ml) | 222 | 287 | 155 |

The results show that PROTEIN B which contains the C194S mutated Q121-L261 subsequence had a prolonged in vivo stability as compared to the wild-type (PROTEIN A) or PROTEIN C which contains C194A-mutein.

Example 8: Stability/Aggregation Test (Prophetic Example)

The contents of monomers and aggregates are determined by analytical SEC as described in Example 2. For this particular purpose the analysis is performed in buffers containing physiological salt concentrations at physiological pH (e.g. 0.9% NaCl, pH 7.4; PBS pH 7.4). A typical aggregation analysis is done on a Superdex® 200 column (GE Healthcare). This column separates proteins in the range between 10 to 800 kDa.

For determination of the apparent molecular weight of purified fusion polypeptide under native conditions a Superdex® 200 column is loaded with standard proteins of known molecular weight. Based on the elution volume of the standard proteins a calibration curve is plotted and the apparent molecular weight of purified fusion proteins of unknown molecular weight is calculated based on the elution volume.

SEC analysis of soluble, non-aggregated protein typically shows a distinct single protein peak at a defined elution volume (measured at OD at 280 nm or OD at 214 nm). This elution volume corresponds to the apparent native molecular weight of the particular protein. With regard to the definition of "monomer" in the case of FC-fusion proteins, the assembly of two polypeptide-chains is driven by the FC-part of the protein and the functional unit is a protein consisting of two chains. This unit that contains two FC-linked polypeptide chains is defined as "monomer" in the case of Fc-fusion proteins regardless of being a dimerized single-chain fusion polypeptide.

If protein aggregation occurs, the SEC analysis shows additional protein peaks with lower retention volumes. Protein oligomers potentially serve as aggregation seeds and a high content of oligomers potentially leads to aggregation of the protein. Oligomers of large molecular weight and aggregates elute in the void volume of the Superdex200 column and cannot be analyzed by SEC with respect to their native molecular weight.

Purified preparations of CD40 receptor agonist fusion proteins should preferably contain only defined monomeric protein and only a very low amount of oligomeric protein. The degree of aggregation/oligomerization of a particular CD40 receptor agonist fusion protein preparation is determined on basis of the SEC analysis by calculating the peak areas of the OD280 diagram for the defined monomer and the oligomer/aggregate fraction, respectively. Based on the total peak area the percentage of defined monomer protein is calculated as follows:

$$\text{monomer content}[\%] = [\text{Peak area monomer protein}]/[\text{Total peak area}] \times 100)$$

The definition for soluble protein as used in this text, describes a protein preparation of purified CD40 receptor agonist protein in a buffer of physiological salt concentrations at physiological pH that contains a defined soluble protein content of >90% within a typical protein concentration range from 0.2 to 10.0 mg/ml.

Example 9: CD40 Signaling Triggered by CD40 Receptor Agonists Increases the Expression of Activation Markers on M2-Polarized Macrophages M2-like macrophages are characterized by low expression of activation markers/T cell activation molecules, such as CD83, CD86 and HLA, and high expression of immunoregulatory molecules, such as IL-10. Because of this, M2-like macrophages are often called pro-tumor in contrast to "anti-tumor" M1-like macrophages. We decided to test if treatment with PROTEIN-B (SEQ ID NO:31) could increase the development of M1-like macrophages in normally M2-polarization conditions. To accomplish this, human peripheral blood mononuclear cells (PBMCs) were isolated and purified from buffy coats obtained from healthy volunteers using Ficoll-Hypaque (Sigma) according to the manufacturer's instructions. Monocytes were isolated by culturing PBMCs in medium (RPMI) in 12-well plates for 2 hr at 37° C. Monocytes were incubated in M2-polarizing conditions, IL-4 (50 ng/ml) and IL-10 (50 ng/ml), or medium alone for 3 d. During this incubation period, PROTEIN-B (50 ng/ml) or medium control was added to half of the wells. On 3 d, cell suspensions were stained with a cocktail of monoclonal antibodies, including CD206, CD163, CD86, CD83, HLA-DR and CD4 (BioLegend, eBioscience or BD Biosciences). DAPI (4',6-Diamidino-2-Phenylindole, Dihydrochloride) (ThermoFisher) was used according to the manufacturer's instructions to eliminate dead cells from the analysis. Cells were analyzed using the Guava easyCyte 12 Flow Cytometer (Merck Millipore). Antibody quality was checked and gating was performed using isotype controls. Tree Star FlowJo and Guava InCyte Software were used for the analysis of flow-cytometry data. Expression was quantified using gates and median fluorescence intensity (MFI). Treatment with IL-4 and IL-10 (M2-polarized macrophages) increased the expression of CD206 and CD163, classic markers of M2-like macrophages, on monocytes (See Table 10). In contrast, concurrent treatment with PROTEIN-B reduced CD206 and CD163 expression from 37% to 22%. CD86 (B7.2) is a classic T cell co-stimulatory molecule, and the binding partner of CD28, while CD83 is a marker of antigen presenting cell maturation. Importantly, PROTEIN-B treatment increased the co-expression of CD86 and CD83, from 5% to 20%, compared to IL-4/IL-10 alone. In addition, the expression of HLA-DR, DP was higher following PROTEIN-B treatment, 94 to 162 (MFI), compared to IL-4/IL-10 alone. These results demonstrate that PROTEIN-B treatment increases the activation status of M2-polarized macrophages and make them more potent antigen presenting cells.

TABLE 10

| M2-polarization conditions: IL-4 (50 ng/ml) and IL-10 (50 ng/ml) for 3 d | | | |
|---|---|---|---|
| | unstimulated monocytes | M2-polarized monocytes | M2-polarized monocytes with 50 ng/ml scCD40L-RBD-Fc |
| Percentage of macrophages that are CD206$^+$ and CD163$^+$ (M2-like) | 27% | 37% | 22% |
| Percentage of macrophages that are CD86$^+$ and CD83$^+$ (activation markers) | 7% | 5% | 20% |
| HLA-DR, DP (MFI) | 82 | 94 | 162 |

Example 10: CD40 Receptor Agonists Treated M2-Polarized Macrophages are More Potent Antigen Presenting Cells for Naïve CD4+ T Cell Activation in an Allogenic Co-Culture System M2-like macrophages are characterized by a weak ability to stimulate T cell responses due to low expression of HLA and co-stimulatory molecules (e.g., CD86). We wanted to test if treatment with PROTEIN-B could increase the potency of M2-like macrophages. To test this, M2-like macrophages were generated as described above with IL-10 and IL-4 (50 ng/ml of each). Naïve CD4+ T cells were isolated from PBMCs from a second (allogenic) donor using the naive CD4+ T cell Isoaltion Kit II (Miltenyi) according to the manufacturer's instructions. T cells were labeled with CellTrace CFSE Cell Proliferation Kit (ThermoFisher) according to the manufacturer's instructions. Monocytes treated for 3 days were added to naïve CD4+ T cells at a ratio of 10 lymphocytes to 1 monocyte. T cell proliferation and blasting (growth prior to cell division) were measured 3 d later using CFSE and Forward Scatter (FSC), respectively. Only 2% of T cells incubated in medium alone showed evidence of proliferation (CFSE dilution) or blasting (increased FSC) (See Table 11). In contrast, 23% of T cells incubated with unstimulated allogenic monocytes showed evidence of activation. Incubation of T cells with M2-polarized macrophages reduced the T cell response to 16%. Interestingly, adding PROTEIN-B to M2-polarizing conditions increased the potency of the allogenic macrophages and 31% of T cells responded. This data demonstrate that treatment of monocytes in with AGP1233 normally M2-polarization conditions results in more potent antigen presenting cells.

TABLE 11

| M2-polarization conditions: IL-4 (50 ng/ml) and IL-10 (50 ng/ml) for 3 d | | | |
|---|---|---|---|
| | CD4$^+$ T cells alone | CD4$^+$ T cells + unstimulated monocytes | CD4$^+$ T cells + M2-polarized monocytes | CD4$^+$ T cells + M2-polarized monocytes with 50 ng/ml scCD40L-RBD-Fc |
| Percentage of T cells that are CFSE$^{dim}$ or FSC$^{high}$ | 2% | 23% | 16% | 32% |

Example 11: CD40 Signaling Triggered by the Hexavalent CD40 Receptor Agonist is Most Efficient at Increasing the Expression of Activation Markers and Reduces Development of M2-Like Macrophages Following Culture with Purified Human Monocytes To test the efficiency of receptor clustering and downstream signaling, we compared the inventive hexavalent agonist PROTEIN-B to two homotrimeric trivalent CD40 receptor agonists representing common engineering concepts known in the art, PROTEIN-X2 (SEQ ID NO:39) represents the homotrimeric, non-stabilized CD40L-RBD itself and PROTEIN-X (SEQ ID NO:38) represents the homotrimeric CD40L-RBD stabilized by a C-terminal fused trimerisation scaffold derived from bacteriophage RB69. Since we have shown that productive CD40 receptor signaling leads to upregulation of activation markers and an increase in M1-like macrophage development, we purified human monocytes from buffy coats, as described above. Purified monocytes were incubated in medium supplemented with three different concentrations (10, 100 and 1000 ng/mL) of the three different constructs (See Table 12) for 3 d and cells were analyzed by flow cytometry for expression of activation and phenotype markers. Treatment with all three concentrations of the hexavalent PROTEIN-B produced a dose-dependent increase in CD86 expression (both as MFI and percentage positive) compared to the control. In contrast, none of the trivalent PROTEIN-X2 concentrations showed a difference compared to the control. In the case of the RB69-scaffold stabilized trivalent PROTEIN-X only the highest concentration, produced a slight increase of CD86 expression. In addition, the same compound and dose effect was seen with HLA-DR, DP expression which confirms that even low doses of the hexavalent construct are sufficient for receptor clustering and productive signaling, while the trivalent constructs show no activity or low activity at very high concentrations. Finally, approximately 20% of monocytes in media generally upregulate CD206 and CD163 expression in 3 d which is indicative of M2-like macrophage development. Treatment with all three concentrations of the hexavalent PROTEIN-B reduced this to less than 3%. Consistent with the activation marker data, only the high concentration of the trivalent PROTEIN-X showed any decrease in M2-like macrophage development. Taken together, the data demonstrates superior biological activity of inventive protein B.

TABLE 12

Monocytes were cultured for 3 d in the indicated conditions

| Culture conditions | Media only | PROTEIN-X2 (ng/mL) | | | PROTEIN-X (ng/mL) | | | PROTEIN-B (ng/mL) | | |
|---|---|---|---|---|---|---|---|---|---|---|
| | | 10 | 100 | 1000 | 10 | 100 | 1000 | 10 | 100 | 1000 |
| CD86 (MFI) | 12 | 11 | 12 | 11 | 11 | 11 | 12 | 17 | 39 | 47 |
| Percentage of macrophages that are CD86+ | 8% | 7% | 7% | 8% | 7% | 8% | 16% | 30% | 58% | 64% |
| HLA-DR,DP (MFI) | 27 | 26 | 29 | 22 | 26 | 26 | 31 | 39 | 54 | 55 |
| Percentage of macrophages that are HLA-DR,DP+ | 5% | 5% | 7% | 2% | 5% | 6% | 12% | 20% | 35% | 37% |
| Percentage of macrophages that are CD206+ and CD163+ (M2-like) | 23% | 21% | 23% | 21% | 17% | 21% | 10% | 3% | 2% | 1% |

The invention further relates to the following items 1-22
1. A CD40 receptor agonist protein comprising a polypeptide having the amino acid sequence selected from the group consisting of SEQ ID NO: 15, and 25-35.
2. A CD40 receptor agonist protein comprising two polypeptides each having the amino acid sequence set forth in SEQ ID NO: 27, 28, 29, 30, 32, or 34.
3. The CD40 receptor agonist protein of item 2, wherein the two polypeptides are covalently linked through three interchain disulfide bonds formed between cysteine residues 453, 459, and 462 of each polypeptide.
4. The CD40 receptor agonist protein of item 2 or 3, wherein one or more of the asparagine residues at positions 147 and 296 of the polypeptide(s) are N-glycosylated.
5. The CD40 receptor agonist protein of item 2 or 3, wherein the asparagine residues at both positions 147 and 296 of the polypeptide(s) are N-glycosylated.
6. The CD40 receptor agonist protein of item 1-5, wherein the polypeptide(s) are further post-translationally modified.
7. The CD40 receptor agonist protein of item 6, wherein the post-translational modification comprises modification of the N-terminal glutamine to pyroglutamate.
8. A pharmaceutical composition comprising the CD40 receptor agonist protein of any one of items 1-7 and one or more pharmaceutically acceptable carriers, diluents, excipients, and/or adjuvants.
9. A nucleic acid molecule encoding the CD40 receptor agonist protein of item 1.
10. An expression vector comprising the nucleic acid molecule of item 9.
11. A cell comprising the nucleic acid molecule of item 9.
12. The cell of item 11, which is a eukaryotic cell.
13. The cell of item 11, wherein the cell is a mammalian cell.
14. The cell of item 11, wherein the cell is a Chinese Hamster Ovary (CHO) cell.
15. A method of treating a subject having a CD40L-associated disease or disorder, the method comprising administering to the subject an effective amount of the CD40 receptor agonist protein of any one of items 1-7.
16. The method of item 15, wherein the disease or disorder is selected from the group consisting of: tumors, infectious diseases, inflammatory diseases, metabolic diseases, autoimmune disorders, degenerative diseases, apoptosis-associated diseases, and transplant rejections.
17. The method of item 16, wherein the tumors are solid tumors.
18. The method of item 16, wherein the tumors are lymphatic tumors.
19. The method of item 16, wherein the autoimmune disorders are rheumatoid diseases, arthritic diseases, or rheumatoid and arthritic diseases.
20. The method of item 16, wherein the disease or disorder is rheumatoid arthritis.
21. The method of item 16, wherein the degenerative disease is a neurodegenerative disease.
22. The method of item 21, wherein the neurodegenerative disease is multiple sclerosis.

The invention claimed is:

1. A CD40 receptor agonist protein comprising a single-chain fusion polypeptide comprising:
(i) a first soluble CD40L domain,
(ii) a first peptide linker,
(iii) a second soluble CD40L domain,
(iv) a second peptide linker, and
(v) a third soluble CD40L domain, and
(vi) an antibody Fc fragment, wherein the antibody Fc fragment (vi) consists of the amino acid sequence as shown in SEQ ID NO: 13 or amino acids 1-217 of SEQ ID NO: 13, wherein the soluble CD40L domains (i), (iii) and (v) each consists of amino acids 120-261 or 121-261 of SEQ ID NO: 1.

2. The CD40 receptor agonist protein of claim 1, wherein the antibody Fc fragment (vi) is located N-terminal to the first CD40L domain (i) and/or C terminal to the third CD40L domain (v).

3. The CD40 receptor agonist protein of claim 1, wherein the antibody Fc fragment is located C-terminally to the third CD40L domain (v).

4. The CD40 receptor agonist protein of claim 3, which is substantially non aggregating.

5. The CD40 receptor agonist protein of claim 1, wherein the soluble CD40L domains (i), (iii) and (v) consist of amino acids 121-261 of human CD40L according to SEQ ID NO: 1.

6. The CD40 receptor agonist protein of claim 1, wherein the first and second peptide linkers (ii) and (iv) independently have a length of 3-8 amino acids.

7. The CD40 receptor agonist protein of claim 6, wherein the first and the second peptide linkers (ii) and (iv) consist of the amino acid sequence according to SEQ ID NO: 2.

8. The CD40 receptor agonist protein of claim 1, which additionally comprises an N terminal signal peptide domain.

9. The CD40 receptor agonist protein of claim 1, wherein the antibody Fc fragment (vi) is fused to the soluble CD40L domain (i) and/or (v) via a hinge linker.

10. A CD40 receptor agonist, comprising the amino acid sequence of any one of SEQ ID NOs: 15, 25, 27-28, and 31-35.

11. The CD40 receptor agonist protein of claim 10, comprising two polypeptides each having the amino acid sequence as set forth in SEQ ID NOs: 27, 28, 32 or 34.

12. The CD40 receptor agonist protein of claim 11, wherein the two polypeptides each comprising an amino acid sequence as set forth in SEQ ID NO: 27, 28, 32 or 34 are covalently linked through three interchain disulfide bonds formed between cysteine residues 453, 459 and 462 of each polypeptide.

13. The CD40 receptor agonist protein of claim 12, wherein one or more of the asparagine residues at positions 147 and 296 of the polypeptides are N glycosylated.

14. The CD40 receptor agonist protein of claim 13, wherein the asparagine residues at both positions 147 and 296 of the polypeptides are N glycosylated.

15. The CD40 receptor agonist protein of claim 1, wherein the polypeptide(s) are post-translationally modified.

16. The CD40 receptor agonist protein of claim 15, wherein the post-translational modification comprises modification of the N-terminal glutamine to pyroglutamate.

17. A pharmaceutical or diagnostic composition comprising the CD40 receptor agonist protein of claim 1 and a pharmaceutically acceptable carriers, diluents, excipients, and/or adjuvants.

18. The CD40 receptor agonist protein of claim 1, wherein the first and second peptide linkers (ii) and (iv) independently consist of glycine and serine, or consist of glycine, serine and asparagine, wherein the asparagine is optionally glycosylated.

19. The CD40 receptor agonist protein of claim 9, wherein the hinge linker has one of the sequences of SEQ ID NOs: 16 and 19-24.

20. A CD40 receptor agonist protein comprising a single-chain fusion polypeptide comprising:
(i) a first soluble CD40L domain,
(ii) a first peptide linker,
(iii) a second soluble CD40L domain,
(iv) a second peptide linker, and
(v) a third soluble CD40L domain, and
(vi) an antibody Fc fragment, wherein the antibody Fc fragment (vi) consists of the amino acid sequence as shown in SEQ ID NO: 13 or amino acids 1-217 of SEQ ID NO: 13;
and wherein the soluble CD40L domains (i), (iii) and (v) each consists of amino acids 120-261 or 121-261 of SEQ ID NO: 1, with one or two mutations selected from the group consisting of: Q121S, Q121G, E129G, E129N, A130N, S132N, S132E, K133N, T134E, T134N, E142G, E142S, Y145S, Y146S, C178A, C178S, C178G, C194A, C194S, C194G, R200S, F201G, F201S, F201T, F201D, C218A, C218S, C218G, Q220E, Q220S, N240E, N240S, N240D, and N240T.

21. The CD40 receptor agonist protein of claim 20, wherein the first and second peptide linkers (ii) and (iv) independently have a length of 3-8 amino acids.

22. The CD40 receptor agonist protein of claim 21, wherein the first and the second peptide linkers (ii) and (iv) consist of the amino acid sequence according to SEQ ID NO: 2.

23. The CD40 receptor agonist protein of claim 20, wherein the antibody Fc fragment (vi) is fused to the soluble CD40L domain (i) and/or (v) via a hinge linker.

24. The CD40 receptor agonist protein of claim 23, wherein the hinge linker has one of the sequences of SEQ ID NOs: 16 and 19-24.

\* \* \* \* \*

SEQUENCE LISTING

<160> NUMBER OF SEQ ID NOS: 39

<210> SEQ ID NO 1
<211> LENGTH: 261
<212> TYPE: PRT
<213> ORGANISM: Homo sapiens
<223> OTHER INFORMATION: "wt CD40L"
<220> FEATURE:
<223> OTHER INFORMATION: wt CD40L

<400> SEQUENCE: 1

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 2
<211> LENGTH: 8
<212> TYPE: PRT
<213> ORGANISM: Artificial Sequence
<223> OTHER INFORMATION: "Linker Sequence"
<220> FEATURE:
<223> OTHER INFORMATION: Linker Sequence

<400> SEQUENCE: 2

Gly Ser Gly Ser Gly Asn Gly Ser
1               5

```
<210> SEQ ID NO 3
<211> LENGTH: 8
<212> TYPE: PRT
<213> ORGANISM: Artificial Sequence
<223> OTHER INFORMATION: "Linker Sequence"
<220> FEATURE:
<223> OTHER INFORMATION: Linker Sequence

<400> SEQUENCE: 3

Gly Ser Gly Ser Gly Ser Gly Ser
1               5

<210> SEQ ID NO 4
<211> LENGTH: 8
<212> TYPE: PRT
<213> ORGANISM: Artificial Sequence
<223> OTHER INFORMATION: "Linker Sequence"
<220> FEATURE:
<223> OTHER INFORMATION: Linker Sequence

<400> SEQUENCE: 4

Gly Gly Ser Gly Ser Gly Ser Gly
1               5

<210> SEQ ID NO 5
<211> LENGTH: 6
<212> TYPE: PRT
<213> ORGANISM: Artificial Sequence
<223> OTHER INFORMATION: "Linker Sequence"
<220> FEATURE:
<223> OTHER INFORMATION: Linker Sequence

<400> SEQUENCE: 5

Gly Gly Ser Gly Ser Gly
1               5

<210> SEQ ID NO 6
<211> LENGTH: 4
<212> TYPE: PRT
<213> ORGANISM: Artificial Sequence
<223> OTHER INFORMATION: "Linker Sequence"
<220> FEATURE:
<223> OTHER INFORMATION: Linker Sequence

<400> SEQUENCE: 6

Gly Gly Ser Gly
1

<210> SEQ ID NO 7
<211> LENGTH: 8
<212> TYPE: PRT
<213> ORGANISM: Artificial Sequence
<223> OTHER INFORMATION: "Linker Sequence"
<220> FEATURE:
<223> OTHER INFORMATION: Linker Sequence

<400> SEQUENCE: 7

Gly Gly Ser Gly Asn Gly Ser Gly
1               5

<210> SEQ ID NO 8
<211> LENGTH: 8
<212> TYPE: PRT
<213> ORGANISM: Artificial Sequence
<223> OTHER INFORMATION: "Linker Sequence"
<220> FEATURE:
<223> OTHER INFORMATION: Linker Sequence

<400> SEQUENCE: 8
```

```
Gly Gly Asn Gly Ser Gly Ser Gly
1               5
```

<210> SEQ ID NO 9
<211> LENGTH: 6
<212> TYPE: PRT
<213> ORGANISM: Artificial Sequence
<223> OTHER INFORMATION: "Linker Sequence"
<220> FEATURE:
<223> OTHER INFORMATION: Linker Sequence

<400> SEQUENCE: 9

```
Gly Gly Asn Gly Ser Gly
1               5
```

<210> SEQ ID NO 10
<211> LENGTH: 6
<212> TYPE: PRT
<213> ORGANISM: Artificial Sequence
<223> OTHER INFORMATION: "Linker Sequence"
<220> FEATURE:
<223> OTHER INFORMATION: Linker Sequence

<400> SEQUENCE: 10

```
Gly Ser Gly Ser Gly Ser
1               5
```

<210> SEQ ID NO 11
<211> LENGTH: 4
<212> TYPE: PRT
<213> ORGANISM: Artificial Sequence
<223> OTHER INFORMATION: "Linker Sequence"
<220> FEATURE:
<223> OTHER INFORMATION: Linker Sequence

<400> SEQUENCE: 11

```
Gly Ser Gly Ser
1
```

<210> SEQ ID NO 12
<211> LENGTH: 3
<212> TYPE: PRT
<213> ORGANISM: Artificial Sequence
<223> OTHER INFORMATION: "Linker Sequence"
<220> FEATURE:
<223> OTHER INFORMATION: Linker Sequence

<400> SEQUENCE: 12

```
Gly Ser Gly
1
```

<210> SEQ ID NO 13
<211> LENGTH: 218
<212> TYPE: PRT
<213> ORGANISM: Homo sapiens
<223> OTHER INFORMATION: "antibody Fc fragment"
<220> FEATURE:
<223> OTHER INFORMATION: antibody Fc fragment

<400> SEQUENCE: 13

```
Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45
```

```
Tyr Val Asp Gly Val Glu Val His Asn Ala Lys Thr Lys Pro Arg Glu
 50                  55                  60

Glu Gln Tyr Ser Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
             85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215
```

<210> SEQ ID NO 14
<211> LENGTH: 217
<212> TYPE: PRT
<213> ORGANISM: Homo sapiens
<223> OTHER INFORMATION: "antibody Fc fragment"
<220> FEATURE:
<223> OTHER INFORMATION: antibody Fc fragment

<400> SEQUENCE: 14

```
Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
             85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
```

-continued

```
                180                 185                 190
Phe Ser Cys Ser Val Met His Glu Ala Leu His Asn His Tyr Thr Gln
            195                 200                 205
Lys Ser Leu Ser Leu Ser Pro Gly Lys
            210                 215

<210> SEQ ID NO 15
<211> LENGTH: 714
<212> TYPE: PRT
<213> ORGANISM: Homo sapiens
<223> OTHER INFORMATION: "Protein A"
<220> FEATURE:
<223> OTHER INFORMATION: Protein A

<400> SEQUENCE: 15

Met Glu Thr Asp Thr Leu Leu Val Phe Val Leu Leu Trp Val Pro
1               5                   10                  15
Ala Gly Asn Gly Gln Ile Ala Ala His Val Ile Ser Glu Ala Ser Ser
                20                  25                  30
Lys Thr Thr Ser Val Leu Gln Trp Ala Glu Lys Gly Tyr Tyr Thr Met
                35                  40                  45
Ser Asn Asn Leu Val Thr Leu Glu Asn Gly Lys Gln Leu Thr Val Lys
50                  55                  60
Arg Gln Gly Leu Tyr Tyr Ile Tyr Ala Gln Val Thr Phe Cys Ser Asn
65                  70                  75                  80
Arg Glu Ala Ser Ser Gln Ala Pro Phe Ile Ala Ser Leu Cys Leu Lys
                85                  90                  95
Ser Pro Gly Arg Phe Glu Arg Ile Leu Leu Arg Ala Ala Asn Thr His
                100                 105                 110
Ser Ser Ala Lys Pro Cys Gly Gln Gln Ser Ile His Leu Gly Gly Val
                115                 120                 125
Phe Glu Leu Gln Pro Gly Ala Ser Val Phe Val Asn Val Thr Asp Pro
                130                 135                 140
Ser Gln Val Ser His Gly Thr Gly Phe Thr Ser Phe Gly Leu Leu Lys
145                 150                 155                 160
Leu Gly Ser Gly Ser Gly Asn Gly Ser Gln Ile Ala Ala His Val Ile
                165                 170                 175
Ser Glu Ala Ser Ser Lys Thr Thr Ser Val Leu Gln Trp Ala Glu Lys
                180                 185                 190
Gly Tyr Tyr Thr Met Ser Asn Asn Leu Val Thr Leu Glu Asn Gly Lys
                195                 200                 205
Gln Leu Thr Val Lys Arg Gln Gly Leu Tyr Tyr Ile Tyr Ala Gln Val
                210                 215                 220
Thr Phe Cys Ser Asn Arg Glu Ala Ser Ser Gln Ala Pro Phe Ile Ala
225                 230                 235                 240
Ser Leu Cys Leu Lys Ser Pro Gly Arg Phe Glu Arg Ile Leu Leu Arg
                245                 250                 255
Ala Ala Asn Thr His Ser Ser Ala Lys Pro Cys Gly Gln Gln Ser Ile
                260                 265                 270
His Leu Gly Gly Val Phe Glu Leu Gln Pro Gly Ala Ser Val Phe Val
                275                 280                 285
Asn Val Thr Asp Pro Ser Gln Val Ser His Gly Thr Gly Phe Thr Ser
                290                 295                 300
Phe Gly Leu Leu Lys Leu Gly Ser Gly Ser Gly Asn Gly Ser Gln Ile
305                 310                 315                 320
```

Ala Ala His Val Ile Ser Glu Ala Ser Ser Lys Thr Thr Ser Val Leu
            325                 330                 335

Gln Trp Ala Glu Lys Gly Tyr Tyr Thr Met Ser Asn Asn Leu Val Thr
        340                 345                 350

Leu Glu Asn Gly Lys Gln Leu Thr Val Lys Arg Gln Gly Leu Tyr Tyr
        355                 360                 365

Ile Tyr Ala Gln Val Thr Phe Cys Ser Asn Arg Glu Ala Ser Ser Gln
370                 375                 380

Ala Pro Phe Ile Ala Ser Leu Cys Leu Lys Ser Pro Gly Arg Phe Glu
385                 390                 395                 400

Arg Ile Leu Leu Arg Ala Ala Asn Thr His Ser Ser Ala Lys Pro Cys
            405                 410                 415

Gly Gln Gln Ser Ile His Leu Gly Gly Val Phe Glu Leu Gln Pro Gly
        420                 425                 430

Ala Ser Val Phe Val Asn Val Thr Asp Pro Ser Gln Val Ser His Gly
        435                 440                 445

Thr Gly Phe Thr Ser Phe Gly Leu Leu Lys Leu Gly Ser Gly Ser Ser
450                 455                 460

Ser Ser Ser Ser Ser Ser Gly Ser Cys Asp Lys Thr His Thr Cys Pro
465                 470                 475                 480

Pro Cys Pro Ala Pro Glu Leu Leu Gly Gly Pro Ser Val Phe Leu Phe
            485                 490                 495

Pro Pro Lys Pro Lys Asp Thr Leu Met Ile Ser Arg Thr Pro Glu Val
        500                 505                 510

Thr Cys Val Val Val Asp Val Ser His Glu Asp Pro Glu Val Lys Phe
        515                 520                 525

Asn Trp Tyr Val Asp Gly Val Glu Val His Asn Ala Lys Thr Lys Pro
530                 535                 540

Arg Glu Glu Gln Tyr Ser Thr Tyr Arg Val Val Ser Val Leu Thr
545                 550                 555                 560

Val Leu His Gln Asp Trp Leu Asn Gly Lys Glu Tyr Lys Cys Lys Val
            565                 570                 575

Ser Asn Lys Ala Leu Pro Ala Pro Ile Glu Lys Thr Ile Ser Lys Ala
        580                 585                 590

Lys Gly Gln Pro Arg Glu Pro Gln Val Tyr Thr Leu Pro Pro Ser Arg
        595                 600                 605

Glu Glu Met Thr Lys Asn Gln Val Ser Leu Thr Cys Leu Val Lys Gly
610                 615                 620

Phe Tyr Pro Ser Asp Ile Ala Val Glu Trp Glu Ser Asn Gly Gln Pro
625                 630                 635                 640

Glu Asn Asn Tyr Lys Thr Thr Pro Pro Val Leu Asp Ser Asp Gly Ser
            645                 650                 655

Phe Phe Leu Tyr Ser Lys Leu Thr Val Asp Lys Ser Arg Trp Gln Gln
        660                 665                 670

Gly Asn Val Phe Ser Cys Ser Val Met His Glu Ala Leu His Asn His
        675                 680                 685

Tyr Thr Gln Lys Ser Leu Ser Leu Ser Pro Gly Ser Ser Ser Ser Ser
690                 695                 700

Ser Ala Trp Ser His Pro Gln Phe Glu Lys
705                 710

<210> SEQ ID NO 16
<211> LENGTH: 23
<212> TYPE: PRT

```
<213> ORGANISM: Artificial Sequence
<223> OTHER INFORMATION: "hinge linker variant"
<220> FEATURE:
<223> OTHER INFORMATION: hinge linker variant

<400> SEQUENCE: 16

Gly Ser Gly Ser Ser Ser Ser Ser Ser Ser Gly Ser Cys Asp Lys
1               5                   10                  15

Thr His Thr Cys Pro Pro Cys
            20

<210> SEQ ID NO 17
<211> LENGTH: 20
<212> TYPE: PRT
<213> ORGANISM: Artificial Sequence
<223> OTHER INFORMATION: "signal peptide"
<220> FEATURE:
<223> OTHER INFORMATION: signal peptide

<400> SEQUENCE: 17

Met Glu Thr Asp Thr Leu Leu Val Phe Val Leu Leu Val Trp Val Pro
1               5                   10                  15

Ala Gly Asn Gly
            20

<210> SEQ ID NO 18
<211> LENGTH: 15
<212> TYPE: PRT
<213> ORGANISM: Artificial Sequence
<223> OTHER INFORMATION: "serine linker with strep tag"
<220> FEATURE:
<223> OTHER INFORMATION: serine linker with strep tag

<400> SEQUENCE: 18

Ser Ser Ser Ser Ser Ser Ala Trp Ser His Pro Gln Phe Glu Lys
1               5                   10                  15

<210> SEQ ID NO 19
<211> LENGTH: 21
<212> TYPE: PRT
<213> ORGANISM: Artificial Sequence
<223> OTHER INFORMATION: "hinge linker variant"
<220> FEATURE:
<223> OTHER INFORMATION: hinge linker variant

<400> SEQUENCE: 19

Gly Ser Gly Ser Ser Ser Ser Ser Gly Ser Cys Asp Lys Thr His
1               5                   10                  15

Thr Cys Pro Pro Cys
            20

<210> SEQ ID NO 20
<211> LENGTH: 22
<212> TYPE: PRT
<213> ORGANISM: Artificial Sequence
<223> OTHER INFORMATION: "hinge linker variant"
<220> FEATURE:
<223> OTHER INFORMATION: hinge linker variant

<400> SEQUENCE: 20

Gly Ser Gly Ser Ser Ser Ser Ser Ser Gly Ser Cys Asp Lys Thr
1               5                   10                  15

His Thr Cys Pro Pro Cys
            20
```

```
<210> SEQ ID NO 21
<211> LENGTH: 20
<212> TYPE: PRT
<213> ORGANISM: Artificial Sequence
<223> OTHER INFORMATION: "hinge linker variant"
<220> FEATURE:
<223> OTHER INFORMATION: hinge linker variant

<400> SEQUENCE: 21

Gly Ser Gly Ser Ser Ser Ser Gly Ser Cys Asp Lys Thr His Thr
1               5                   10                  15

Cys Pro Pro Cys
            20

<210> SEQ ID NO 22
<211> LENGTH: 18
<212> TYPE: PRT
<213> ORGANISM: Artificial Sequence
<223> OTHER INFORMATION: "hinge linker variant"
<220> FEATURE:
<223> OTHER INFORMATION: hinge linker variant

<400> SEQUENCE: 22

Gly Ser Gly Ser Ser Ser Gly Ser Cys Asp Lys Thr His Thr Cys Pro
1               5                   10                  15

Pro Cys

<210> SEQ ID NO 23
<211> LENGTH: 20
<212> TYPE: PRT
<213> ORGANISM: Artificial Sequence
<223> OTHER INFORMATION: "hinge linker variant"
<220> FEATURE:
<223> OTHER INFORMATION: hinge linker variant

<400> SEQUENCE: 23

Gly Ser Gly Ser Ser Ser Gly Ser Cys Asp Lys Thr His Thr Cys Pro
1               5                   10                  15

Pro Cys Gly Ser
            20

<210> SEQ ID NO 24
<211> LENGTH: 22
<212> TYPE: PRT
<213> ORGANISM: Artificial Sequence
<223> OTHER INFORMATION: "hinge linker variant"
<220> FEATURE:
<223> OTHER INFORMATION: hinge linker variant

<400> SEQUENCE: 24

Gly Ser Gly Ser Ser Ser Gly Ser Cys Asp Lys Thr His Thr Cys Pro
1               5                   10                  15

Pro Cys Gly Ser Gly Ser
            20

<210> SEQ ID NO 25
<211> LENGTH: 700
<212> TYPE: PRT
<213> ORGANISM: Artificial Sequence
<223> OTHER INFORMATION: "Protein-A without strep tag"
<220> FEATURE:
<223> OTHER INFORMATION: Protein-A without strep tag

<400> SEQUENCE: 25

Met Glu Thr Asp Thr Leu Leu Val Phe Val Leu Leu Val Trp Val Pro
1               5                   10                  15
```

```
Ala Gly Asn Gly Gln Ile Ala Ala His Val Ile Ser Glu Ala Ser Ser
            20                  25                  30

Lys Thr Thr Ser Val Leu Gln Trp Ala Glu Lys Gly Tyr Tyr Thr Met
        35                  40                  45

Ser Asn Asn Leu Val Thr Leu Glu Asn Gly Lys Gln Leu Thr Val Lys
    50                  55                  60

Arg Gln Gly Leu Tyr Tyr Ile Tyr Ala Gln Val Thr Phe Cys Ser Asn
65                  70                  75                  80

Arg Glu Ala Ser Ser Gln Ala Pro Phe Ile Ala Ser Leu Cys Leu Lys
                85                  90                  95

Ser Pro Gly Arg Phe Glu Arg Ile Leu Leu Arg Ala Ala Asn Thr His
            100                 105                 110

Ser Ser Ala Lys Pro Cys Gly Gln Gln Ser Ile His Leu Gly Gly Val
        115                 120                 125

Phe Glu Leu Gln Pro Gly Ala Ser Val Phe Val Asn Val Thr Asp Pro
    130                 135                 140

Ser Gln Val Ser His Gly Thr Gly Phe Thr Ser Phe Gly Leu Leu Lys
145                 150                 155                 160

Leu Gly Ser Gly Ser Gly Asn Gly Ser Gln Ile Ala Ala His Val Ile
            165                 170                 175

Ser Glu Ala Ser Ser Lys Thr Thr Ser Val Leu Gln Trp Ala Glu Lys
        180                 185                 190

Gly Tyr Tyr Thr Met Ser Asn Asn Leu Val Thr Leu Glu Asn Gly Lys
    195                 200                 205

Gln Leu Thr Val Lys Arg Gln Gly Leu Tyr Tyr Ile Tyr Ala Gln Val
    210                 215                 220

Thr Phe Cys Ser Asn Arg Glu Ala Ser Ser Gln Ala Pro Phe Ile Ala
225                 230                 235                 240

Ser Leu Cys Leu Lys Ser Pro Gly Arg Phe Glu Arg Ile Leu Leu Arg
                245                 250                 255

Ala Ala Asn Thr His Ser Ser Ala Lys Pro Cys Gly Gln Gln Ser Ile
            260                 265                 270

His Leu Gly Gly Val Phe Glu Leu Gln Pro Gly Ala Ser Val Phe Val
        275                 280                 285

Asn Val Thr Asp Pro Ser Gln Val Ser His Gly Thr Gly Phe Thr Ser
    290                 295                 300

Phe Gly Leu Leu Lys Leu Gly Ser Gly Ser Gly Asn Gly Ser Gln Ile
305                 310                 315                 320

Ala Ala His Val Ile Ser Glu Ala Ser Ser Lys Thr Thr Ser Val Leu
                325                 330                 335

Gln Trp Ala Glu Lys Gly Tyr Tyr Thr Met Ser Asn Asn Leu Val Thr
            340                 345                 350

Leu Glu Asn Gly Lys Gln Leu Thr Val Lys Arg Gln Gly Leu Tyr Tyr
        355                 360                 365

Ile Tyr Ala Gln Val Thr Phe Cys Ser Asn Arg Glu Ala Ser Ser Gln
    370                 375                 380

Ala Pro Phe Ile Ala Ser Leu Cys Leu Lys Ser Pro Gly Arg Phe Glu
385                 390                 395                 400

Arg Ile Leu Leu Arg Ala Ala Asn Thr His Ser Ser Ala Lys Pro Cys
                405                 410                 415

Gly Gln Gln Ser Ile His Leu Gly Gly Val Phe Glu Leu Gln Pro Gly
            420                 425                 430
```

-continued

```
Ala Ser Val Phe Val Asn Val Thr Asp Pro Ser Gln Val Ser His Gly
            435                 440                 445

Thr Gly Phe Thr Ser Phe Gly Leu Leu Lys Leu Gly Ser Gly Ser Ser
    450                 455                 460

Ser Ser Ser Ser Ser Gly Ser Cys Asp Lys Thr His Thr Cys Pro
465                 470                 475                 480

Pro Cys Pro Ala Pro Glu Leu Leu Gly Gly Pro Ser Val Phe Leu Phe
                485                 490                 495

Pro Pro Lys Pro Lys Asp Thr Leu Met Ile Ser Arg Thr Pro Glu Val
            500                 505                 510

Thr Cys Val Val Val Asp Val Ser His Glu Asp Pro Glu Val Lys Phe
            515                 520                 525

Asn Trp Tyr Val Asp Gly Val Glu Val His Asn Ala Lys Thr Lys Pro
        530                 535                 540

Arg Glu Glu Gln Tyr Ser Ser Thr Tyr Arg Val Val Ser Val Leu Thr
545                 550                 555                 560

Val Leu His Gln Asp Trp Leu Asn Gly Lys Glu Tyr Lys Cys Lys Val
                565                 570                 575

Ser Asn Lys Ala Leu Pro Ala Pro Ile Glu Lys Thr Ile Ser Lys Ala
            580                 585                 590

Lys Gly Gln Pro Arg Glu Pro Gln Val Tyr Thr Leu Pro Pro Ser Arg
        595                 600                 605

Glu Glu Met Thr Lys Asn Gln Val Ser Leu Thr Cys Leu Val Lys Gly
        610                 615                 620

Phe Tyr Pro Ser Asp Ile Ala Val Glu Trp Glu Ser Asn Gly Gln Pro
625                 630                 635                 640

Glu Asn Asn Tyr Lys Thr Thr Pro Pro Val Leu Asp Ser Asp Gly Ser
                645                 650                 655

Phe Phe Leu Tyr Ser Lys Leu Thr Val Asp Lys Ser Arg Trp Gln Gln
            660                 665                 670

Gly Asn Val Phe Ser Cys Ser Val Met His Glu Ala Leu His Asn His
        675                 680                 685

Tyr Thr Gln Lys Ser Leu Ser Leu Ser Pro Gly Lys
    690                 695                 700
```

<210> SEQ ID NO 26
<211> LENGTH: 699
<212> TYPE: PRT
<213> ORGANISM: Artificial Sequence
<223> OTHER INFORMATION: "CD40L-wt fused to Fc of SEQ ID 14"
<220> FEATURE:
<223> OTHER INFORMATION: CD40L-wt fused to Fc of SEQ ID 14

<400> SEQUENCE: 26

```
Met Glu Thr Asp Thr Leu Leu Val Phe Val Leu Leu Val Trp Val Pro
1               5                   10                  15

Ala Gly Asn Gly Gln Ile Ala Ala His Val Ile Ser Glu Ala Ser Ser
            20                  25                  30

Lys Thr Thr Ser Val Leu Gln Trp Ala Glu Lys Gly Tyr Tyr Thr Met
        35                  40                  45

Ser Asn Asn Leu Val Thr Leu Glu Asn Gly Lys Gln Leu Thr Val Lys
    50                  55                  60

Arg Gln Gly Leu Tyr Tyr Ile Tyr Ala Gln Val Thr Phe Cys Ser Asn
65                  70                  75                  80

Arg Glu Ala Ser Ser Gln Ala Pro Phe Ile Ala Ser Leu Cys Leu Lys
                85                  90                  95
```

```
Ser Pro Gly Arg Phe Glu Arg Ile Leu Leu Arg Ala Ala Asn Thr His
            100                 105                 110
Ser Ser Ala Lys Pro Cys Gly Gln Gln Ser Ile His Leu Gly Gly Val
            115                 120                 125
Phe Glu Leu Gln Pro Gly Ala Ser Val Phe Val Asn Val Thr Asp Pro
            130                 135                 140
Ser Gln Val Ser His Gly Thr Gly Phe Thr Ser Phe Gly Leu Leu Lys
145                 150                 155                 160
Leu Gly Ser Gly Ser Gly Asn Gly Ser Gln Ile Ala Ala His Val Ile
                165                 170                 175
Ser Glu Ala Ser Ser Lys Thr Thr Ser Val Leu Gln Trp Ala Glu Lys
            180                 185                 190
Gly Tyr Tyr Thr Met Ser Asn Asn Leu Val Thr Leu Glu Asn Gly Lys
            195                 200                 205
Gln Leu Thr Val Lys Arg Gln Gly Leu Tyr Tyr Ile Tyr Ala Gln Val
            210                 215                 220
Thr Phe Cys Ser Asn Arg Glu Ala Ser Ser Gln Ala Pro Phe Ile Ala
225                 230                 235                 240
Ser Leu Cys Leu Lys Ser Pro Gly Arg Phe Glu Arg Ile Leu Leu Arg
                245                 250                 255
Ala Ala Asn Thr His Ser Ser Ala Lys Pro Cys Gly Gln Gln Ser Ile
            260                 265                 270
His Leu Gly Gly Val Phe Glu Leu Gln Pro Gly Ala Ser Val Phe Val
            275                 280                 285
Asn Val Thr Asp Pro Ser Gln Val Ser His Gly Thr Gly Phe Thr Ser
            290                 295                 300
Phe Gly Leu Leu Lys Leu Gly Ser Gly Ser Gly Asn Gly Ser Gln Ile
305                 310                 315                 320
Ala Ala His Val Ile Ser Glu Ala Ser Ser Lys Thr Thr Ser Val Leu
                325                 330                 335
Gln Trp Ala Glu Lys Gly Tyr Tyr Thr Met Ser Asn Asn Leu Val Thr
            340                 345                 350
Leu Glu Asn Gly Lys Gln Leu Thr Val Lys Arg Gln Gly Leu Tyr Tyr
            355                 360                 365
Ile Tyr Ala Gln Val Thr Phe Cys Ser Asn Arg Glu Ala Ser Ser Gln
            370                 375                 380
Ala Pro Phe Ile Ala Ser Leu Cys Leu Lys Ser Pro Gly Arg Phe Glu
385                 390                 395                 400
Arg Ile Leu Leu Arg Ala Ala Asn Thr His Ser Ser Ala Lys Pro Cys
                405                 410                 415
Gly Gln Gln Ser Ile His Leu Gly Gly Val Phe Glu Leu Gln Pro Gly
            420                 425                 430
Ala Ser Val Phe Val Asn Val Thr Asp Pro Ser Gln Val Ser His Gly
            435                 440                 445
Thr Gly Phe Thr Ser Phe Gly Leu Leu Lys Leu Gly Ser Gly Ser Ser
            450                 455                 460
Ser Ser Ser Ser Ser Ser Gly Ser Cys Asp Lys Thr His Thr Cys Pro
465                 470                 475                 480
Pro Cys Pro Ala Pro Pro Val Ala Gly Pro Ser Val Phe Leu Phe Pro
                485                 490                 495
Pro Lys Pro Lys Asp Thr Leu Met Ile Ser Arg Thr Pro Glu Val Thr
            500                 505                 510
```

```
Cys Val Val Asp Val Ser His Glu Asp Pro Glu Val Lys Phe Asn
            515                 520                 525
Trp Tyr Val Asp Gly Val Glu Val His Asn Ala Lys Thr Lys Pro Arg
530                 535                 540
Glu Glu Gln Tyr Asn Ser Thr Tyr Arg Val Val Ser Val Leu Thr Val
545                 550                 555                 560
Leu His Gln Asp Trp Leu Asn Gly Lys Glu Tyr Lys Cys Lys Val Ser
            565                 570                 575
Asn Lys Gly Leu Pro Ser Ser Ile Glu Lys Thr Ile Ser Lys Ala Lys
            580                 585                 590
Gly Gln Pro Arg Glu Pro Gln Val Tyr Thr Leu Pro Pro Ser Arg Glu
            595                 600                 605
Glu Met Thr Lys Asn Gln Val Ser Leu Thr Cys Leu Val Lys Gly Phe
610                 615                 620
Tyr Pro Ser Asp Ile Ala Val Glu Trp Glu Ser Asn Gly Gln Pro Glu
625                 630                 635                 640
Asn Asn Tyr Lys Thr Thr Pro Pro Val Leu Asp Ser Asp Gly Ser Phe
            645                 650                 655
Phe Leu Tyr Ser Lys Leu Thr Val Asp Lys Ser Arg Trp Gln Gln Gly
            660                 665                 670
Asn Val Phe Ser Cys Ser Val Met His Glu Ala Leu His Asn His Tyr
            675                 680                 685
Thr Gln Lys Ser Leu Ser Leu Ser Pro Gly Lys
            690                 695

<210> SEQ ID NO 27
<211> LENGTH: 680
<212> TYPE: PRT
<213> ORGANISM: Artificial Sequence
<223> OTHER INFORMATION: "CD40L-wt + Seq 13 without Signal Peptide
      without Strep Tag "
<220> FEATURE:
<223> OTHER INFORMATION: CD40L-wt + Seq 13 without Signal Peptide
      without Strep Tag

<400> SEQUENCE: 27

Gln Ile Ala Ala His Val Ile Ser Glu Ala Ser Ser Lys Thr Thr Ser
1               5                   10                  15
Val Leu Gln Trp Ala Glu Lys Gly Tyr Tyr Thr Met Ser Asn Asn Leu
            20                  25                  30
Val Thr Leu Glu Asn Gly Lys Gln Leu Thr Val Lys Arg Gln Gly Leu
        35                  40                  45
Tyr Tyr Ile Tyr Ala Gln Val Thr Phe Cys Ser Asn Arg Glu Ala Ser
    50                  55                  60
Ser Gln Ala Pro Phe Ile Ala Ser Leu Cys Leu Lys Ser Pro Gly Arg
65                  70                  75                  80
Phe Glu Arg Ile Leu Leu Arg Ala Ala Asn Thr His Ser Ser Ala Lys
                85                  90                  95
Pro Cys Gly Gln Gln Ser Ile His Leu Gly Gly Val Phe Glu Leu Gln
            100                 105                 110
Pro Gly Ala Ser Val Phe Val Asn Val Thr Asp Pro Ser Gln Val Ser
        115                 120                 125
His Gly Thr Gly Phe Thr Ser Phe Gly Leu Leu Lys Leu Gly Ser Gly
    130                 135                 140
Ser Gly Asn Gly Ser Gln Ile Ala Ala His Val Ile Ser Glu Ala Ser
145                 150                 155                 160
```

-continued

```
Ser Lys Thr Thr Ser Val Leu Gln Trp Ala Glu Lys Gly Tyr Tyr Thr
                165                 170                 175
Met Ser Asn Asn Leu Val Thr Leu Glu Asn Gly Lys Gln Leu Thr Val
            180                 185                 190
Lys Arg Gln Gly Leu Tyr Tyr Ile Tyr Ala Gln Val Thr Phe Cys Ser
        195                 200                 205
Asn Arg Glu Ala Ser Ser Gln Ala Pro Phe Ile Ala Ser Leu Cys Leu
    210                 215                 220
Lys Ser Pro Gly Arg Phe Glu Arg Ile Leu Leu Arg Ala Ala Asn Thr
225                 230                 235                 240
His Ser Ser Ala Lys Pro Cys Gly Gln Gln Ser Ile His Leu Gly Gly
                245                 250                 255
Val Phe Glu Leu Gln Pro Gly Ala Ser Val Phe Val Asn Val Thr Asp
            260                 265                 270
Pro Ser Gln Val Ser His Gly Thr Gly Phe Thr Ser Phe Gly Leu Leu
        275                 280                 285
Lys Leu Gly Ser Gly Ser Asn Gly Ser Gln Ile Ala Ala His Val
    290                 295                 300
Ile Ser Glu Ala Ser Ser Lys Thr Thr Ser Val Leu Gln Trp Ala Glu
305                 310                 315                 320
Lys Gly Tyr Tyr Thr Met Ser Asn Asn Leu Val Thr Leu Glu Asn Gly
                325                 330                 335
Lys Gln Leu Thr Val Lys Arg Gln Gly Leu Tyr Tyr Ile Tyr Ala Gln
            340                 345                 350
Val Thr Phe Cys Ser Asn Arg Glu Ala Ser Ser Gln Ala Pro Phe Ile
        355                 360                 365
Ala Ser Leu Cys Leu Lys Ser Pro Gly Arg Phe Glu Arg Ile Leu Leu
    370                 375                 380
Arg Ala Ala Asn Thr His Ser Ser Ala Lys Pro Cys Gly Gln Gln Ser
385                 390                 395                 400
Ile His Leu Gly Gly Val Phe Glu Leu Gln Pro Gly Ala Ser Val Phe
                405                 410                 415
Val Asn Val Thr Asp Pro Ser Gln Val Ser His Gly Thr Gly Phe Thr
            420                 425                 430
Ser Phe Gly Leu Leu Lys Leu Gly Ser Gly Ser Ser Ser Ser Ser Ser
        435                 440                 445
Ser Ser Gly Ser Cys Asp Lys Thr His Thr Cys Pro Pro Cys Pro Ala
    450                 455                 460
Pro Glu Leu Leu Gly Gly Pro Ser Val Phe Leu Phe Pro Pro Lys Pro
465                 470                 475                 480
Lys Asp Thr Leu Met Ile Ser Arg Thr Pro Glu Val Thr Cys Val Val
                485                 490                 495
Val Asp Val Ser His Glu Asp Pro Glu Val Lys Phe Asn Trp Tyr Val
            500                 505                 510
Asp Gly Val Glu Val His Asn Ala Lys Thr Lys Pro Arg Glu Glu Gln
        515                 520                 525
Tyr Ser Ser Thr Tyr Arg Val Val Ser Val Leu Thr Val Leu His Gln
    530                 535                 540
Asp Trp Leu Asn Gly Lys Glu Tyr Lys Cys Lys Val Ser Asn Lys Ala
545                 550                 555                 560
Leu Pro Ala Pro Ile Glu Lys Thr Ile Ser Lys Ala Lys Gly Gln Pro
                565                 570                 575
Arg Glu Pro Gln Val Tyr Thr Leu Pro Pro Ser Arg Glu Glu Met Thr
```

```
                      580                 585                 590
Lys Asn Gln Val Ser Leu Thr Cys Leu Val Lys Gly Phe Tyr Pro Ser
                595                 600                 605

Asp Ile Ala Val Glu Trp Glu Ser Asn Gly Gln Pro Glu Asn Asn Tyr
        610                 615                 620

Lys Thr Thr Pro Pro Val Leu Asp Ser Asp Gly Ser Phe Phe Leu Tyr
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
        660                 665                 670

Ser Leu Ser Leu Ser Pro Gly Lys
        675                 680

<210> SEQ ID NO 28
<211> LENGTH: 694
<212> TYPE: PRT
<213> ORGANISM: Artificial Sequence
<223> OTHER INFORMATION: "fusion protein variant "
<220> FEATURE:
<223> OTHER INFORMATION: fusion protein variant

<400> SEQUENCE: 28

Gln Ile Ala Ala His Val Ile Ser Glu Ala Ser Ser Lys Thr Thr Ser
1               5                   10                  15

Val Leu Gln Trp Ala Glu Lys Gly Tyr Tyr Thr Met Ser Asn Asn Leu
                20                  25                  30

Val Thr Leu Glu Asn Gly Lys Gln Leu Thr Val Lys Arg Gln Gly Leu
        35                  40                  45

Tyr Tyr Ile Tyr Ala Gln Val Thr Phe Cys Ser Asn Arg Glu Ala Ser
    50                  55                  60

Ser Gln Ala Pro Phe Ile Ala Ser Leu Cys Leu Lys Ser Pro Gly Arg
65                  70                  75                  80

Phe Glu Arg Ile Leu Leu Arg Ala Ala Asn Thr His Ser Ser Ala Lys
                85                  90                  95

Pro Cys Gly Gln Gln Ser Ile His Leu Gly Gly Val Phe Glu Leu Gln
            100                 105                 110

Pro Gly Ala Ser Val Phe Val Asn Val Thr Asp Pro Ser Gln Val Ser
        115                 120                 125

His Gly Thr Gly Phe Thr Ser Phe Gly Leu Leu Lys Leu Gly Ser Gly
    130                 135                 140

Ser Gly Asn Gly Ser Gln Ile Ala Ala His Val Ile Ser Glu Ala Ser
145                 150                 155                 160

Ser Lys Thr Thr Ser Val Leu Gln Trp Ala Glu Lys Gly Tyr Tyr Thr
                165                 170                 175

Met Ser Asn Asn Leu Val Thr Leu Glu Asn Gly Lys Gln Leu Thr Val
            180                 185                 190

Lys Arg Gln Gly Leu Tyr Tyr Ile Tyr Ala Gln Val Thr Phe Cys Ser
        195                 200                 205

Asn Arg Glu Ala Ser Ser Gln Ala Pro Phe Ile Ala Ser Leu Cys Leu
    210                 215                 220

Lys Ser Pro Gly Arg Phe Glu Arg Ile Leu Leu Arg Ala Ala Asn Thr
225                 230                 235                 240

His Ser Ser Ala Lys Pro Cys Gly Gln Gln Ser Ile His Leu Gly Gly
                245                 250                 255
```

-continued

Val Phe Glu Leu Gln Pro Gly Ala Ser Val Phe Val Asn Val Thr Asp
            260                 265                 270

Pro Ser Gln Val Ser His Gly Thr Gly Phe Thr Ser Phe Gly Leu Leu
        275                 280                 285

Lys Leu Gly Ser Gly Ser Gly Asn Gly Ser Gln Ile Ala Ala His Val
    290                 295                 300

Ile Ser Glu Ala Ser Ser Lys Thr Thr Ser Val Leu Gln Trp Ala Glu
305                 310                 315                 320

Lys Gly Tyr Tyr Thr Met Ser Asn Asn Leu Val Thr Leu Glu Asn Gly
            325                 330                 335

Lys Gln Leu Thr Val Lys Arg Gln Gly Leu Tyr Tyr Ile Tyr Ala Gln
        340                 345                 350

Val Thr Phe Cys Ser Asn Arg Glu Ala Ser Ser Gln Ala Pro Phe Ile
    355                 360                 365

Ala Ser Leu Cys Leu Lys Ser Pro Gly Arg Phe Glu Arg Ile Leu Leu
370                 375                 380

Arg Ala Ala Asn Thr His Ser Ser Ala Lys Pro Cys Gly Gln Gln Ser
385                 390                 395                 400

Ile His Leu Gly Gly Val Phe Glu Leu Gln Pro Gly Ala Ser Val Phe
            405                 410                 415

Val Asn Val Thr Asp Pro Ser Gln Val Ser His Gly Thr Gly Phe Thr
        420                 425                 430

Ser Phe Gly Leu Leu Lys Leu Gly Ser Gly Ser Ser Ser Ser Ser Ser
    435                 440                 445

Ser Ser Gly Ser Cys Asp Lys Thr His Thr Cys Pro Pro Cys Pro Ala
450                 455                 460

Pro Glu Leu Leu Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
            485                 490                 495

Val Asp Val Ser His Glu Asp Pro Glu Val Lys Phe Asn Trp Tyr Val
        500                 505                 510

Asp Gly Val Glu Val His Asn Ala Lys Thr Lys Pro Arg Glu Glu Gln
    515                 520                 525

Tyr Ser Ser Thr Tyr Arg Val Val Ser Val Leu Thr Val Leu His Gln
530                 535                 540

Asp Trp Leu Asn Gly Lys Glu Tyr Lys Cys Lys Val Ser Asn Lys Ala
545                 550                 555                 560

Leu Pro Ala Pro Ile Glu Lys Thr Ile Ser Lys Ala Lys Gly Gln Pro
            565                 570                 575

Arg Glu Pro Gln Val Tyr Thr Leu Pro Pro Ser Arg Glu Glu Met Thr
        580                 585                 590

Lys Asn Gln Val Ser Leu Thr Cys Leu Val Lys Gly Phe Tyr Pro Ser
    595                 600                 605

Asp Ile Ala Val Glu Trp Glu Ser Asn Gly Gln Pro Glu Asn Asn Tyr
610                 615                 620

Lys Thr Thr Pro Pro Val Leu Asp Ser Asp Gly Ser Phe Phe Leu Tyr
625                 630                 635                 640

Ser Lys Leu Thr Val Asp Lys Ser Arg Trp Gln Gln Gly Asn Val Phe
            645                 650                 655

Ser Cys Ser Val Met His Glu Ala Leu His Asn His Tyr Thr Gln Lys
        660                 665                 670

Ser Leu Ser Leu Ser Pro Gly Ser Ser Ser Ser Ser Ser Ala Trp Ser

His Pro Gln Phe Glu Lys
                690

<210> SEQ ID NO 29
<211> LENGTH: 679
<212> TYPE: PRT
<213> ORGANISM: Artificial Sequence
<220> FEATURE:
<223> OTHER INFORMATION: "fusion protein variant"
<220> FEATURE:
<223> OTHER INFORMATION: fusion protein variant

<400> SEQUENCE: 29

Gln Ile Ala Ala His Val Ile Ser Glu Ala Ser Ser Lys Thr Thr Ser
1               5                   10                  15

Val Leu Gln Trp Ala Glu Lys Gly Tyr Tyr Thr Met Ser Asn Asn Leu
            20                  25                  30

Val Thr Leu Glu Asn Gly Lys Gln Leu Thr Val Lys Arg Gln Gly Leu
        35                  40                  45

Tyr Tyr Ile Tyr Ala Gln Val Thr Phe Cys Ser Asn Arg Glu Ala Ser
    50                  55                  60

Ser Gln Ala Pro Phe Ile Ala Ser Leu Cys Leu Lys Ser Pro Gly Arg
65                  70                  75                  80

Phe Glu Arg Ile Leu Leu Arg Ala Ala Asn Thr His Ser Ser Ala Lys
                85                  90                  95

Pro Cys Gly Gln Gln Ser Ile His Leu Gly Gly Val Phe Glu Leu Gln
            100                 105                 110

Pro Gly Ala Ser Val Phe Val Asn Val Thr Asp Pro Ser Gln Val Ser
        115                 120                 125

His Gly Thr Gly Phe Thr Ser Phe Gly Leu Leu Lys Leu Gly Ser Gly
    130                 135                 140

Ser Gly Asn Gly Ser Gln Ile Ala Ala His Val Ile Ser Glu Ala Ser
145                 150                 155                 160

Ser Lys Thr Thr Ser Val Leu Gln Trp Ala Glu Lys Gly Tyr Tyr Thr
                165                 170                 175

Met Ser Asn Asn Leu Val Thr Leu Glu Asn Gly Lys Gln Leu Thr Val
            180                 185                 190

Lys Arg Gln Gly Leu Tyr Tyr Ile Tyr Ala Gln Val Thr Phe Cys Ser
        195                 200                 205

Asn Arg Glu Ala Ser Ser Gln Ala Pro Phe Ile Ala Ser Leu Cys Leu
    210                 215                 220

Lys Ser Pro Gly Arg Phe Glu Arg Ile Leu Leu Arg Ala Ala Asn Thr
225                 230                 235                 240

His Ser Ser Ala Lys Pro Cys Gly Gln Gln Ser Ile His Leu Gly Gly
                245                 250                 255

Val Phe Glu Leu Gln Pro Gly Ala Ser Val Phe Val Asn Val Thr Asp
            260                 265                 270

Pro Ser Gln Val Ser His Gly Thr Gly Phe Thr Ser Phe Gly Leu Leu
        275                 280                 285

Lys Leu Gly Ser Gly Ser Gly Asn Gly Ser Gln Ile Ala Ala His Val
    290                 295                 300

Ile Ser Glu Ala Ser Ser Lys Thr Thr Ser Val Leu Gln Trp Ala Glu
305                 310                 315                 320

Lys Gly Tyr Tyr Thr Met Ser Asn Asn Leu Val Thr Leu Glu Asn Gly
                325                 330                 335

```
Lys Gln Leu Thr Val Lys Arg Gln Gly Leu Tyr Tyr Ile Tyr Ala Gln
            340                 345                 350
Val Thr Phe Cys Ser Asn Arg Glu Ala Ser Ser Gln Ala Pro Phe Ile
        355                 360                 365
Ala Ser Leu Cys Leu Lys Ser Pro Gly Arg Phe Glu Arg Ile Leu Leu
    370                 375                 380
Arg Ala Ala Asn Thr His Ser Ala Lys Pro Cys Gly Gln Gln Ser
385                 390                 395                 400
Ile His Leu Gly Gly Val Phe Glu Leu Gln Pro Gly Ala Ser Val Phe
                405                 410                 415
Val Asn Val Thr Asp Pro Ser Gln Val Ser His Gly Thr Gly Phe Thr
            420                 425                 430
Ser Phe Gly Leu Leu Lys Leu Gly Ser Gly Ser Ser Ser Ser Ser
        435                 440                 445
Ser Ser Gly Ser Cys Asp Lys Thr His Thr Cys Pro Pro Cys Pro Ala
    450                 455                 460
Pro Pro Val Ala Gly Pro Ser Val Phe Leu Phe Pro Pro Lys Pro Lys
465                 470                 475                 480
Asp Thr Leu Met Ile Ser Arg Thr Pro Glu Val Thr Cys Val Val Val
                485                 490                 495
Asp Val Ser His Glu Asp Pro Glu Val Lys Phe Asn Trp Tyr Val Asp
            500                 505                 510
Gly Val Glu Val His Asn Ala Lys Thr Lys Pro Arg Glu Glu Gln Tyr
        515                 520                 525
Asn Ser Thr Tyr Arg Val Val Ser Val Leu Thr Val Leu His Gln Asp
    530                 535                 540
Trp Leu Asn Gly Lys Glu Tyr Lys Cys Lys Val Ser Asn Lys Gly Leu
545                 550                 555                 560
Pro Ser Ser Ile Glu Lys Thr Ile Ser Lys Ala Lys Gly Gln Pro Arg
                565                 570                 575
Glu Pro Gln Val Tyr Thr Leu Pro Pro Ser Arg Glu Glu Met Thr Lys
            580                 585                 590
Asn Gln Val Ser Leu Thr Cys Leu Val Lys Gly Phe Tyr Pro Ser Asp
        595                 600                 605
Ile Ala Val Glu Trp Glu Ser Asn Gly Gln Pro Glu Asn Asn Tyr Lys
    610                 615                 620
Thr Thr Pro Pro Val Leu Asp Ser Asp Gly Ser Phe Phe Leu Tyr Ser
625                 630                 635                 640
Lys Leu Thr Val Asp Lys Ser Arg Trp Gln Gln Gly Asn Val Phe Ser
                645                 650                 655
Cys Ser Val Met His Glu Ala Leu His Asn His Tyr Thr Gln Lys Ser
            660                 665                 670
Leu Ser Leu Ser Pro Gly Lys
        675

<210> SEQ ID NO 30
<211> LENGTH: 693
<212> TYPE: PRT
<213> ORGANISM: Artificial Sequence
<223> OTHER INFORMATION: "fusion protein variant"
<220> FEATURE:
<223> OTHER INFORMATION: fusion protein variant

<400> SEQUENCE: 30

Gln Ile Ala Ala His Val Ile Ser Glu Ala Ser Ser Lys Thr Thr Ser
1               5                   10                  15
```

```
Val Leu Gln Trp Ala Glu Lys Gly Tyr Tyr Thr Met Ser Asn Asn Leu
             20                  25                  30

Val Thr Leu Glu Asn Gly Lys Gln Leu Thr Val Lys Arg Gln Gly Leu
         35                  40                  45

Tyr Tyr Ile Tyr Ala Gln Val Thr Phe Cys Ser Asn Arg Glu Ala Ser
 50                  55                  60

Ser Gln Ala Pro Phe Ile Ala Ser Leu Cys Leu Lys Ser Pro Gly Arg
 65                  70                  75                  80

Phe Glu Arg Ile Leu Leu Arg Ala Ala Asn Thr His Ser Ser Ala Lys
             85                  90                  95

Pro Cys Gly Gln Gln Ser Ile His Leu Gly Gly Val Phe Glu Leu Gln
             100                 105                 110

Pro Gly Ala Ser Val Phe Val Asn Val Thr Asp Pro Ser Gln Val Ser
             115                 120                 125

His Gly Thr Gly Phe Thr Ser Phe Gly Leu Leu Lys Leu Gly Ser Gly
             130                 135                 140

Ser Gly Asn Gly Ser Gln Ile Ala Ala His Val Ile Ser Glu Ala Ser
145                 150                 155                 160

Ser Lys Thr Thr Ser Val Leu Gln Trp Ala Glu Lys Gly Tyr Tyr Thr
                 165                 170                 175

Met Ser Asn Asn Leu Val Thr Leu Glu Asn Gly Lys Gln Leu Thr Val
             180                 185                 190

Lys Arg Gln Gly Leu Tyr Tyr Ile Tyr Ala Gln Val Thr Phe Cys Ser
             195                 200                 205

Asn Arg Glu Ala Ser Ser Gln Ala Pro Phe Ile Ala Ser Leu Cys Leu
             210                 215                 220

Lys Ser Pro Gly Arg Phe Glu Arg Ile Leu Leu Arg Ala Ala Asn Thr
225                 230                 235                 240

His Ser Ser Ala Lys Pro Cys Gly Gln Gln Ser Ile His Leu Gly Gly
                 245                 250                 255

Val Phe Glu Leu Gln Pro Gly Ala Ser Val Phe Val Asn Val Thr Asp
             260                 265                 270

Pro Ser Gln Val Ser His Gly Thr Gly Phe Thr Ser Phe Gly Leu Leu
             275                 280                 285

Lys Leu Gly Ser Gly Ser Gly Asn Gly Ser Gln Ile Ala Ala His Val
             290                 295                 300

Ile Ser Glu Ala Ser Ser Lys Thr Thr Ser Val Leu Gln Trp Ala Glu
305                 310                 315                 320

Lys Gly Tyr Tyr Thr Met Ser Asn Asn Leu Val Thr Leu Glu Asn Gly
                 325                 330                 335

Lys Gln Leu Thr Val Lys Arg Gln Gly Leu Tyr Tyr Ile Tyr Ala Gln
             340                 345                 350

Val Thr Phe Cys Ser Asn Arg Glu Ala Ser Ser Gln Ala Pro Phe Ile
             355                 360                 365

Ala Ser Leu Cys Leu Lys Ser Pro Gly Arg Phe Glu Arg Ile Leu Leu
             370                 375                 380

Arg Ala Ala Asn Thr His Ser Ser Ala Lys Pro Cys Gly Gln Gln Ser
385                 390                 395                 400

Ile His Leu Gly Gly Val Phe Glu Leu Gln Pro Gly Ala Ser Val Phe
                 405                 410                 415

Val Asn Val Thr Asp Pro Ser Gln Val Ser His Gly Thr Gly Phe Thr
             420                 425                 430
```

```
Ser Phe Gly Leu Leu Lys Leu Gly Ser Gly Ser Ser Ser Ser Ser
            435                 440                 445

Ser Ser Gly Ser Cys Asp Lys Thr His Thr Cys Pro Pro Cys Pro Ala
450                 455                 460

Pro Pro Val Ala Gly Pro Ser Val Phe Leu Phe Pro Pro Lys Pro Lys
465                 470                 475                 480

Asp Thr Leu Met Ile Ser Arg Thr Pro Glu Val Thr Cys Val Val Val
                485                 490                 495

Asp Val Ser His Glu Asp Pro Glu Val Lys Phe Asn Trp Tyr Val Asp
            500                 505                 510

Gly Val Glu Val His Asn Ala Lys Thr Lys Pro Arg Glu Glu Gln Tyr
            515                 520                 525

Asn Ser Thr Tyr Arg Val Val Ser Val Leu Thr Val Leu His Gln Asp
530                 535                 540

Trp Leu Asn Gly Lys Glu Tyr Lys Cys Lys Val Ser Asn Lys Gly Leu
545                 550                 555                 560

Pro Ser Ser Ile Glu Lys Thr Ile Ser Lys Ala Lys Gly Gln Pro Arg
                565                 570                 575

Glu Pro Gln Val Tyr Thr Leu Pro Pro Ser Arg Glu Glu Met Thr Lys
            580                 585                 590

Asn Gln Val Ser Leu Thr Cys Leu Val Lys Gly Phe Tyr Pro Ser Asp
            595                 600                 605

Ile Ala Val Glu Trp Glu Ser Asn Gly Gln Pro Glu Asn Asn Tyr Lys
        610                 615                 620

Thr Thr Pro Pro Val Leu Asp Ser Asp Gly Ser Phe Phe Leu Tyr Ser
625                 630                 635                 640

Lys Leu Thr Val Asp Lys Ser Arg Trp Gln Gln Gly Asn Val Phe Ser
                645                 650                 655

Cys Ser Val Met His Glu Ala Leu His Asn His Tyr Thr Gln Lys Ser
                660                 665                 670

Leu Ser Leu Ser Pro Gly Ser Ser Ser Ser Ser Ala Trp Ser His
            675                 680                 685

Pro Gln Phe Glu Lys
    690

<210> SEQ ID NO 31
<211> LENGTH: 714
<212> TYPE: PRT
<213> ORGANISM: Artificial Sequence
<223> OTHER INFORMATION: "Protein-B"
<220> FEATURE:
<223> OTHER INFORMATION: Protein-B

<400> SEQUENCE: 31

Met Glu Thr Asp Thr Leu Leu Val Phe Val Leu Leu Val Trp Val Pro
1               5                   10                  15

Ala Gly Asn Gly Gln Ile Ala Ala His Val Ile Ser Glu Ala Ser Ser
            20                  25                  30

Lys Thr Thr Ser Val Leu Gln Trp Ala Glu Lys Gly Tyr Tyr Thr Met
        35                  40                  45

Ser Asn Asn Leu Val Thr Leu Glu Asn Gly Lys Gln Leu Thr Val Lys
    50                  55                  60

Arg Gln Gly Leu Tyr Tyr Ile Tyr Ala Gln Val Thr Phe Cys Ser Asn
65                  70                  75                  80

Arg Glu Ala Ser Ser Gln Ala Pro Phe Ile Ala Ser Leu Ser Leu Lys
                85                  90                  95
```

```
Ser Pro Gly Arg Phe Glu Arg Ile Leu Leu Arg Ala Ala Asn Thr His
            100                 105                 110

Ser Ser Ala Lys Pro Cys Gly Gln Gln Ser Ile His Leu Gly Gly Val
            115                 120                 125

Phe Glu Leu Gln Pro Gly Ala Ser Val Phe Val Asn Val Thr Asp Pro
            130                 135                 140

Ser Gln Val Ser His Gly Thr Gly Phe Thr Ser Phe Gly Leu Leu Lys
145                 150                 155                 160

Leu Gly Ser Gly Ser Gly Asn Gly Ser Gln Ile Ala Ala His Val Ile
                165                 170                 175

Ser Glu Ala Ser Ser Lys Thr Thr Ser Val Leu Gln Trp Ala Glu Lys
            180                 185                 190

Gly Tyr Tyr Thr Met Ser Asn Asn Leu Val Thr Leu Glu Asn Gly Lys
            195                 200                 205

Gln Leu Thr Val Lys Arg Gln Gly Leu Tyr Tyr Ile Tyr Ala Gln Val
            210                 215                 220

Thr Phe Cys Ser Asn Arg Glu Ala Ser Ser Gln Ala Pro Phe Ile Ala
225                 230                 235                 240

Ser Leu Ser Leu Lys Ser Pro Gly Arg Phe Glu Arg Ile Leu Leu Arg
                245                 250                 255

Ala Ala Asn Thr His Ser Ser Ala Lys Pro Cys Gly Gln Gln Ser Ile
            260                 265                 270

His Leu Gly Gly Val Phe Glu Leu Gln Pro Gly Ala Ser Val Phe Val
            275                 280                 285

Asn Val Thr Asp Pro Ser Gln Val Ser His Gly Thr Gly Phe Thr Ser
            290                 295                 300

Phe Gly Leu Leu Lys Leu Gly Ser Gly Ser Gly Asn Gly Ser Gln Ile
305                 310                 315                 320

Ala Ala His Val Ile Ser Glu Ala Ser Ser Lys Thr Thr Ser Val Leu
                325                 330                 335

Gln Trp Ala Glu Lys Gly Tyr Tyr Thr Met Ser Asn Asn Leu Val Thr
            340                 345                 350

Leu Glu Asn Gly Lys Gln Leu Thr Val Lys Arg Gln Gly Leu Tyr Tyr
            355                 360                 365

Ile Tyr Ala Gln Val Thr Phe Cys Ser Asn Arg Glu Ala Ser Ser Gln
            370                 375                 380

Ala Pro Phe Ile Ala Ser Leu Ser Leu Lys Ser Pro Gly Arg Phe Glu
385                 390                 395                 400

Arg Ile Leu Leu Arg Ala Ala Asn Thr His Ser Ser Ala Lys Pro Cys
                405                 410                 415

Gly Gln Gln Ser Ile His Leu Gly Gly Val Phe Glu Leu Gln Pro Gly
            420                 425                 430

Ala Ser Val Phe Val Asn Val Thr Asp Pro Ser Gln Val Ser His Gly
            435                 440                 445

Thr Gly Phe Thr Ser Phe Gly Leu Leu Lys Leu Gly Ser Gly Ser Ser
            450                 455                 460

Ser Ser Ser Ser Ser Ser Gly Ser Cys Asp Lys Thr His Thr Cys Pro
465                 470                 475                 480

Pro Cys Pro Ala Pro Glu Leu Leu Gly Gly Pro Ser Val Phe Leu Phe
                485                 490                 495

Pro Pro Lys Pro Lys Asp Thr Leu Met Ile Ser Arg Thr Pro Glu Val
            500                 505                 510
```

```
Thr Cys Val Val Asp Val Ser His Glu Asp Pro Glu Val Lys Phe
            515                 520                 525

Asn Trp Tyr Val Asp Gly Val Glu Val His Asn Ala Lys Thr Lys Pro
530                 535                 540

Arg Glu Glu Gln Tyr Ser Ser Thr Tyr Arg Val Val Ser Val Leu Thr
545                 550                 555                 560

Val Leu His Gln Asp Trp Leu Asn Gly Lys Glu Tyr Lys Cys Lys Val
                565                 570                 575

Ser Asn Lys Ala Leu Pro Ala Pro Ile Glu Lys Thr Ile Ser Lys Ala
            580                 585                 590

Lys Gly Gln Pro Arg Glu Pro Gln Val Tyr Thr Leu Pro Pro Ser Arg
595                 600                 605

Glu Glu Met Thr Lys Asn Gln Val Ser Leu Thr Cys Leu Val Lys Gly
610                 615                 620

Phe Tyr Pro Ser Asp Ile Ala Val Glu Trp Glu Ser Asn Gly Gln Pro
625                 630                 635                 640

Glu Asn Asn Tyr Lys Thr Thr Pro Pro Val Leu Asp Ser Asp Gly Ser
            645                 650                 655

Phe Phe Leu Tyr Ser Lys Leu Thr Val Asp Lys Ser Arg Trp Gln Gln
                660                 665                 670

Gly Asn Val Phe Ser Cys Ser Val Met His Glu Ala Leu His Asn His
            675                 680                 685

Tyr Thr Gln Lys Ser Leu Ser Leu Ser Pro Gly Ser Ser Ser Ser
            690                 695                 700

Ser Ala Trp Ser His Pro Gln Phe Glu Lys
705                 710

<210> SEQ ID NO 32
<211> LENGTH: 694
<212> TYPE: PRT
<213> ORGANISM: Artificial Sequence
<223> OTHER INFORMATION: "Protein-B without Signal Peptide"
<220> FEATURE:
<223> OTHER INFORMATION: Protein-B without Signal Peptide

<400> SEQUENCE: 32

Gln Ile Ala Ala His Val Ile Ser Glu Ala Ser Ser Lys Thr Thr Ser
1               5                   10                  15

Val Leu Gln Trp Ala Glu Lys Gly Tyr Tyr Thr Met Ser Asn Asn Leu
            20                  25                  30

Val Thr Leu Glu Asn Gly Lys Gln Leu Thr Val Lys Arg Gln Gly Leu
        35                  40                  45

Tyr Tyr Ile Tyr Ala Gln Val Thr Phe Cys Ser Asn Arg Glu Ala Ser
    50                  55                  60

Ser Gln Ala Pro Phe Ile Ala Ser Leu Ser Lys Ser Pro Gly Arg
65                  70                  75                  80

Phe Glu Arg Ile Leu Leu Arg Ala Ala Asn Thr His Ser Ser Ala Lys
                85                  90                  95

Pro Cys Gly Gln Gln Ser Ile His Leu Gly Gly Val Phe Glu Leu Gln
            100                 105                 110

Pro Gly Ala Ser Val Phe Val Asn Val Thr Asp Pro Ser Gln Val Ser
        115                 120                 125

His Gly Thr Gly Phe Thr Ser Phe Gly Leu Leu Lys Leu Gly Ser Gly
    130                 135                 140

Ser Gly Asn Gly Ser Gln Ile Ala Ala His Val Ile Ser Glu Ala Ser
145                 150                 155                 160
```

```
Ser Lys Thr Thr Ser Val Leu Gln Trp Ala Glu Lys Gly Tyr Tyr Thr
            165                 170                 175

Met Ser Asn Asn Leu Val Thr Leu Glu Asn Gly Lys Gln Leu Thr Val
            180                 185                 190

Lys Arg Gln Gly Leu Tyr Tyr Ile Tyr Ala Gln Val Thr Phe Cys Ser
            195                 200                 205

Asn Arg Glu Ala Ser Ser Gln Ala Pro Phe Ile Ala Ser Leu Ser Leu
            210                 215                 220

Lys Ser Pro Gly Arg Phe Glu Arg Ile Leu Leu Arg Ala Ala Asn Thr
225                 230                 235                 240

His Ser Ser Ala Lys Pro Cys Gly Gln Gln Ser Ile His Leu Gly Gly
            245                 250                 255

Val Phe Glu Leu Gln Pro Gly Ala Ser Val Phe Val Asn Val Thr Asp
            260                 265                 270

Pro Ser Gln Val Ser His Gly Thr Gly Phe Thr Ser Phe Gly Leu Leu
            275                 280                 285

Lys Leu Gly Ser Gly Ser Gly Asn Gly Ser Gln Ile Ala Ala His Val
            290                 295                 300

Ile Ser Glu Ala Ser Ser Lys Thr Thr Ser Val Leu Gln Trp Ala Glu
305                 310                 315                 320

Lys Gly Tyr Tyr Thr Met Ser Asn Asn Leu Val Thr Leu Glu Asn Gly
            325                 330                 335

Lys Gln Leu Thr Val Lys Arg Gln Gly Leu Tyr Tyr Ile Tyr Ala Gln
            340                 345                 350

Val Thr Phe Cys Ser Asn Arg Glu Ala Ser Ser Gln Ala Pro Phe Ile
            355                 360                 365

Ala Ser Leu Ser Leu Lys Ser Pro Gly Arg Phe Glu Arg Ile Leu Leu
            370                 375                 380

Arg Ala Ala Asn Thr His Ser Ser Ala Lys Pro Cys Gly Gln Gln Ser
385                 390                 395                 400

Ile His Leu Gly Gly Val Phe Glu Leu Gln Pro Gly Ala Ser Val Phe
            405                 410                 415

Val Asn Val Thr Asp Pro Ser Gln Val Ser His Gly Thr Gly Phe Thr
            420                 425                 430

Ser Phe Gly Leu Leu Lys Leu Gly Ser Gly Ser Ser Ser Ser Ser Ser
            435                 440                 445

Ser Ser Gly Ser Cys Asp Lys Thr His Thr Cys Pro Pro Cys Pro Ala
450                 455                 460

Pro Glu Leu Leu Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
            485                 490                 495

Val Asp Val Ser His Glu Asp Pro Glu Val Lys Phe Asn Trp Tyr Val
            500                 505                 510

Asp Gly Val Glu Val His Asn Ala Lys Thr Lys Pro Arg Glu Glu Gln
            515                 520                 525

Tyr Ser Ser Thr Tyr Arg Val Val Ser Val Leu Thr Val Leu His Gln
            530                 535                 540

Asp Trp Leu Asn Gly Lys Glu Tyr Lys Cys Lys Val Ser Asn Lys Ala
545                 550                 555                 560

Leu Pro Ala Pro Ile Glu Lys Thr Ile Ser Lys Ala Lys Gly Gln Pro
            565                 570                 575
```

```
Arg Glu Pro Gln Val Tyr Thr Leu Pro Pro Ser Arg Glu Glu Met Thr
                580                 585                 590

Lys Asn Gln Val Ser Leu Thr Cys Leu Val Lys Gly Phe Tyr Pro Ser
            595                 600                 605

Asp Ile Ala Val Glu Trp Glu Ser Asn Gly Gln Pro Glu Asn Asn Tyr
        610                 615                 620

Lys Thr Thr Pro Pro Val Leu Asp Ser Asp Gly Ser Phe Phe Leu Tyr
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
            660                 665                 670

Ser Leu Ser Leu Ser Pro Gly Ser Ser Ser Ser Ser Ala Trp Ser
        675                 680                 685

His Pro Gln Phe Glu Lys
    690

<210> SEQ ID NO 33
<211> LENGTH: 700
<212> TYPE: PRT
<213> ORGANISM: Artificial Sequence
<223> OTHER INFORMATION: "Protein-B without Strep Tag"
<220> FEATURE:
<223> OTHER INFORMATION: Protein-B without Strep Tag

<400> SEQUENCE: 33

Met Glu Thr Asp Thr Leu Leu Val Phe Val Leu Leu Val Trp Val Pro
1               5                   10                  15

Ala Gly Asn Gly Gln Ile Ala Ala His Val Ile Ser Glu Ala Ser Ser
                20                  25                  30

Lys Thr Thr Ser Val Leu Gln Trp Ala Glu Lys Gly Tyr Tyr Thr Met
            35                  40                  45

Ser Asn Asn Leu Val Thr Leu Glu Asn Gly Lys Gln Leu Thr Val Lys
        50                  55                  60

Arg Gln Gly Leu Tyr Tyr Ile Tyr Ala Gln Val Thr Phe Cys Ser Asn
65                  70                  75                  80

Arg Glu Ala Ser Ser Gln Ala Pro Phe Ile Ala Ser Leu Ser Leu Lys
                85                  90                  95

Ser Pro Gly Arg Phe Glu Arg Ile Leu Leu Arg Ala Ala Asn Thr His
            100                 105                 110

Ser Ser Ala Lys Pro Cys Gly Gln Gln Ser Ile His Leu Gly Gly Val
        115                 120                 125

Phe Glu Leu Gln Pro Gly Ala Ser Val Phe Val Asn Val Thr Asp Pro
    130                 135                 140

Ser Gln Val Ser His Gly Thr Gly Phe Thr Ser Phe Gly Leu Leu Lys
145                 150                 155                 160

Leu Gly Ser Gly Ser Gly Asn Gly Ser Gln Ile Ala Ala His Val Ile
                165                 170                 175

Ser Glu Ala Ser Ser Lys Thr Thr Ser Val Leu Gln Trp Ala Glu Lys
            180                 185                 190

Gly Tyr Tyr Thr Met Ser Asn Asn Leu Val Thr Leu Glu Asn Gly Lys
        195                 200                 205

Gln Leu Thr Val Lys Arg Gln Gly Leu Tyr Tyr Ile Tyr Ala Gln Val
    210                 215                 220

Thr Phe Cys Ser Asn Arg Glu Ala Ser Ser Gln Ala Pro Phe Ile Ala
225                 230                 235                 240
```

```
Ser Leu Ser Leu Lys Ser Pro Gly Arg Phe Glu Arg Ile Leu Leu Arg
            245                 250                 255

Ala Ala Asn Thr His Ser Ser Ala Lys Pro Cys Gly Gln Gln Ser Ile
            260                 265                 270

His Leu Gly Gly Val Phe Glu Leu Gln Pro Gly Ala Ser Val Phe Val
            275                 280                 285

Asn Val Thr Asp Pro Ser Gln Val Ser His Gly Thr Gly Phe Thr Ser
        290                 295                 300

Phe Gly Leu Leu Lys Leu Gly Ser Gly Ser Asn Gly Ser Gln Ile
305             310                 315                 320

Ala Ala His Val Ile Ser Glu Ala Ser Ser Lys Thr Thr Ser Val Leu
                325                 330                 335

Gln Trp Ala Glu Lys Gly Tyr Tyr Thr Met Ser Asn Asn Leu Val Thr
            340                 345                 350

Leu Glu Asn Gly Lys Gln Leu Thr Val Lys Arg Gln Gly Leu Tyr Tyr
            355                 360                 365

Ile Tyr Ala Gln Val Thr Phe Cys Ser Asn Arg Glu Ala Ser Ser Gln
        370                 375                 380

Ala Pro Phe Ile Ala Ser Leu Ser Leu Lys Ser Pro Gly Arg Phe Glu
385             390                 395                 400

Arg Ile Leu Leu Arg Ala Ala Asn Thr His Ser Ser Ala Lys Pro Cys
                405                 410                 415

Gly Gln Gln Ser Ile His Leu Gly Gly Val Phe Glu Leu Gln Pro Gly
            420                 425                 430

Ala Ser Val Phe Val Asn Val Thr Asp Pro Ser Gln Val Ser His Gly
            435                 440                 445

Thr Gly Phe Thr Ser Phe Gly Leu Leu Lys Leu Gly Ser Gly Ser Ser
        450                 455                 460

Ser Ser Ser Ser Ser Ser Gly Ser Cys Asp Lys Thr His Thr Cys Pro
465                 470                 475                 480

Pro Cys Pro Ala Pro Glu Leu Leu Gly Gly Pro Ser Val Phe Leu Phe
            485                 490                 495

Pro Pro Lys Pro Lys Asp Thr Leu Met Ile Ser Arg Thr Pro Glu Val
            500                 505                 510

Thr Cys Val Val Val Asp Val Ser His Glu Asp Pro Glu Val Lys Phe
        515                 520                 525

Asn Trp Tyr Val Asp Gly Val Glu Val His Asn Ala Lys Thr Lys Pro
        530                 535                 540

Arg Glu Glu Gln Tyr Ser Ser Thr Tyr Arg Val Val Ser Val Leu Thr
545                 550                 555                 560

Val Leu His Gln Asp Trp Leu Asn Gly Lys Glu Tyr Lys Cys Lys Val
                565                 570                 575

Ser Asn Lys Ala Leu Pro Ala Pro Ile Glu Lys Thr Ile Ser Lys Ala
            580                 585                 590

Lys Gly Gln Pro Arg Glu Pro Gln Val Tyr Thr Leu Pro Pro Ser Arg
            595                 600                 605

Glu Glu Met Thr Lys Asn Gln Val Ser Leu Thr Cys Leu Val Lys Gly
            610                 615                 620

Phe Tyr Pro Ser Asp Ile Ala Val Glu Trp Glu Ser Asn Gly Gln Pro
625                 630                 635                 640

Glu Asn Asn Tyr Lys Thr Thr Pro Pro Val Leu Asp Ser Asp Gly Ser
                645                 650                 655
```

```
Phe Phe Leu Tyr Ser Lys Leu Thr Val Asp Lys Ser Arg Trp Gln Gln
            660                 665                 670

Gly Asn Val Phe Ser Cys Ser Val Met His Glu Ala Leu His Asn His
            675                 680                 685

Tyr Thr Gln Lys Ser Leu Ser Leu Ser Pro Gly Lys
        690                 695                 700

<210> SEQ ID NO 34
<211> LENGTH: 680
<212> TYPE: PRT
<213> ORGANISM: Artificial Sequence
<223> OTHER INFORMATION: "Protein-B witout Signal Peptide without Strep
      Tag"
<220> FEATURE:
<223> OTHER INFORMATION: Protein-B witout Signal Peptide without Strep
      Tag

<400> SEQUENCE: 34

Gln Ile Ala Ala His Val Ile Ser Glu Ala Ser Ser Lys Thr Thr Ser
1               5                   10                  15

Val Leu Gln Trp Ala Glu Lys Gly Tyr Tyr Thr Met Ser Asn Asn Leu
            20                  25                  30

Val Thr Leu Glu Asn Gly Lys Gln Leu Thr Val Lys Arg Gln Gly Leu
        35                  40                  45

Tyr Tyr Ile Tyr Ala Gln Val Thr Phe Cys Ser Asn Arg Glu Ala Ser
    50                  55                  60

Ser Gln Ala Pro Phe Ile Ala Ser Leu Ser Leu Lys Ser Pro Gly Arg
65                  70                  75                  80

Phe Glu Arg Ile Leu Leu Arg Ala Ala Asn Thr His Ser Ser Ala Lys
                85                  90                  95

Pro Cys Gly Gln Gln Ser Ile His Leu Gly Gly Val Phe Glu Leu Gln
            100                 105                 110

Pro Gly Ala Ser Val Phe Val Asn Val Thr Asp Pro Ser Gln Val Ser
        115                 120                 125

His Gly Thr Gly Phe Thr Ser Phe Gly Leu Leu Lys Leu Gly Ser Gly
    130                 135                 140

Ser Gly Asn Gly Ser Gln Ile Ala Ala His Val Ile Ser Glu Ala Ser
145                 150                 155                 160

Ser Lys Thr Thr Ser Val Leu Gln Trp Ala Glu Lys Gly Tyr Tyr Thr
                165                 170                 175

Met Ser Asn Asn Leu Val Thr Leu Glu Asn Gly Lys Gln Leu Thr Val
            180                 185                 190

Lys Arg Gln Gly Leu Tyr Tyr Ile Tyr Ala Gln Val Thr Phe Cys Ser
        195                 200                 205

Asn Arg Glu Ala Ser Ser Gln Ala Pro Phe Ile Ala Ser Leu Ser Leu
    210                 215                 220

Lys Ser Pro Gly Arg Phe Glu Arg Ile Leu Leu Arg Ala Ala Asn Thr
225                 230                 235                 240

His Ser Ser Ala Lys Pro Cys Gly Gln Gln Ser Ile His Leu Gly Gly
                245                 250                 255

Val Phe Glu Leu Gln Pro Gly Ala Ser Val Phe Val Asn Val Thr Asp
            260                 265                 270

Pro Ser Gln Val Ser His Gly Thr Gly Phe Thr Ser Phe Gly Leu Leu
        275                 280                 285

Lys Leu Gly Ser Gly Ser Gly Asn Gly Ser Gln Ile Ala Ala His Val
    290                 295                 300
```

```
Ile Ser Glu Ala Ser Ser Lys Thr Thr Ser Val Leu Gln Trp Ala Glu
305                 310                 315                 320

Lys Gly Tyr Tyr Thr Met Ser Asn Asn Leu Val Thr Leu Glu Asn Gly
            325                 330                 335

Lys Gln Leu Thr Val Lys Arg Gln Gly Leu Tyr Tyr Ile Tyr Ala Gln
                340                 345                 350

Val Thr Phe Cys Ser Asn Arg Glu Ala Ser Ser Gln Ala Pro Phe Ile
            355                 360                 365

Ala Ser Leu Ser Leu Lys Ser Pro Gly Arg Phe Glu Arg Ile Leu Leu
370                 375                 380

Arg Ala Ala Asn Thr His Ser Ser Ala Lys Pro Cys Gly Gln Gln Ser
385                 390                 395                 400

Ile His Leu Gly Gly Val Phe Glu Leu Gln Pro Gly Ala Ser Val Phe
                405                 410                 415

Val Asn Val Thr Asp Pro Ser Gln Val Ser His Gly Thr Gly Phe Thr
            420                 425                 430

Ser Phe Gly Leu Leu Lys Leu Gly Ser Gly Ser Ser Ser Ser Ser Ser
        435                 440                 445

Ser Ser Gly Ser Cys Asp Lys Thr His Thr Cys Pro Pro Cys Pro Ala
450                 455                 460

Pro Glu Leu Leu Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
            500                 505                 510

Asp Gly Val Glu Val His Asn Ala Lys Thr Lys Pro Arg Glu Glu Gln
        515                 520                 525

Tyr Ser Thr Tyr Arg Val Val Ser Val Leu Thr Val Leu His Gln
530                 535                 540

Asp Trp Leu Asn Gly Lys Glu Tyr Lys Cys Lys Val Ser Asn Lys Ala
545                 550                 555                 560

Leu Pro Ala Pro Ile Glu Lys Thr Ile Ser Lys Ala Lys Gly Gln Pro
                565                 570                 575

Arg Glu Pro Gln Val Tyr Thr Leu Pro Pro Ser Arg Glu Glu Met Thr
            580                 585                 590

Lys Asn Gln Val Ser Leu Thr Cys Leu Val Lys Gly Phe Tyr Pro Ser
        595                 600                 605

Asp Ile Ala Val Glu Trp Glu Ser Asn Gly Gln Pro Glu Asn Asn Tyr
610                 615                 620

Lys Thr Thr Pro Pro Val Leu Asp Ser Asp Gly Ser Phe Phe Leu Tyr
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
            660                 665                 670

Ser Leu Ser Leu Ser Pro Gly Lys
        675                 680

<210> SEQ ID NO 35
<211> LENGTH: 714
<212> TYPE: PRT
<213> ORGANISM: Artificial Sequence
<223> OTHER INFORMATION: "Protein-C"
<220> FEATURE:
```

<223> OTHER INFORMATION: Protein-C

<400> SEQUENCE: 35

```
Met Glu Thr Asp Thr Leu Leu Val Phe Val Leu Leu Val Trp Val Pro
1               5                   10                  15

Ala Gly Asn Gly Gln Ile Ala Ala His Val Ile Ser Glu Ala Ser Ser
            20                  25                  30

Lys Thr Thr Ser Val Leu Gln Trp Ala Glu Lys Gly Tyr Tyr Thr Met
                35                  40                  45

Ser Asn Asn Leu Val Thr Leu Glu Asn Gly Lys Gln Leu Thr Val Lys
        50                  55                  60

Arg Gln Gly Leu Tyr Tyr Ile Tyr Ala Gln Val Thr Phe Cys Ser Asn
65                  70                  75                  80

Arg Glu Ala Ser Ser Gln Ala Pro Phe Ile Ala Ser Leu Ala Leu Lys
                85                  90                  95

Ser Pro Gly Arg Phe Glu Arg Ile Leu Leu Arg Ala Ala Asn Thr His
            100                 105                 110

Ser Ser Ala Lys Pro Cys Gly Gln Gln Ser Ile His Leu Gly Gly Val
            115                 120                 125

Phe Glu Leu Gln Pro Gly Ala Ser Val Phe Val Asn Val Thr Asp Pro
130                 135                 140

Ser Gln Val Ser His Gly Thr Gly Phe Thr Ser Phe Gly Leu Leu Lys
145                 150                 155                 160

Leu Gly Ser Gly Ser Gly Asn Gly Ser Gln Ile Ala Ala His Val Ile
                165                 170                 175

Ser Glu Ala Ser Ser Lys Thr Thr Ser Val Leu Gln Trp Ala Glu Lys
            180                 185                 190

Gly Tyr Tyr Thr Met Ser Asn Asn Leu Val Thr Leu Glu Asn Gly Lys
            195                 200                 205

Gln Leu Thr Val Lys Arg Gln Gly Leu Tyr Tyr Ile Tyr Ala Gln Val
        210                 215                 220

Thr Phe Cys Ser Asn Arg Glu Ala Ser Ser Gln Ala Pro Phe Ile Ala
225                 230                 235                 240

Ser Leu Ala Leu Lys Ser Pro Gly Arg Phe Glu Arg Ile Leu Leu Arg
                245                 250                 255

Ala Ala Asn Thr His Ser Ser Ala Lys Pro Cys Gly Gln Gln Ser Ile
            260                 265                 270

His Leu Gly Gly Val Phe Glu Leu Gln Pro Gly Ala Ser Val Phe Val
        275                 280                 285

Asn Val Thr Asp Pro Ser Gln Val Ser His Gly Thr Gly Phe Thr Ser
            290                 295                 300

Phe Gly Leu Leu Lys Leu Gly Ser Gly Ser Gly Asn Gly Ser Gln Ile
305                 310                 315                 320

Ala Ala His Val Ile Ser Glu Ala Ser Ser Lys Thr Thr Ser Val Leu
                325                 330                 335

Gln Trp Ala Glu Lys Gly Tyr Tyr Thr Met Ser Asn Asn Leu Val Thr
            340                 345                 350

Leu Glu Asn Gly Lys Gln Leu Thr Val Lys Arg Gln Gly Leu Tyr Tyr
            355                 360                 365

Ile Tyr Ala Gln Val Thr Phe Cys Ser Asn Arg Glu Ala Ser Ser Gln
        370                 375                 380

Ala Pro Phe Ile Ala Ser Leu Ala Leu Lys Ser Pro Gly Arg Phe Glu
385                 390                 395                 400
```

```
Arg Ile Leu Leu Arg Ala Ala Asn Thr His Ser Ser Ala Lys Pro Cys
                405                 410                 415

Gly Gln Gln Ser Ile His Leu Gly Gly Val Phe Glu Leu Gln Pro Gly
            420                 425                 430

Ala Ser Val Phe Val Asn Val Thr Asp Pro Ser Gln Val Ser His Gly
        435                 440                 445

Thr Gly Phe Thr Ser Phe Gly Leu Leu Lys Leu Gly Ser Gly Ser Ser
    450                 455                 460

Ser Ser Ser Ser Ser Gly Ser Cys Asp Lys Thr His Thr Cys Pro
465                 470                 475                 480

Pro Cys Pro Ala Pro Glu Leu Leu Gly Gly Pro Ser Val Phe Leu Phe
            485                 490                 495

Pro Pro Lys Pro Lys Asp Thr Leu Met Ile Ser Arg Thr Pro Glu Val
        500                 505                 510

Thr Cys Val Val Val Asp Val Ser His Glu Asp Pro Glu Val Lys Phe
    515                 520                 525

Asn Trp Tyr Val Asp Gly Val Glu Val His Asn Ala Lys Thr Lys Pro
530                 535                 540

Arg Glu Glu Gln Tyr Ser Ser Thr Tyr Arg Val Val Ser Val Leu Thr
545                 550                 555                 560

Val Leu His Gln Asp Trp Leu Asn Gly Lys Glu Tyr Lys Cys Lys Val
            565                 570                 575

Ser Asn Lys Ala Leu Pro Ala Pro Ile Glu Lys Thr Ile Ser Lys Ala
        580                 585                 590

Lys Gly Gln Pro Arg Glu Pro Gln Val Tyr Thr Leu Pro Pro Ser Arg
    595                 600                 605

Glu Glu Met Thr Lys Asn Gln Val Ser Leu Thr Cys Leu Val Lys Gly
    610                 615                 620

Phe Tyr Pro Ser Asp Ile Ala Val Glu Trp Glu Ser Asn Gly Gln Pro
625                 630                 635                 640

Glu Asn Asn Tyr Lys Thr Thr Pro Pro Val Leu Asp Ser Asp Gly Ser
            645                 650                 655

Phe Phe Leu Tyr Ser Lys Leu Thr Val Asp Lys Ser Arg Trp Gln Gln
        660                 665                 670

Gly Asn Val Phe Ser Cys Ser Val Met His Glu Ala Leu His Asn His
    675                 680                 685

Tyr Thr Gln Lys Ser Leu Ser Leu Ser Pro Gly Ser Ser Ser Ser Ser
    690                 695                 700

Ser Ala Trp Ser His Pro Gln Phe Glu Lys
705                 710

<210> SEQ ID NO 36
<211> LENGTH: 439
<212> TYPE: PRT
<213> ORGANISM: Artificial Sequence
<223> OTHER INFORMATION: "fusion protein variant"
<220> FEATURE:
<223> OTHER INFORMATION: fusion protein variant

<400> SEQUENCE: 36

Gln Ile Ala Ala His Val Ile Ser Glu Ala Ser Ser Lys Thr Thr Ser
1               5                   10                  15

Val Leu Gln Trp Ala Glu Lys Gly Tyr Tyr Thr Met Ser Asn Asn Leu
            20                  25                  30

Val Thr Leu Glu Asn Gly Lys Gln Leu Thr Val Lys Arg Gln Gly Leu
        35                  40                  45
```

Tyr Tyr Ile Tyr Ala Gln Val Thr Phe Cys Ser Asn Arg Glu Ala Ser
50                  55                  60

Ser Gln Ala Pro Phe Ile Ala Ser Leu Ser Leu Lys Ser Pro Gly Arg
65                  70                  75                  80

Phe Glu Arg Ile Leu Leu Arg Ala Ala Asn Thr His Ser Ser Ala Lys
                85                  90                  95

Pro Cys Gly Gln Gln Ser Ile His Leu Gly Gly Val Phe Glu Leu Gln
                100                 105                 110

Pro Gly Ala Ser Val Phe Val Asn Val Thr Asp Pro Ser Gln Val Ser
                115                 120                 125

His Gly Thr Gly Phe Thr Ser Phe Gly Leu Leu Lys Leu Gly Ser Gly
                130                 135                 140

Ser Gly Asn Gly Ser Gln Ile Ala Ala His Val Ile Ser Glu Ala Ser
145                 150                 155                 160

Ser Lys Thr Thr Ser Val Leu Gln Trp Ala Glu Lys Gly Tyr Tyr Thr
                165                 170                 175

Met Ser Asn Asn Leu Val Thr Leu Glu Asn Gly Lys Gln Leu Thr Val
                180                 185                 190

Lys Arg Gln Gly Leu Tyr Tyr Ile Tyr Ala Gln Val Thr Phe Cys Ser
                195                 200                 205

Asn Arg Glu Ala Ser Ser Gln Ala Pro Phe Ile Ala Ser Leu Ser Leu
210                 215                 220

Lys Ser Pro Gly Arg Phe Glu Arg Ile Leu Leu Arg Ala Ala Asn Thr
225                 230                 235                 240

His Ser Ser Ala Lys Pro Cys Gly Gln Gln Ser Ile His Leu Gly Gly
                245                 250                 255

Val Phe Glu Leu Gln Pro Gly Ala Ser Val Phe Val Asn Val Thr Asp
                260                 265                 270

Pro Ser Gln Val Ser His Gly Thr Gly Phe Thr Ser Phe Gly Leu Leu
                275                 280                 285

Lys Leu Gly Ser Gly Ser Gly Asn Gly Ser Gln Ile Ala Ala His Val
290                 295                 300

Ile Ser Glu Ala Ser Ser Lys Thr Thr Ser Val Leu Gln Trp Ala Glu
305                 310                 315                 320

Lys Gly Tyr Tyr Thr Met Ser Asn Asn Leu Val Thr Leu Glu Asn Gly
                325                 330                 335

Lys Gln Leu Thr Val Lys Arg Gln Gly Leu Tyr Tyr Ile Tyr Ala Gln
                340                 345                 350

Val Thr Phe Cys Ser Asn Arg Glu Ala Ser Ser Gln Ala Pro Phe Ile
                355                 360                 365

Ala Ser Leu Ser Leu Lys Ser Pro Gly Arg Phe Glu Arg Ile Leu Leu
                370                 375                 380

Arg Ala Ala Asn Thr His Ser Ser Ala Lys Pro Cys Gly Gln Gln Ser
385                 390                 395                 400

Ile His Leu Gly Gly Val Phe Glu Leu Gln Pro Gly Ala Ser Val Phe
                405                 410                 415

Val Asn Val Thr Asp Pro Ser Gln Val Ser His Gly Thr Gly Phe Thr
                420                 425                 430

Ser Phe Gly Leu Leu Lys Leu
                435

<210> SEQ ID NO 37
<211> LENGTH: 2147

```
<212> TYPE: DNA
<213> ORGANISM: Artificial Sequence
<223> OTHER INFORMATION: "DNA Sequence encoding fusion protein "
<220> FEATURE:
<223> OTHER INFORMATION: DNA Sequence encoding fusion protein

<400> SEQUENCE: 37
aagctttagg gataacaggg taatagccgc caccatggag actgacaccc tgctggtgtt      60
cgtgctgctg gtctgggtgc ctgcaggaaa tggacagatc gcagctcatg tgataagtga     120
ggcaagctcg aagacgacta gcgtattgca gtgggcagag aagggtact acaccatgtc      180
caacaacctc gtcacgctgg agaacggcaa acagctcacc gtcaagcgac agggcctgta     240
ctacatctac gcacaagtca ccttctgttc taaccgagag gcttccagtc aagcacctt      300
cattgcttcc ctgtgcctga atcccctgg tcgattcgag aggatactgc tcagggcagc      360
taacactcac tccagtgcta agccttgcgg tcagcagagt atccacctcg gcggcgtatt     420
cgagctgcaa ccaggagctt ccgtctttgt gaacgtgact gacccttctc aagtctctca     480
cggaacagga ttcacctctt tcgggctcct aaagctgggt ccggaagcg gtaatggtag      540
tcaaatcgct gcccatgtaa tttccgaggc ttcgtcaaag actacgtctg ttctacaatg     600
ggccgagaaa ggctactata ccatgtcaaa taatctcgtc actcttgaga acgggaagca     660
gcttaccgtt aaacgtcagg gactttacta catttatgcc caagtcactt tctgctcaaa     720
tcgagaggca agctcccaag caccgttcat agcatcactc tgcctcaagt cccctggaag     780
gtttgaacga atactactta gggccgctaa tacacattcg agtgcaaagc cttgcggaca     840
gcaaagcatt catttaggtg gagtcttcga gcttcaacca ggagcctctg tattcgtcaa     900
cgtaacggac ccatcgcaag tatcccacgg cactggtttc acctcattcg gtttgctgaa     960
gttaggaagc ggcagtggaa acggttccca aatagctgcc catgtcatct cggaagcctc    1020
aagcaagacg acaagtgtct tgcaatgggc cgaaaagggt tattatacta tgtctaataa    1080
cctagtgacc ctagagaacg gtaaacaact tactgttaag cgccagggac tttattatat    1140
atatgctcag gtaacattct gctcgaatcg ggaagcatct tcacaggctc cttttatcgc    1200
tagtttatgt ctgaagagcc ccggacgatt tgagaggata ttgcttagag ccgcgaatac    1260
acacagttca gccaaacctt gtggacaaca gagtattcac ttaggtggcg tgtttgaatt    1320
acaaccaggg gcatcagtgt tcgtaaacgt aacagatccc agtcaggtct cgcacgggac    1380
gggatttact tcctttggtt tgctgaaatt aggctcggga tcctcgagtt catcgtcctc    1440
atccggctca tgtgataaga cccacacctg ccctccctgt cctgccctg agctgctggg     1500
cggaccttct gtgttcctgt tccccccaa gcctaaggac accctgatga tctccaggac    1560
ccctgaggtg acctgtgtgg tggtggacgt gtctcacgaa gatcccgagg tgaagttcaa    1620
ctggtacgtg gacggcgtgg aggtccacaa cgccaagacc aagcctaggg aggagcagta    1680
cagctccacc taccgggtgg tgtctgtgct gaccgtgctg caccaggatt ggctgaacgg    1740
aaaggagtat aagtgtaagg tctccaacaa ggccctgcct gccccatcg agaaaaccat    1800
ctccaaggcc aagggccagc ctcgggagcc tcaggtgtac accctgcctc ctagcaggga    1860
ggagatgacc aagaaccagg tgtccctgac ctgtctggtg aagggcttct acccttccga    1920
tatcgccgtg gagtgggagt ctaatggcca gcccgagaac aactacaaga ccacccctcc    1980
tgtgctggac tctgacggct ccttcttcct gtactccaag ctgaccgtgg acaagtccag    2040
atggcagcag ggcaacgtgt tctcctgctc cgtgatgcac gaggccctgc acaatcacta    2100
cacccagaag tccctgtctc tgagtccggg caaataatag gcgcgcc                  2147
```

<210> SEQ ID NO 38
<211> LENGTH: 218
<212> TYPE: PRT
<213> ORGANISM: Artificial Sequence
<223> OTHER INFORMATION: "Protein-X (trivalent control protein incl.
    Signal Peptide and Strep Tag)"
<220> FEATURE:
<223> OTHER INFORMATION: Protein-X (trivalent control protein incl.
    Signal Peptide and Strep Tag)

<400> SEQUENCE: 38

Met Glu Thr Asp Thr Leu Leu Val Phe Val Leu Leu Trp Val Pro
1               5                   10                  15

Ala Gly Asn Gly Gln Ile Ala Ala His Val Ile Ser Glu Ala Ser Ser
            20                  25                  30

Lys Thr Thr Ser Val Leu Gln Trp Ala Glu Lys Gly Tyr Tyr Thr Met
        35                  40                  45

Ser Asn Asn Leu Val Thr Leu Glu Asn Gly Lys Gln Leu Thr Val Lys
    50                  55                  60

Arg Gln Gly Leu Tyr Tyr Ile Tyr Ala Gln Val Thr Phe Cys Ser Asn
65                  70                  75                  80

Arg Glu Ala Ser Ser Gln Ala Pro Phe Ile Ala Ser Leu Cys Leu Lys
                85                  90                  95

Ser Pro Gly Arg Phe Glu Arg Ile Leu Leu Arg Ala Ala Asn Thr His
            100                 105                 110

Ser Ser Ala Lys Pro Cys Gly Gln Gln Ser Ile His Leu Gly Gly Val
        115                 120                 125

Phe Glu Leu Gln Pro Gly Ala Ser Val Phe Val Asn Val Thr Asp Pro
    130                 135                 140

Ser Gln Val Ser His Gly Thr Gly Phe Thr Ser Phe Gly Leu Leu Lys
145                 150                 155                 160

Leu Gly Ser Gly Ser Ser Gly Ser Ser Gly Ser Gly Tyr
                165                 170                 175

Ile Glu Asp Ala Pro Ser Asp Gly Lys Phe Tyr Val Arg Lys Asp Gly
            180                 185                 190

Ala Trp Val Glu Leu Pro Thr Ala Ser Gly Pro Ser Ser Ser Ser Ser
        195                 200                 205

Ser Ala Trp Ser His Pro Gln Phe Glu Lys
    210                 215

<210> SEQ ID NO 39
<211> LENGTH: 177
<212> TYPE: PRT
<213> ORGANISM: Artificial Sequence
<223> OTHER INFORMATION: "Protein-X2 (trivalent control protein incl.
    Signal Peptide and Strep Tag)"
<220> FEATURE:
<223> OTHER INFORMATION: Protein-X2 (trivalent control protein incl.
    Signal Peptide and Strep Tag)

<400> SEQUENCE: 39

Met Glu Thr Asp Thr Leu Leu Val Phe Val Leu Leu Trp Val Pro
1               5                   10                  15

Ala Gly Asn Gly Gln Ile Ala Ala His Val Ile Ser Glu Ala Ser Ser
            20                  25                  30

Lys Thr Thr Ser Val Leu Gln Trp Ala Glu Lys Gly Tyr Tyr Thr Met
        35                  40                  45

Ser Asn Asn Leu Val Thr Leu Glu Asn Gly Lys Gln Leu Thr Val Lys

-continued

```
                  50                    55                      60
Arg Gln Gly Leu Tyr Tyr Ile Tyr Ala Gln Val Thr Phe Cys Ser Asn
 65                  70                    75                   80

Arg Glu Ala Ser Ser Gln Ala Pro Phe Ile Ala Ser Leu Cys Leu Lys
                 85                  90                  95

Ser Pro Gly Arg Phe Glu Arg Ile Leu Leu Arg Ala Ala Asn Thr His
                100                 105                 110

Ser Ser Ala Lys Pro Cys Gly Gln Gln Ser Ile His Leu Gly Gly Val
            115                 120                 125

Phe Glu Leu Gln Pro Gly Ala Ser Val Phe Val Asn Val Thr Asp Pro
            130                 135                 140

Ser Gln Val Ser His Gly Thr Gly Phe Thr Ser Phe Gly Leu Leu Lys
145                 150                 155                 160

Leu Gly Ser Ser Ser Ser Ser Ser Ala Trp Ser His Pro Gln Phe Glu
                165                 170                 175

Lys
```